United States Patent
Miller et al.

(10) Patent No.: US 7,022,733 B2
(45) Date of Patent: Apr. 4, 2006

(54) SUBSTITUTED 2-PHENYL BENZOFURANS AS ESTROGENIC AGENTS

(75) Inventors: Christopher P. Miller, Wayne, PA (US); Michael D. Collini, Clifton Heights, PA (US); David H. Kaufman, Berwyn, PA (US); Robert L. Morris, Wayne, PA (US); Robert R. Singhaus, Jr., Blandon, PA (US); John W. Ullrich, Exton, PA (US); Heather A. Harris, Phoenixville, PA (US); James C. Keith, Jr., Andover, MA (US); Leo M. Albert, Burlington, MA (US); Rayomand J. Unwalla, Eagleville, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/828,970

(22) Filed: Apr. 21, 2004

(65) Prior Publication Data
US 2005/0038107 A1 Feb. 17, 2005

Related U.S. Application Data

(62) Division of application No. 10/320,207, filed on Dec. 16, 2002, now Pat. No. 6,774,248.

(60) Provisional application No. 60/341,638, filed on Dec. 18, 2001.

(51) Int. Cl.
*A61K 31/343* (2006.01)

(52) U.S. Cl. ..................... 514/469
(58) Field of Classification Search ............ 514/469
See application file for complete search history.

(56) References Cited

U.S. PATENT DOCUMENTS 4,863,958 A   9/1989 Belanger et al.
5,087,638 A   2/1992 Belanger et al.
2002/0099086 A1  7/2002 Achenbach et al.

FOREIGN PATENT DOCUMENTS

EP   0 731 098 A   9/1996
WO   WO 02/16333   2/2002

OTHER PUBLICATIONS

Cameron, et al., "Photogeneration of amines from alpha-keto carbamates: photochemical studies," J. Am. Chem. Soc. (1996) 118:12925-12937.

Lee and Balasubramanian. "Studies on a dithiane-protected benzoin photolabile safety catch linker for solid-phase synthesis." J. Org. Chem. (1999) 64:3454-3460.

Teo, et al., "Synthesis of 2-(p-chlorobenzyl)-3-aryl-6-methoxybenzofurans as selective ligands for antiestrogen-binding sites. Effects on cell proliferation and cholesterol synthesis," J. Med. Chem. (1992) 35:1330-1339.

*Primary Examiner*—Bernard Dentz
(74) *Attorney, Agent, or Firm*—Arnold S. Milowsky; Michael P. Straher; Cozen O'Connor

(57) ABSTRACT

This invention provides estrogen receptor modulators of formula I, having the structure

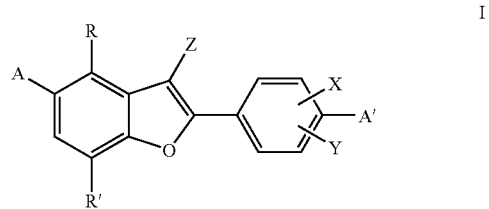

wherein
R, R', A, A', X, Y, and Y are as defined in the specification, or a pharmaceutically acceptable salt thereof.

1 Claim, No Drawings

SUBSTITUTED 2-PHENYL BENZOFURANS AS ESTROGENIC AGENTS

This application is a divisional of U.S. patent application Ser. No. 10/320,207 filed Dec. 16, 2002, (now U.S. Pat. No. 6,774,248) which claims priority to Provisional Application Ser. No. 60/341,638 filed Dec. 18, 2001, the entire disclosure of each is hereby incorporated by reference.

BACKGROUND OF THE INVENTION

This invention relates to substituted 2-phenyl benzofurans, which are useful as estrogenic agents.

The pleiotropic effects of estrogens in mammalian tissues have been well documented, and it is now appreciated that estrogens affect many organ systems [Mendelsohn and Karas, New England journal of Medicine 340: 1801–1811 (1999), Epperson, et al., Psychosomatic Medicine 61: 676–697 (1999), Crandall, Journal of Womens Health & Gender Based Medicine 8: 1155–1166 (1999), Monk and Brodaty, Dementia & Geriatric Cognitive Disorders 11: 1–10 (2000), Hurn and Macrae, Journal of Cerebral Blood Flow & Metabolism 20: 631–652 (2000), Calvin, Maturitas 34: 195–210 (2000), Finking, et al., Zeitschrift fur Kardiologie 89: 442–453 (2000), Brincat, Maturitas 35: 107–117 (2000), Al-Azzawi, Postgraduate Medical Journal 77: 292–304 (2001)]. Estrogens can exert effects on tissues in several ways, and the most well characterized mechanism of action is their interaction with estrogen receptors leading to alterations in gene transcription. Estrogen receptors are ligand-activated transcription factors and belong to the nuclear hormone receptor superfamily. Other members of this family include the progesterone, androgen, glucocorticoid and mineralocorticoid receptors. Upon binding ligand, these receptors dimerize and can activate gene transcription either by directly binding to specific sequences on DNA (known as response elements) or by interacting with other transcription factors (such as AP1), which in turn bind directly to specific DNA sequences [Moggs and Orphanides, EMBO Reports 2: 775–781 (2001), Hall, et al., Journal of Biological Chemistry 276: 36869–36872 (2001), McDonnell, Principles Of Molecular Regulation. p 351–361 (2000)]. A class of "coregulatory" proteins can also interact with the ligand-bound receptor and further modulate its transcriptional activity [McKenna, et al., Endocrine Reviews. 20: 321–344 (1999)]. It has also been shown that estrogen receptors can suppress NFκB-mediated transcription in both a ligand-dependent and independent manner [Quaedackers, et al., Endocrinology 142: 1156–1166 (2001), Bhat, et al., Journal of Steroid Biochemistry & Molecular Biology 67: 233–240 (1998), Pelzer, et al., Biochemical & Biophysical Research Communications 286: 1153–7 (2001)].

Estrogen receptors can also be activated by phosphorylation. This phosphorylation is mediated by growth factors such as EGF and causes changes in gene transcription in the absence of ligand [Moggs and Orphanides, EMBO Reports 2: 775–781 (2001), Hall, et al., Journal of Biological Chemistry 276: 36869–36872 (2001)].

A less well-characterized means by which estrogens can affect cells is through a so-called membrane receptor. The existence of such a receptor is controversial, but it has been well documented that estrogens can elicit very rapid nongenomic responses from cells. The molecular entity responsible for transducing these effects has not been definitively isolated, but there is evidence to suggest it is at least related to the nuclear forms of the estrogen receptors [Levin, Journal of Applied Physiology 91: 1860–1867 (2001), Levin, Trends in Endocrinology & Metabolism 10: 374–377 (1999)].

Two estrogen receptors have been discovered to date. The first estrogen receptor was cloned about 15 years ago and is now referred to as ERα [Green, et al., Nature 320: 134–9 (1986)]. The second form of the estrogen receptor was found comparatively recently and is called ERβ [Kuiper, et al., Proceedings of the National Academy of Sciences of the United States of America 93: 5925–5930 (1996)]. Early work on ERβ focused on defining its affinity for a variety of ligands and indeed, some differences with ERα were seen. The tissue distribution of ERβ has been well mapped in the rodent and it is not coincident with ERα. Tissues such as the mouse and rat uterus express predominantly ERα, whereas the mouse and rat lung express predominantly ERβ [Couse, et al., Endocrinology 138: 4613–4621 (1997), Kuiper, et al., Endocrinology 138: 863–870 (1997)]. Even within the same organ, the distribution of ERα and ERβ can be compartmentalized. For example, in the mouse ovary, ERβ is highly expressed in the granulosa cells and ERα is restricted to the thecal and stromal cells [Sar and Welsch, Endocrinology 140: 963–971 (1999), Fitzpatrick, et al., Endocrinology 140: 2581–2591 (1999)]. However, there are examples where the receptors are coexpressed and there is evidence from in vitro studies that ERα and ERβ can form heterodimers, [Cowley, et al., Journal of Biological Chemistry 272: 19858–19862 (1997)].

A large number of compounds have been described that either mimic or block the activity of 17β-estradiol. Compounds having roughly the same biological effects as 17β-estradiol, the most potent endogenous estrogen, are referred to as "estrogen receptor agonists". Those which, when given in combination with 17β-estradiol, block its effects are called "estrogen receptor antagonists". In reality there is a continuum between estrogen receptor agonist and estrogen receptor antagonist activity and indeed some compounds behave as estrogen receptor agonists in some tissues and estrogen receptor antagonists in others. These compounds with mixed activity are called selective estrogen receptor modulators (SERMS) and are therapeutically useful agents (e.g. EVISTA) [McDonnell, Journal of the Society for Gynecologic Investigation 7: S10–S15 (2000), Goldstein, et al., Human Reproduction Update 6: 212–224 (2000)]. The precise reason why the same compound can have cell-specific effects has not been elucidated, but the differences in receptor conformation and/or in the milieu of coregulatory proteins have been suggested.

It has been known for some time that estrogen receptors adopt different conformations when binding ligands. However, the consequence and subtlety of these changes has been only recently revealed. The three dimensional structures of ERα and ERβ have been solved by co-crystallization with various ligands and clearly show the repositioning of helix 12 in the presence of an estrogen, receptor antagonist which sterically hinders the protein sequences required for receptor-coregulatory protein interaction [Pike, et al., Embo 18: 4608–4618 (1999), Shiau, et al., Cell 95: 927–937 (1998)]. In addition, the technique of phage display has been used to identify peptides that interact with estrogen receptors in the presence of different ligands [Paige, et al., Proceedings of the National Academy of Sciences of the United States of America 96: 3999–4004 (1999)]. For example, a peptide was identified that distinguished between ERα bound to the full estrogen receptor agonists 17β-estradiol and diethylstilbesterol. A different peptide was shown to distinguish between clomiphene bound to ERα and ERβ. These data indicate that each ligand potentially places the receptor in a unique and unpredictable conformation that is likely to have distinct biological activities.

As mentioned above, estrogens affect a panoply of biological processes. In addition, where gender differences have been described (e.g. disease frequencies, responses to challenge, etc), it is possible that the explanation involves the difference in estrogen levels between males and females.

DESCRIPTION OF THE INVENTION

This invention provides estrogenic compound of formula I having the structure,

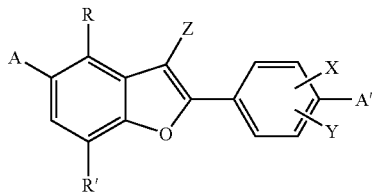

wherein
A is alkyl of 1–6 carbon atoms, halogen, trifluoroalkyl of 1–6 carbon atoms, hydroxyalkyl of 1–6 carbon atoms, $—CO_2H$, $—NH_2$, or —OP;
A' is —OP, $—CO_2P$, halogen, or hydroxyalkyl;
P is hydrogen, alkyl of 1–6carbon atoms, or phenyl;
Z is hydrogen, alkyl of 1–6 carbon atoms, halogert, $—NO_2$, —CN, triflouroalkyl of 1–6 carbon atoms, —COP, $—CO_2P$, or —C(P)=N—OP;
R and R' are each, independently, hydrogen, alkyl of 1–6 carbon atoms, alkenyl of 2–7carbon atoms, halogen, —OP, —SP, —SOP, $—SO_2P$, —SCN, trifluoroalkyl: of 1–6 carbon atoms, $—CF_2CF_3$, trifluoroalkyl of 1–6 carbon atoms, $—NO_2$, $—NH_2$, —NHOP, hydroxyalkyl of 1–6 carbon atoms, alkoxyalkyl of 1–6 carbon atoms per alkyl group, -alkyl-SP, -alkyl-SOP, -alkyl-$SO_2P$, —CN, -alkyl-CN, -alkenyl-CN, -alkylSCN, —CHFCN, $—CF_2CN$, -alkenyl-$NO_2$, haloalkyl of 1–6 carbon atoms, dihaloalkenyl of 2–7 carbon atoms, —COP, $—COCF_3$, $—CO_2P$, $—CONR_1R_2$; -alkyl-$CONR_1R_2$, -alkenyl-$CONR_1R_2$, -alkyl-COP, -alkenyl-COP, -alkenzyl-$CO_2P$, -alkenyl-$CO_2P$, oxadiazolyl, furyl, thienyl, pyrrolyl, imidazolyl, triazolyl, or tetrazolyl;
X and Y are each, independently, hydrogen, alkyl of 1–4 carbon atoms, halogen, —NO2, —CN, trifluoroalkyl of 1–6 carbon atoms, —OP, hydroxyalkyl of 1–6 carbon atoms, $—CO_2H$, or phenyl which is optionally mono- or di-substituted with hydroxyl, benzyloxy, alkoxy of 1–6 carbon atoms, or $—OCH_2CH_2NR_1R_2$;
$R_1$ and $R_2$ are each, independently, hydrogen, alkyl of 1–6 carbon atoms, or alkoxy of 1–6 carbon atoms; or $R_1$ and $R_2$ are concatenated together as $—(CH_2)_p—$;
p=2–6;
or a pharmaceutically acceptable salt thereof.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable aids when a compound of this invention contains a basic moiety. Salts may also be formed from organic and inorganic bases, such as alkali metal salts (for example, sodium, lithium, or potassium) alkaline earth metal salts, ammonium salts, alkylammonium salts containing 1–6 carbon atoms or dialkylammonium salts containing 1–6 carbon atoms in each alkyl group, and trialkylammonium salts containing 1–6 carbon atoms in each alkyl group, and compound of this invention contains an acidic moiety.

The terms alkyl, alkenyl, and alkynyl include both branched and straight chain moieties. The terms alkyl, alkenyl, and alkynyl include both unsubstituted and substituted moieties. Unsubstituted examples include methyl, ethyl, propyl, butyl, isopropyl, sec-butyl, tert-butyl, vinyl, allyl, acetylene, 1-methyl vinyl, and the like. When alkyl or alkenyl moieties are substituted, they may typically be mono-, di-, tri- or persubstituted. Halogen is the preferred substituent for substituted alkyl, alkenyl, or alkynyl moieties. Examples for a halogen substituent include 1-bromo vinyl, 1-fluoro vinyl, 1,2-difluoro vinyl, 2,2-difluorovinyl, 1,2,2-trifluorovinyl, 1,2-dibromo ethane, 1,2 difluoro ethane, 1-fluoro-2-bromo ethane, $CF_2CF_3$, $CF_2CF_2CF_3$, and the like. An example of a substituted cyanoalkyl group would be —CHFCN. The term halogen includes bromine, chlorine, fluorine, and iodine.

As used in accordance with this invention, the term "providing," with respect to providing a compound or substance covered by this invention, means either directly administering such a compound or substance, or administering a prodrug, derivative, or analog which will form the effective amount of the compound or substance within the body.

Of the compounds of this invention, it is preferred that the compound of formula I has the structure

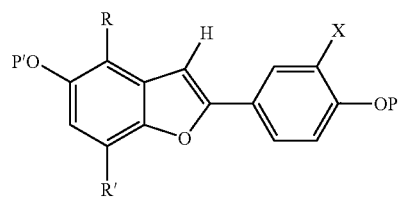

wherein
P and P' are each, independently, hydrogen, alkyl of 1–6 carbon atoms, or acyl of 2–7 carbon atoms;
X is hydrogen or halogen;
R is hydrogen, alkyl of 1–6 carbon atoms, halogen, —CN, or —CHO;
R' is alkoxy of 1–6 carbon atoms-, or cyanoalkyl having 1–6 carbon atoms in the alkyl moiety;

or a pharmaceutically acceptable salt thereof.

It is more preferred that X is fluorine; and still more preferred that X is fluorine; R is —CN; and R' is $—OCH_3$. It is also more preferred that X is hydrogen or F; R is hydrogen or F; and R' is $—CH_2$, CN.

The reagents used in the preparation of the compounds of this invention can be either commercially obtained or can be prepared by standard procedures described in the literature.

The compounds of the present invention can be prepared according to the following synthetic schemes.

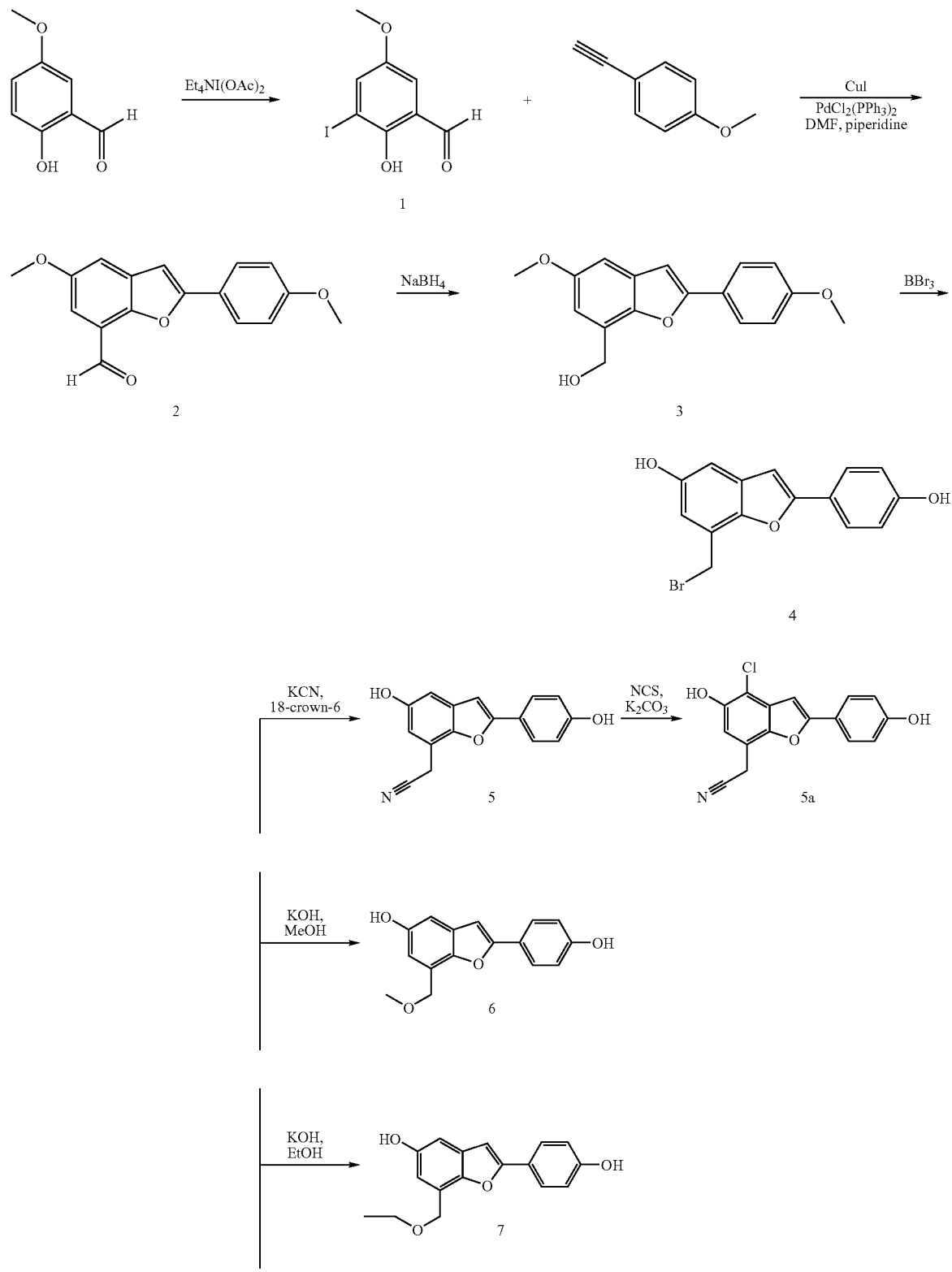

-continued
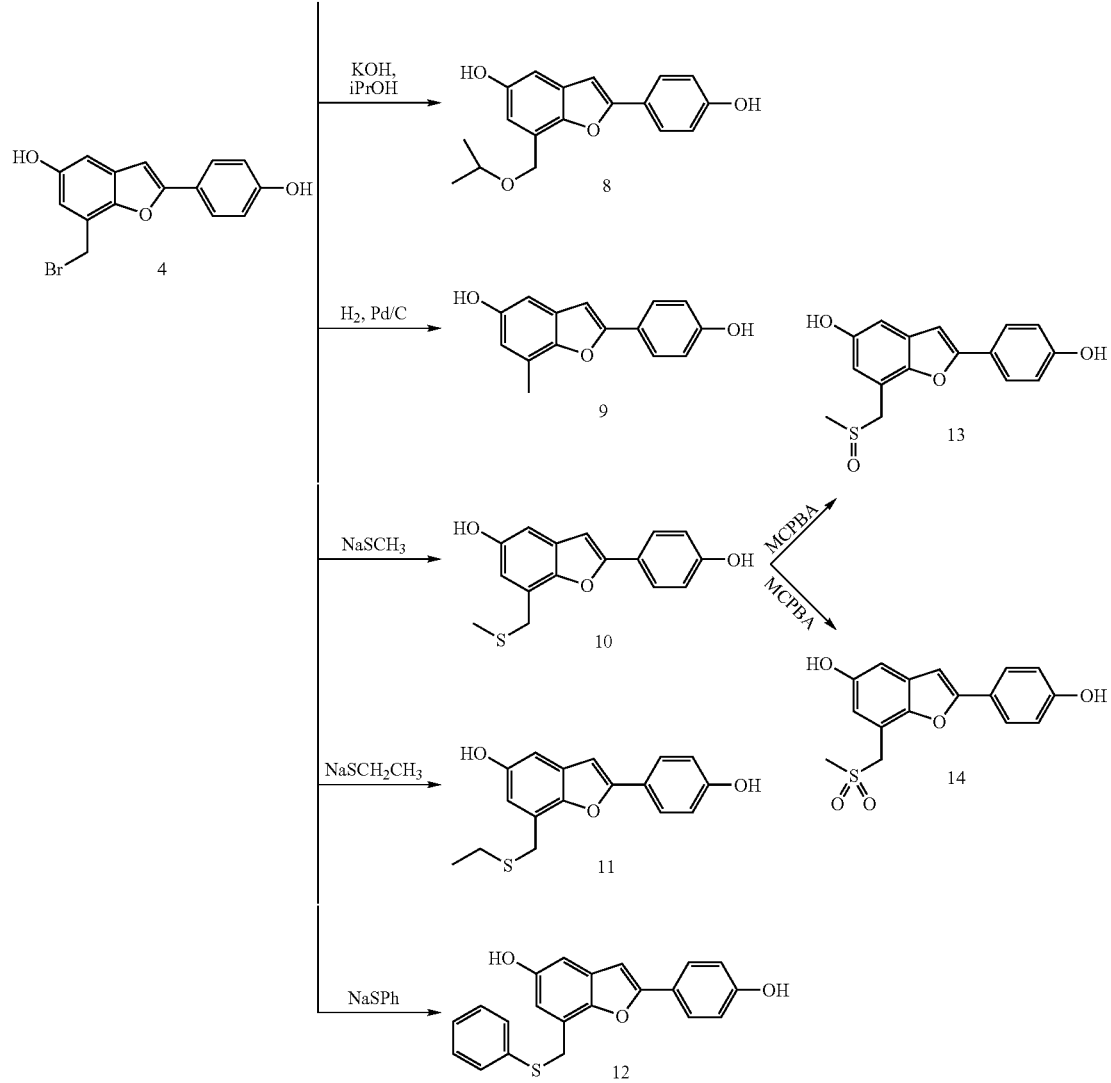
Scheme 2
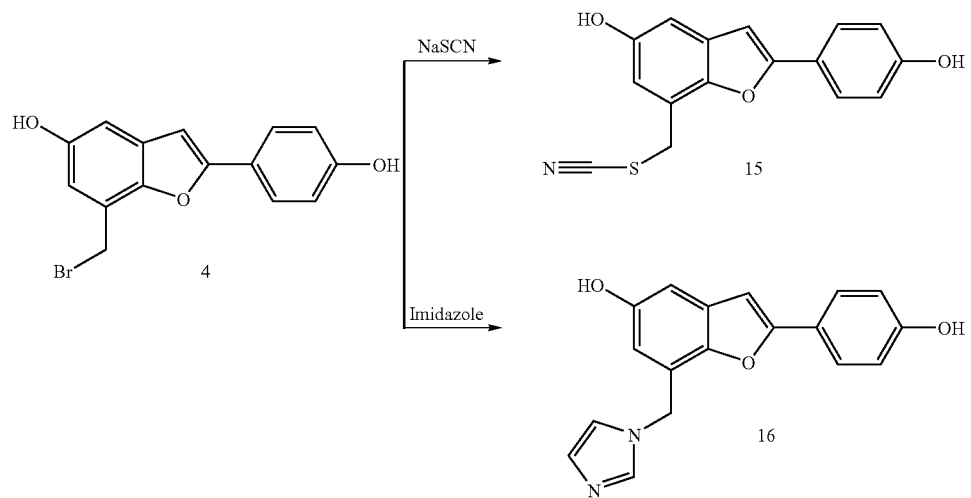

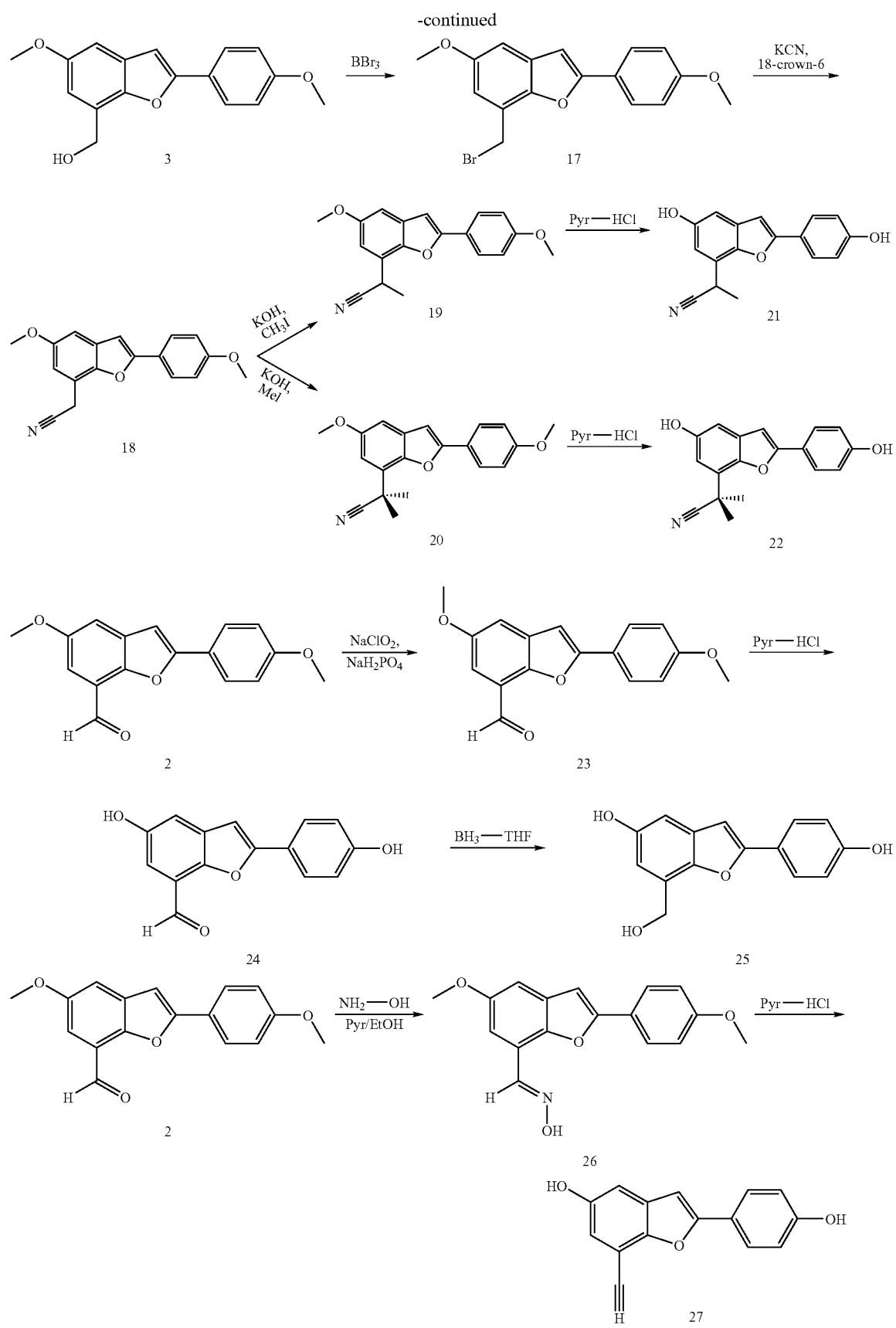

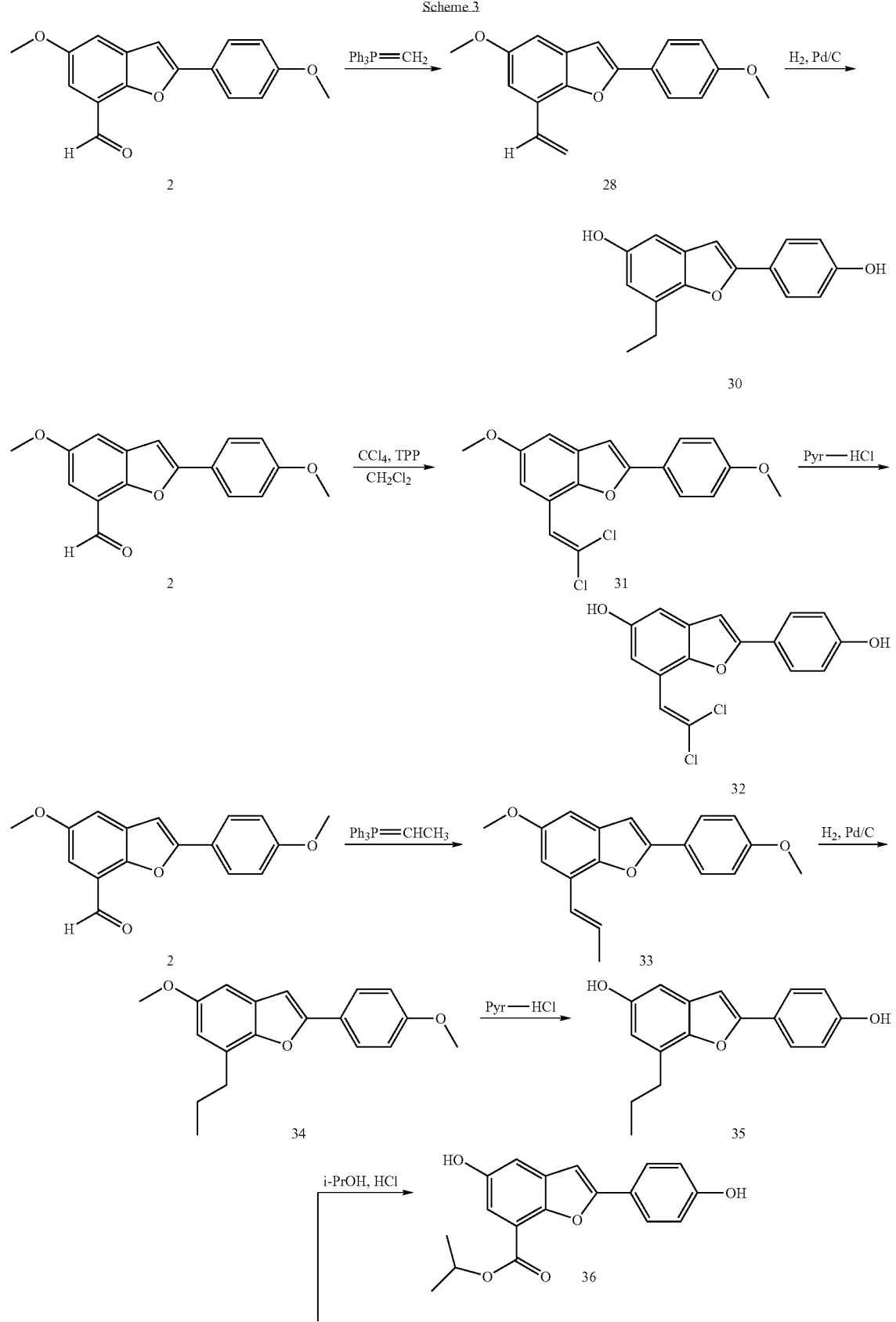

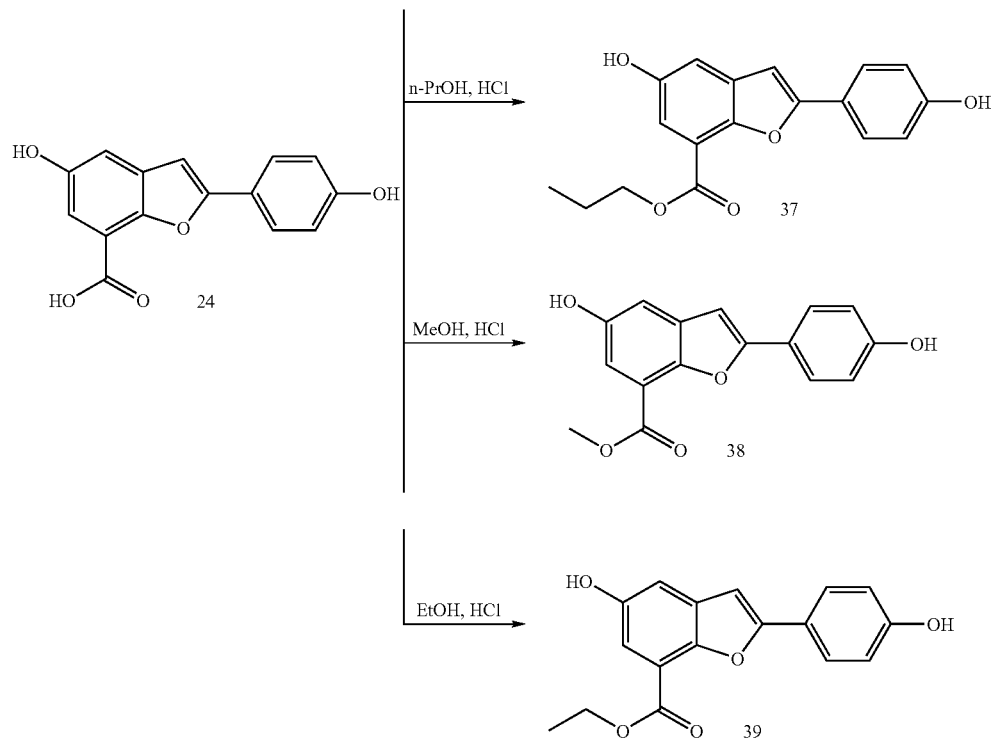
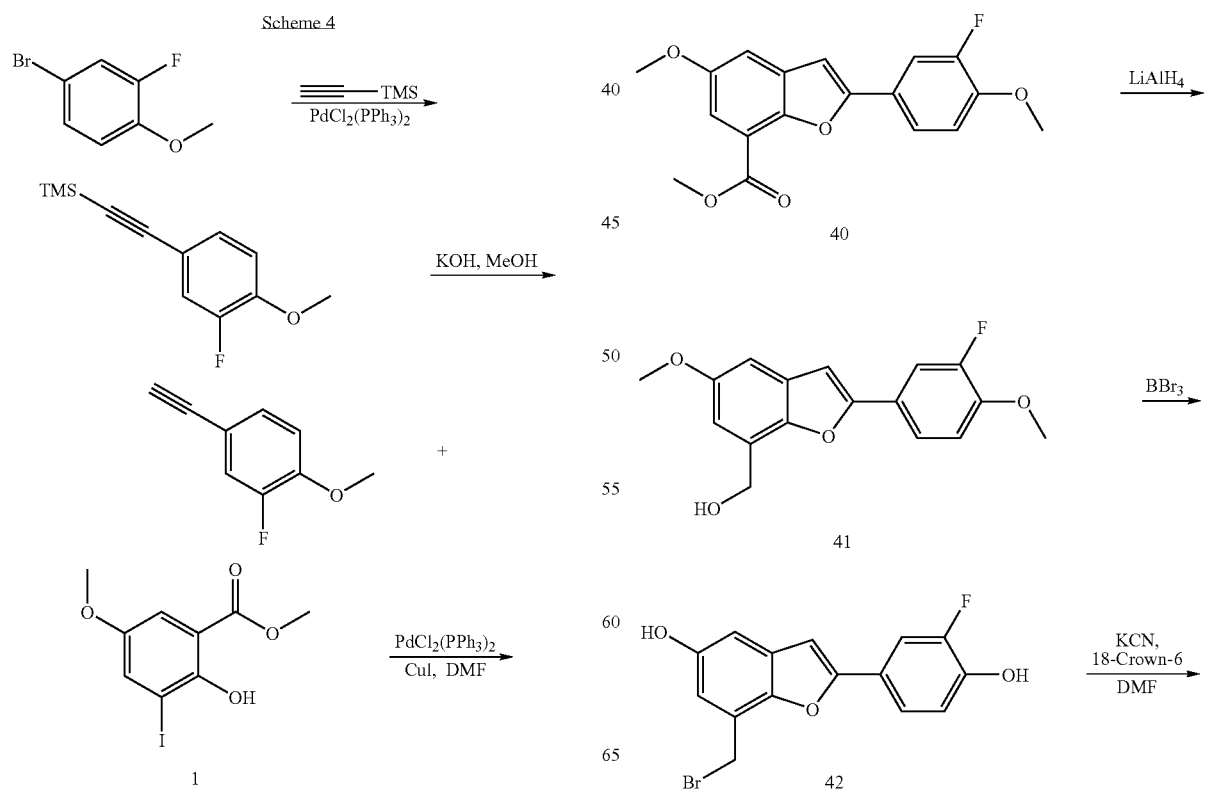

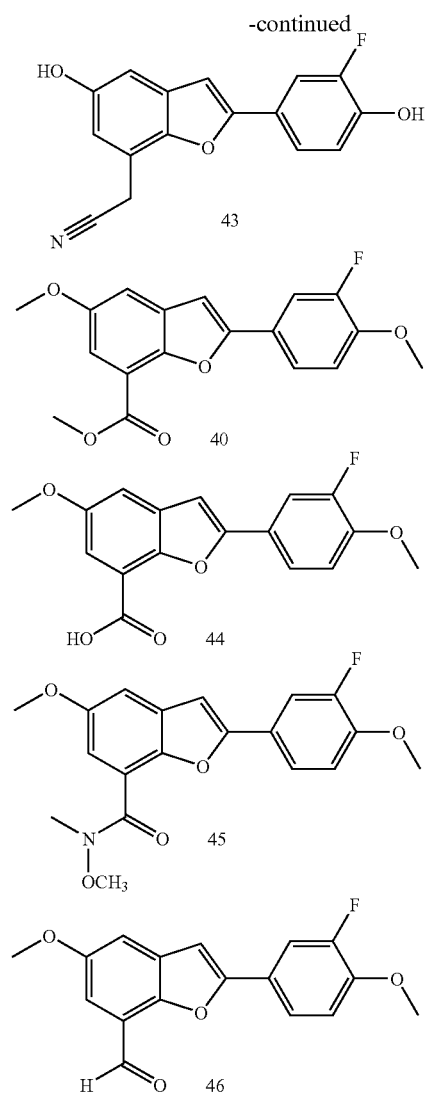
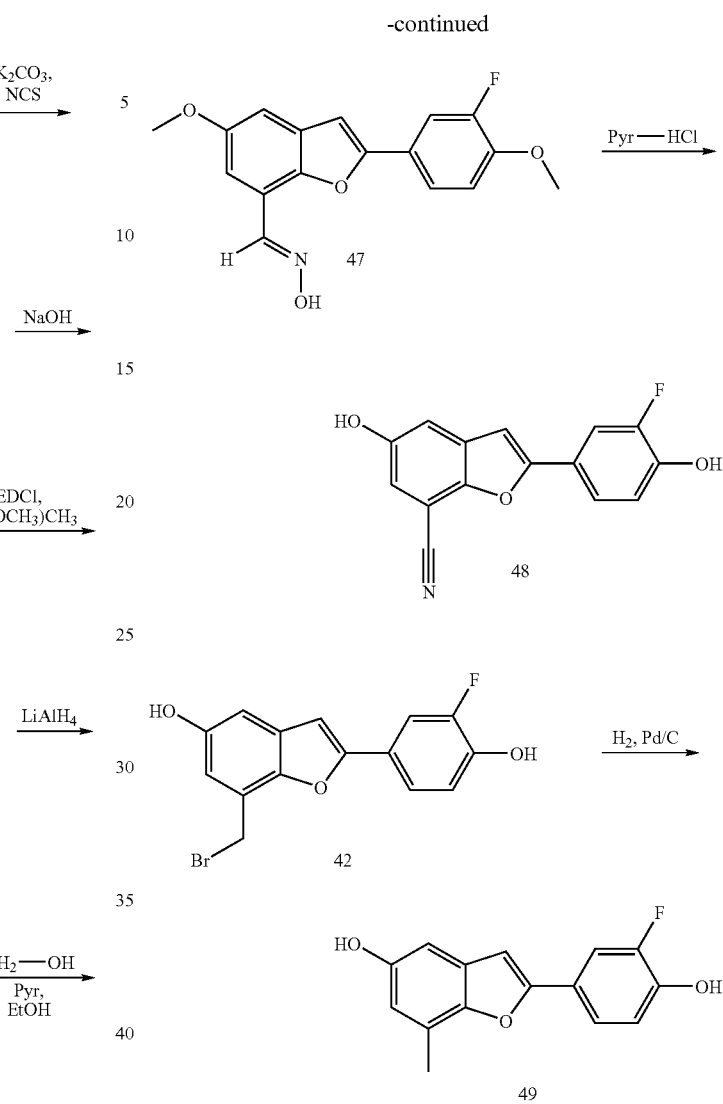
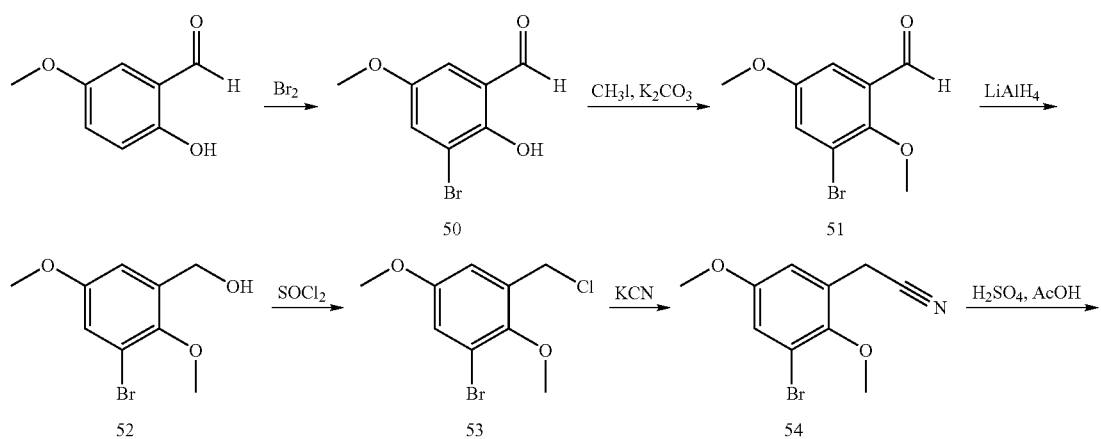
Scheme 5

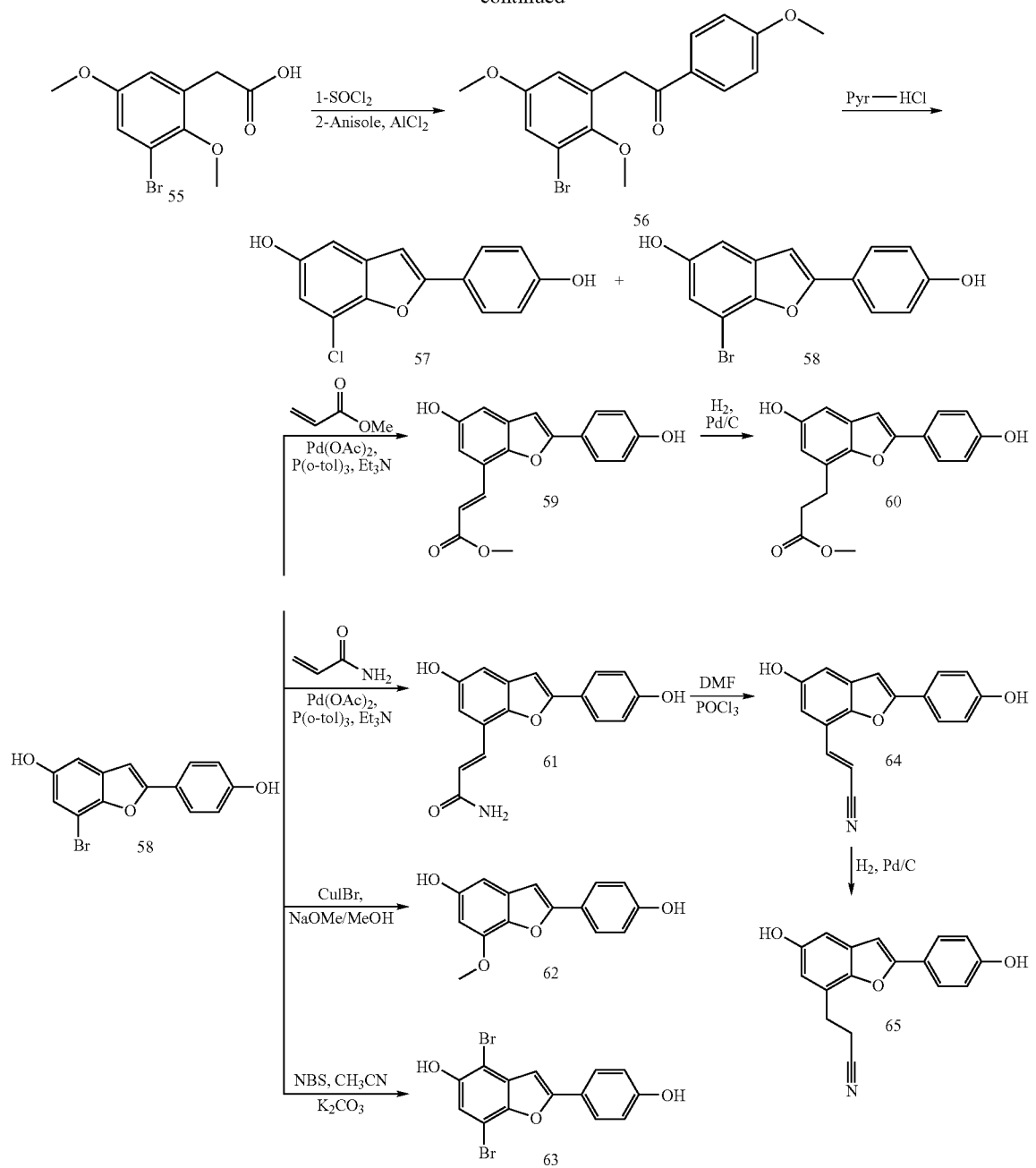
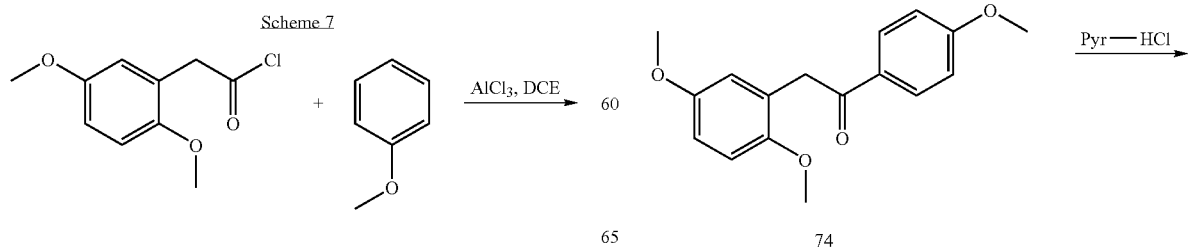

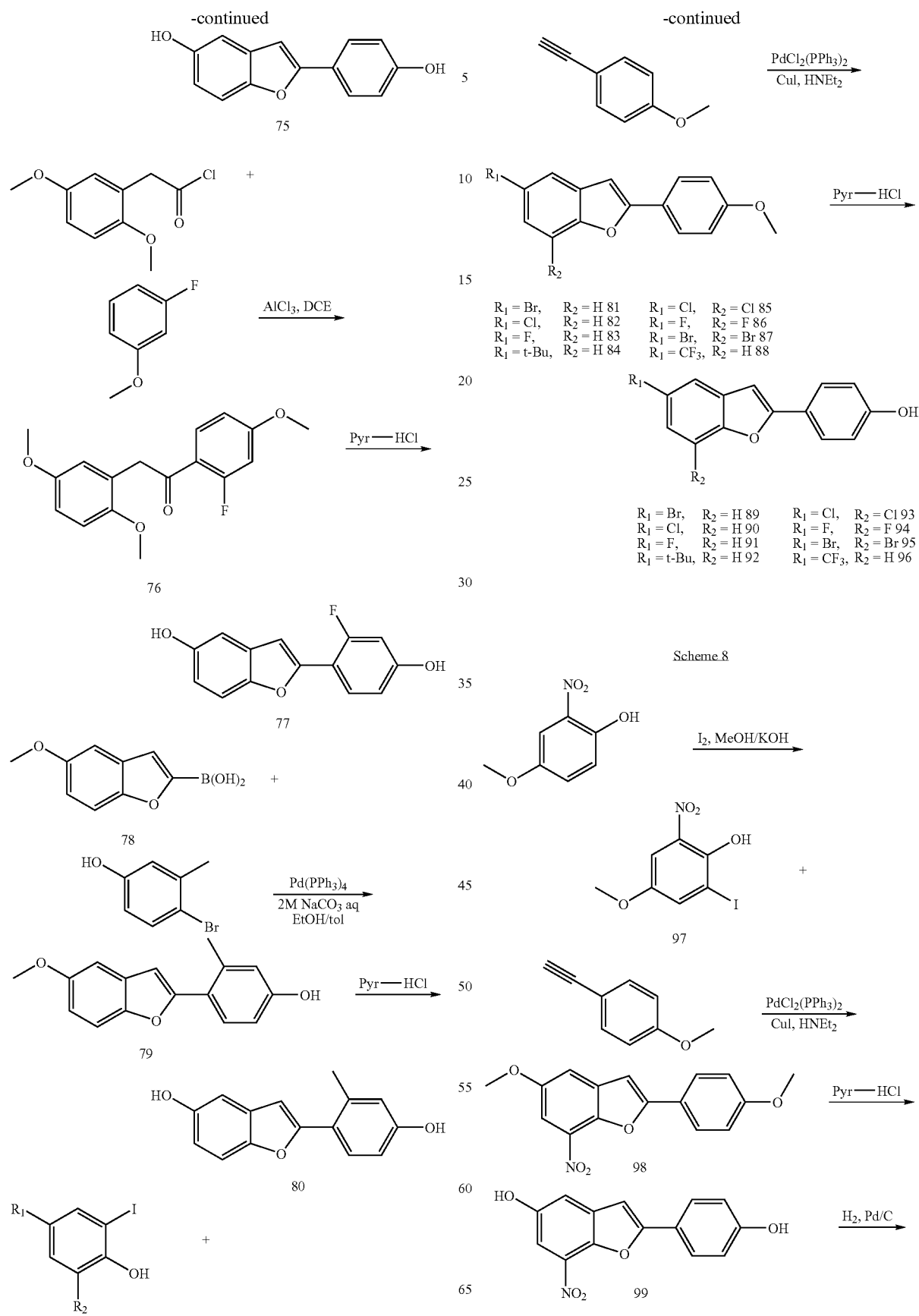

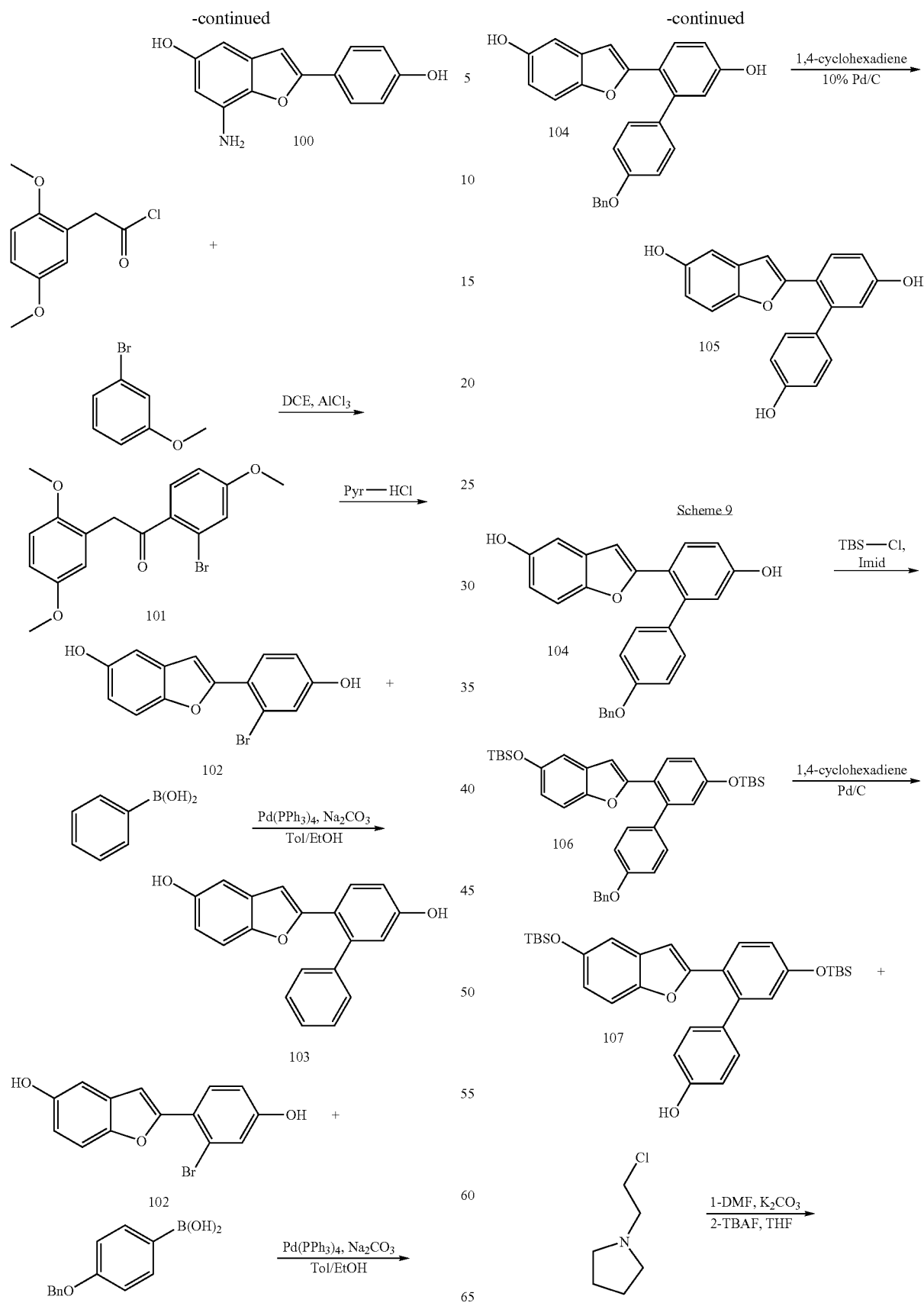

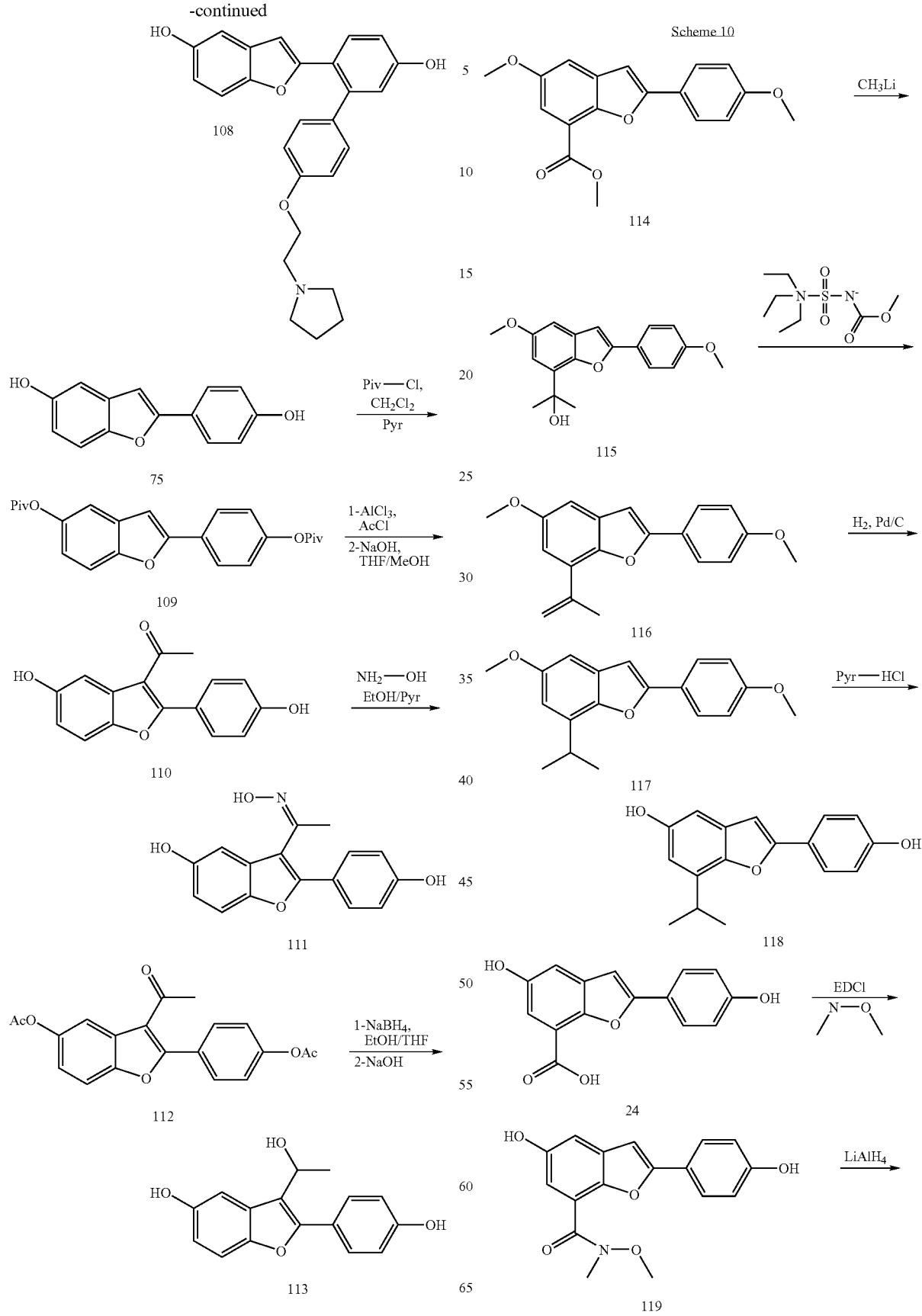

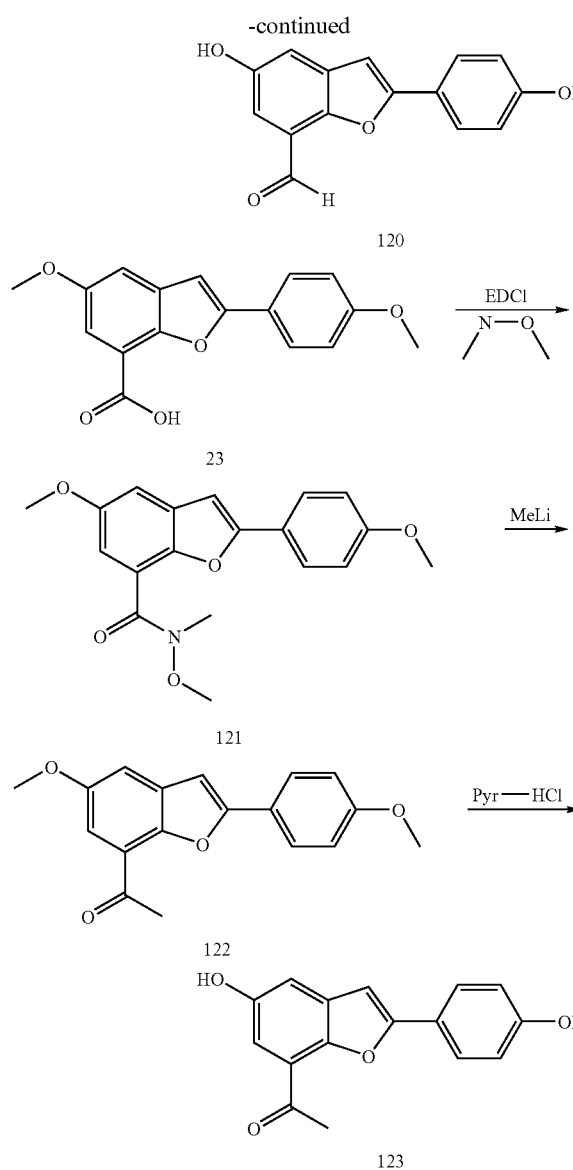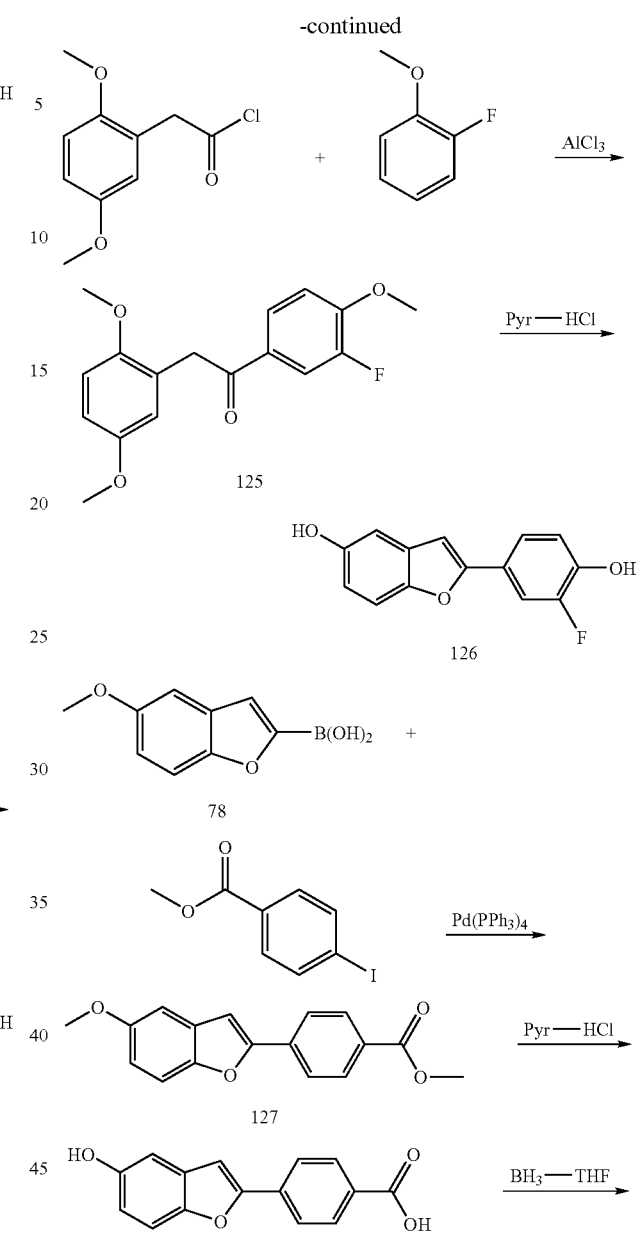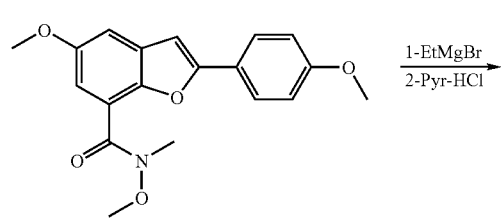
Scheme 11
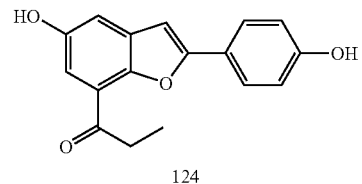
Scheme 12

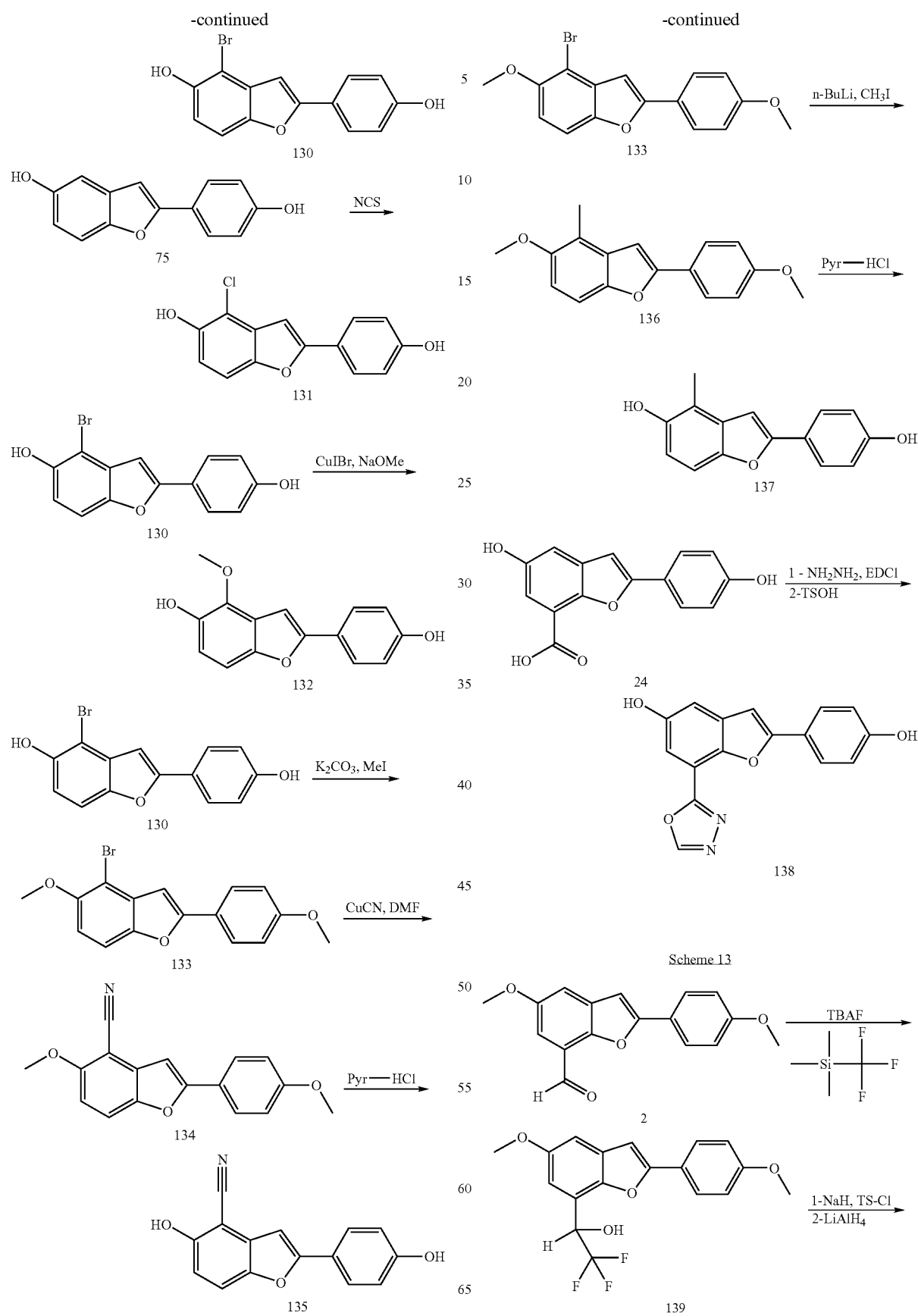

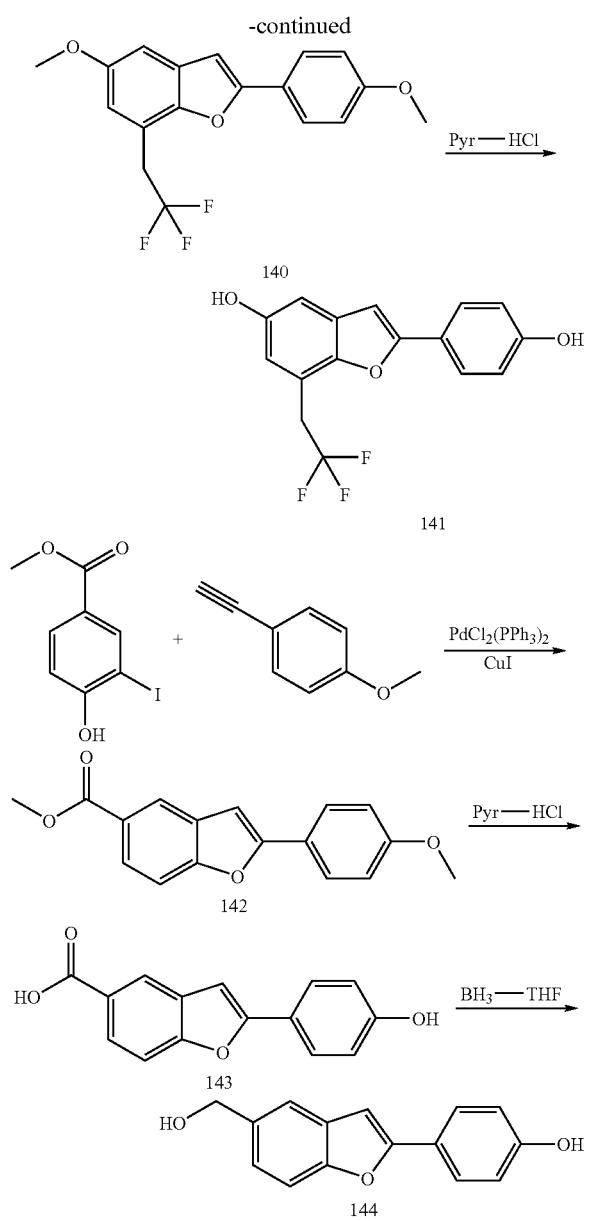

Standard pharmacological test procedures are readily available to determine the activity profile of a given test compound. The following briefly summarizes several representative test procedures and may include data for representative compounds of the invention. All assays, except the radioligand binding assay, can be used to detect estrogen receptor agonist or antagonist activity of compounds. In general, estrogen receptor agonist activity is measured by comparing the activity of the compound to a reference estrogen (e.g. 17β-estradiol, 17α-ethinyl 17β-estradiol, estrone, diethylstilbesterol etc). Estrogen receptor antagonist activity is generally measured by co-treating the test compound with the reference estrogen and comparing the result to that obtained with the reference estrogen alone. Standard pharmacological test procedures for SERMs are also provided in U.S. Pat. Nos. 4,418,068 and 5,998,402 which are hereby incorporated by reference.

Evaluation of Binding Affinities to ERα and ERβ

Representative examples of the invention were evaluated. for their ability to compete with 17β-estradiol for both ERα and ERβ in a conventional radioligand binding assay. This test procedure provides the methodology for one to determine the relative binding affinities for the ERα or ERβ receptors. The procedure used is briefly described below.

Preparation of receptor extracts for characterization of binding selectivity. The ligand binding domains, conveniently defined here as all sequence downstream of the DNA binding domain, were obtained by PCR using full length cDNA as templates and primers that contained appropriate restriction sites for subcloning while maintaining the appropriate reading frame for expression. These templates contained amino acids $M_{250}$-$V_{595}$ of human ERα [Green, et al., Nature 320: 134–9 (1986)] and $M_{214}$-$Q_{530}$ of human ERβ [Ogawa, et al., Biochemical & Biophysical Research Communications 243: 122–6 (1998)]. Human ERβ was cloned into pET15b (Novagen, Madison Wis.) as a Nco1-BamH1 fragment bearing a C-terminal Flag tag. Human ERα was cloned as for human ERβ except that an N-terminal His tag was added. The sequences of all constructs used were verified by complete sequencing of both strands.

BL21(DE3) cells were used to express the human proteins. Typically a 10 mL overnight culture was used to inoculate. a 1 L culture of LB medium containing 100 μg/mL of ampicillin. After incubation overnight at 37° C., IPTG was added to a final concentration of 1 mM and incubation proceeded at 25° C. for 2 hours. Cells were harvested by centrifugation (1500×g), and the pellets washed with and resuspended in 100 mL of 50 mM Tris-Cl (pH 7.4), 150 mM NaCl. Cells were lysed by passing twice through a French press at 12000 psi. The lysate was clarified by centrifugation at 12,00×g for 30 minutes at 4° C. and stored at −70° C.

Evaluation of extracts for specific [³H]estradiol binding. Dulbecco's phosphate. buffered saline (Gibco, 1× final concentration) supplemented with 1 mM EDTA was used as the assay buffer. To optimize the amount of receptor to use in the assay, [³H]-17β-etradiol (New England Nuclear; final concentration=2 nM)±0.6 μM diethlystilbestrol and 100 μL of various dilutions of the E. coli lysate were added to each well of a high binding masked microtiter plate (EG&G Wallac). The final assay volume was 120 μL and the concentration of DMSO was ≦1%. After incubation at room temperature for 5– 18 hours, unbound material was aspirated and the plate washed three times with approximately 300 μL of assay buffer. After washing, 135 μL of scintillation cocktail (Optiphase Supermix, EG&G Wallac) was added to the wells, and the plate was sealed and agitated for at least 5 minutes to mix scintillant with residual wash buffer. Bound radioactivity was evaluated by liquid scintillation counting (EG&G Wallac Microbeta Plus).

After determining. the dilution of each receptor preparation that provided maximum specific binding, the assay was further optimized by estimating the $IC_{50}$ of unlabelled 17β-estradiol using various dilutions of the receptor preparation. A final working dilution for each receptor preparation was chosen for which the $IC_{50}$ of unlabelled 17β-estradiol was 2–4 nM.

Ligand binding competition test procedure. Test compounds were initially solubilized in DMSO and the final concentration of DMSO in the binding assay was <1%. Eight dilutions of each test compound were used as an unlabelled competitor for [³H]-17β-estradiol. Typically, a set of compound dilutions would be tested simultaneously on human ERα and ERβ. The results were plotted as measured DPM vs. concentration of test compound. For dose-response curve fitting, a four parameter logistic model on the transformed, weighted data was fit and the $IC_{50}$ was defined as the concentration of compound decreasing maximum [$^3$H]-estradiol binding by 50%.

Binding affinities for ERα and ERβ (as measured by $IC_{50}$) for representative examples of the invention are shown in Table (1).

TABLE 1

ER binding affinities of representative compounds of the invention

| Example | ER-β $IC_{50}$ (nM) | ER-α $IC_{50}$ (nM) |
|---|---|---|
| 3 | 0.038 | 0.744 |
| 4 | 0.029 | 0.98 |
| 5 | 0.014 | 1.16 |
| 6 | 0.016 | 0.207 |
| 7 | 0.031 | 0.588 |
| 8 | 0.050 | 0.522 |
| 9 | 0.0056 | 0.114 |
| 10 | 0.052 | 0.055 |
| 11 | 0.015 | 0.070 |
| 12 | 0.067 | 0.156 |
| 13 | >5 | >5 |
| 14 | 0.66 | 9.7 |
| 15 | 0.011 | 0.212 |
| 16 | 0.62 | 3.53 |
| 21 | 0.026 | 0.217 |
| 22 | 0.052 | 0.159 |
| 25 | 0.31 | 5.66 |
| 27 | 0.0022 | 0.093 |
| 30 | 0.0018 | 0.043 |
| 32 | 0.038 | 0.186 |
| 35 | 0.010 | 0.039 |
| 36 | 0.083 | 0.93 |
| 37 | 0.043 | 0.577 |
| 38 | 0.043 | 1.35 |
| 39 | 0.028 | 0.504 |
| 43 | 0.010 | 1.056 |
| 43a | 0.008 | 0.625 |
| 48 | 0.0011 | 0.023 |
| 49 | 0.004 | 0.109 |
| 57 | 0.0016 | 0.007 |
| 58 | 0.0016 | 0.015 |
| 59 | 0.075 | 0.606 |
| 60 | 0.17 | 1.21 |
| 61 | 2.69 | >5 |
| 62 | 0.009 | 0.487 |
| 63 | 0.00073 | 0.0075 |
| 64 | 0.009 | 0.161 |
| 65 | 0.080 | 0.849 |
| 67 | 0.0017 | 0.046 |
| 68 | 0.015 | 0.38 |
| 69 | 0.0025 | 0.114 |
| 70 | 0.00034 | 0.021 |
| 71 | 0.074 | 2.42 |
| 72 | 0.151 | 1.78 |
| 73 | 0.032 | 1.65 |
| 73a | 0.042 | 2.959 |
| 75 | 0.006 | 0.178 |
| 77 | 0.006 | 0.089 |
| 80 | 0.0076 | 0.097 |
| 89 | 0.290 | 4.050 |
| 90 | 0.840 | >5 |
| 91 | 0.600 | 7.300 |
| 92 | >5 | >5 |
| 93 | 0.834 | 0.185 |
| 94 | 0.893 | 0.065 |
| 95 | 3.11 | 0.365 |
| 96 | 0.520 | 2.330 |
| 99 | 0.0011 | 0.0017 |
| 100 | 0.26 | 1.78 |
| 102 | 0.002 | 0.031 |
| 103 | 0.0069 | 0.0041 |
| 104 | 0.033 | 0.045 |
| 105 | 0.0081 | 0.0029 |
| 108 | 1.69 | 0.646 |
| 110 | 0.019 | 0.327 |
| 111 | 0.031 | 0.352 |
| 113 | 0.108 | 0.834 |
| 118 | 0.0052 | 0.039 |
| 119 | 0.85 | >5 |
| 120 | 0.007 | 0.263 |
| 121 | 0.006 | 0.103 |
| 122 | 0.0032 | 0.049 |
| 126 | 0.009 | 0.212 |
| 128 | 7.000 | >5 |
| 129 | >5 | >5 |
| 130 | 0.0021 | 0.044 |
| 131 | 0.0026 | 0.041 |
| 132 | 0.034 | 0.422 |
| 135 | 0.008 | 0.264 |
| 136 | 0.014 | 0.452 |
| 138 | 0.648 | >5 |
| 141 | 0.0021 | 0.066 |
| 143 | 1.600 | >5 |
| 144 | >5 | >5 |

The results obtained in the standard pharmacologic test procedure described above demonstrate that the compounds of this invention bind both subtypes of the estrogen receptor. The $IC_{50}$s are generally lower for ERβ, indicating. these compounds are preferentially ERβ selective ligands, but some are still considered active at ERα. compounds of this invention will exhibit a range of activity based, at least partially, on their receptor affinity selectivity profiles. Since the compounds of the invention bind ER-β with higher affinity than ERα, they will be useful in treating or inhibiting diseases than can be modulated via ERβ. Additionally, since each receptor ligand complex is unique and thus its interaction with various coregulatory proteins is unique, compounds of this invention will display different and unpredictable activities depending on cellular context. For example, in some cell-types, it is possible for a compound to behave as an estrogen receptor agonist while in other tissues, an estrogen receptor antagonist. Compounds with such activity have sometimes been referred to as SERMs (Selective Estrogen Receptor Modulators). Unlike many estrogens, however, many of the SERMs do not cause increases in uterine wet weight. These compounds are artiestrogenic in the uterus and can completely antagonize the trophic effects of estrogen receptor agonists in uterine tissue. These compounds, however, act as estrogen receptor agonists in the bone, cardiovascular, and central nervous systems. Due to this tissue selective nature of these compounds, they are useful in treating or inhibiting in a mammal disease states or syndromes which are caused or associated with an estrogen deficiency (in certain tissues such as bone or cardiovascular) or an excess of estrogen (in the uterus or mammary glands). In addition, compounds of this invention also have the potential to behave as estrogen receptor agonists on one receptor type while behaving as estrogen receptor antagonists on the other. For example, it has been demonstrated that compounds can be antagonize the action of 17β-estradiol via ERβ while exhibiting estrogen receptor agonist activity with ERα [Sun, et al., Endocrinology 140: 800–804 (1999)]. Such ERSAA (Estrogen Receptor Selective Agonist Antagonist) activity provides for pharmacologically distinct estrogenic activity within this series of compounds Regulation of Metallothionein II mRNA Estrogens acting through ERβ, but not ERα can upregulate metallothionein II mRNA levels in Saos-2 cells as described by Harris [Endocrinology 142: 645–652 (2001)]. Results from this procedure can be combined with results from the test procedure described below (ERE reporter test procedure) to generate a selectivity profile for compounds of this invention (see also WO 00/37681). Data for representative compounds of the invention are shown in Table (2).

TABLE 2

Regulation of metallothionein-II mRNA in Saos-2 cells

| Compound | Fold Induction at 1 uM |
|---|---|
| 75 | 12 |
| 103 | 9 |

Evaluation of Test Compound Using an ERE-reporter Test Procedure in MCF-7 Breast Cancer Cells Stock solutions of test compounds (usually 0.1 M) are prepared in DMSO and then diluted 10 to 100-fold with DMSO to make working solutions of 1 or 10 mM. The DMSO stocks are stored at either 4° C. (0.1 M) or −20° C. (<0.1M). MCF-7 cells are passaged twice a week with growth medium [D-MEM/F-12 medium containing 10% (v/v) heat-inactivated fetal bovine serum, 1% (v/v) Penicillin-Streptomycin, and 2 mM glutaMax-1]. The cells are maintained in vented flasks at 37° C. inside a 5% $CO_2$/95% humidified air incubator. One day prior to treatment, the cells are plated with growth medium at 25,000 cells/well into 96 well plates and incubated at 37° C. overnight.

The cells are infected for 2 hr at 37° C. with 50 μl/well of a 1:10 dilution of adenovirus 5-ERE-tk-luciferase in experimental medium [phenol red-free D-MEM/F-12 medium containing 10% (v/v) heat-inactived charcoal-stripped fetal bovine serum, 1% (v/v) Penicillin-Streptomycin, 2 mM glutaMax-1, 1 mM sodium pyruvate]. The wells are then washed once with 150 μl of experimental medium. Finally, the cells are treated for 24 hr at 37° C. in replicates of 8 wells/treatment with 150 μl/well of vehicle (<0.1% v/v DMSO) or compound that is diluted >1000-fold into experimental medium.

Initial screening of test compounds is done at a single dose of 1 μM that is tested alone (estrogen receptor agonist mode) or in combination with 0.1 nM 17β-estradiol ($EC_{80}$; estrogen receptor antagonist mode). Each 96 well plate also includes a vehicle control group (0.1% v/v DMSO) and an estrogen receptor agonist control group (either 0.1 or 1 nM 17β-estradiol). Dose-response experiments are performed in either the estrogen receptor agonist and/or estrogen receptor antagonist modes on active compounds in log increases from $10^{-14}$ to $10^{-5}$ M. From these dose-response curves, $EC_{50}$ and $IC_{50}$ values, respectively, are generated. The final well in each treatment group contains 5 μl of $3 \times 10^{-5}$ M ICI-182,780 ($10^{-6}$ M final concentration) as an estrogen receptor antagonist control.

After treatment, the cells are lysed on a shaker for 15 min with 25 μl/well of 1× cell culture lysis reagent (Promega Corporation). The cell lysates (20 μl) are transferred to a 96 well luminometer plate, and luciferase activity is measured in a MicroLumat LB 96 P luminometer (EG & G Berthold) using 100 μl/well of luciferase substrate (Promega Corporation). Prior to the injection of substrate, a 1 second background measurement is made for each well. Following the injection of substrate, luciferase activity is measured for 10 seconds after a 1 second delay. The data are transferred from the luminometer to a Macintosh personal computer and analyzed using the JMP software (SAS institute); this program subtracts the background reading from the luciferase measurement for each well and then determines the mean and standard deviation of each treatment.

The luciferase data are transformed by logarithms, and the Huber M-estimator is used to down-weight the outlying transformed observations. The JMP software is used to analyze the transformed and weighted data for one-way ANOVA (Dunnett's test). The compound treatments are compared to the vehicle control results in the estrogen receptor agonist mode, or the positive estrogen receptors agonist control results (0.1 nM 17β-estradiol) in the estrogen receptor antagonist mode. For the initial single dose experiment, if the compound treatment results are significantly different from the appropriate control ($p<0.05$), then the results are reported as the percent relative to the 17β-estradiol control [i.e., ((compound–vehicle control)/(17β-estradiol control–vehicle control))×100]. The JMP software is also used to determine the $EC_{50}$ and/or $IC_{50}$ values from the non-linear dose-response curves.

Evaluation of Uterotrophic Activity

Uterotrophic activity of a test compound can be measured according to the following standard pharmacological test procedures.

Procedure 1: Sexually immature (18 days of age) Sprague-Dawley rats are obtained from Taconic and provided unrestricted access to a casein-based diet (Purina Mills 5K96C) and water. On day 19, 20 and 21 the rats are dosed subcutaneously with 17α-ethinyl-17β-estradiol (0.06 μg/rat/day), test compound or vehicle (50% DMSO/50% Dulbecco's PBS). To assess estrogen receptor antagonist, compounds are coadministered with 17α-ethinyl-17β-estradiol (0.06 μg/rat/day). There are six rats/group and they are euthanized approximately 24 hours after the last injection by $CO_2$ asphyxiation and pneumothorax. Uteri are removed and weighed after trimming associated fat and expressing any internal fluid. A tissue sample can also be snap frozen for analysis of gene expression (e.g. complement factor 3 mRNA).

Evaluation of Osteoporosis and Lipid Modulation (Cardioprotection)

Female Sprague-Dawley rats, ovariectomized or sham operated, are obtained 1 day after surgery from Taconic Farms (weight range 240–275 g). They are housed 3 or 4 rats/cage in a room on a 12/12 (light/dark) schedule and provided with food (Purina 5K96C rat chow) and water ad libitum. Treatment for all studies begin 1 day after arrival and rats are dosed 7 days per week as indicated for 6 weeks. A group of age matched sham operated rats not receiving any treatment serve as an intact, estrogen replete control group for each study.

All test compounds are prepared in a vehicle of 50% DMSO (J T Baker, Phillipsburg, N.J.)/1× Dulbecco's phosphate saline (GibcoBRL, Grand Island N.Y.) at defined concentrations so that the treatment volume is 0.1 mL/100 g body weight. 17β-estradiol is dissolved in corn oil (20 μg/mL) and delivered subcutaneously, 0.1 mL/rat. All dosages are adjusted at three week intervals according to group mean body weight measurements, and given subcutaneously.

Five weeks after the initiation of treatment and one week prior to the termination of the study, each rat is evaluated for bone mineral density (BMD). The total and trabecular density of the proximal tibia are evaluated in anesthetized rats using an XCT-960M (pQCT; Stratec Medizintechnik, Pforzheim, Germany). The measurements are performed as follows: Fifteen minutes prior to scanning, each rat is anesthetized with an intraperitoneal injection of 45 mg/kg ketamine, 8.5 mg/kg xylazine, and 1.5 mg/kg acepromazine.

The right hind limb is passed through a polycarbonate tube with a diameter of 25 mm and taped to an acrylic frame with the ankle joint at a 90° angle and the knee joint at 180°. The polycarbonate tube is affixed to a sliding platform that maintains it perpendicular to the aperture of the pQCT. The platform is adjusted so that the distal end of the femur and the proximal end of the tibia is in the scanning field. A two dimensional scout view is run for a length of 10 mm and a line resolution of 0.2 mm. After the scout view is displayed on the monitor, the proximal end of the tibia is located. The pQCT scan is initiated 3.4 mm distal from this point. The pQCT scan is 1 mm thick, has a voxel (three dimensional pixel) size of 0.140 mm, and consists of 145 projections through the slice.

After the pQCT scan is completed, the image is displayed on the monitor. A region of interest including the tibia but excluding the fibula is outlined. The soft tissue is mathematically removed using an iterative algorithm. The density of the remaining bone (total density) is reported in $mg/cm^3$. The outer 55% of the bone is mathematically peeled away in a concentric spiral. The density of the remaining bone (Trabecular density) is reported in $mg/cm^3$.

One week after BMD evaluation the rats are euthanized by $CO_2$ asphyxiation and pneumothorax, and blood is collected for cholesterol determination. The uteri are also removed and the weighed after trimming associated fat and expressing any luminal fluid. Total cholesterol is determined using a Boehringer-Mannheim Hitachi 911 clinical analyzer using the Cholesterol/HP kit. Statistics are compared using one-way analysis of variance with Dunnets test.

Evaluation of Antioxidant Activity

Porcine aortas are obtained from an abattoir, washed, transported in chilled PBS, and aortic endothelial cells are harvested. To harvest the cells, the intercostal vessels of the aorta are tied off and one end of the aorta clamped. Fresh, sterile filtered, 0.2% collagenase (Sigma Type I) is placed in the vessel and the other end of the vessel then clamped to form a closed system. The aorta is incubated at 37° C. for 15–20 minutes, after which the collagenase solution is collected and centrifuged for 5 minutes at 2000×g. Each pellet is suspended in 7 mL of endothelial cell culture medium consisting of phenol red free DMEM/Hams F12 media supplemented with charcoal stripped FBS (5%), NuSerum (5%), L-glutamine (4 mM), penicillin-streptomycin (1000 U/ml, 1001 µg/ml) and gentamycin (75 µg/ml), seeded in 100 mm petri dish and incubated at 37° C. in 5% $CO_2$. After 20 minutes, the cells are rinsed with PBS and fresh medium added, this was repeated again at 24 hours. The cells are confluent after approximately 1 week. The endothelial cells are routinely fed twice a week and, when confluent, trypsinized and seeded at a, 1:7 ratio. Cell mediated oxidation of 12.5 µg/mL LDL is allowed to proceed in the presence of the compound to be evaluated (5 µM) for 4 hours at 37° C. Results are expressed as the percent inhibition of the oxidative process as measured by the TBARS (thiobarbituric acid reactive substances) method for analysis of free aldehydes [Yagi, Biochemical Medicine 15: 212–6 (1976)].

Rat Hot Flush Test Procedure

The effect of test compounds on hot flushes can be evaluated in a standard pharmacological test procedure which measures the ability of a test compound to blunt the increase in tail skin temperature which occurs as morphine-addicted rats are acutely withdrawn from the drug using naloxone [Merchenthaler, et al., Maturitas 30: 307–16 (1998)]. It can also be used to detect estrogen receptor antagonist activity by co-dosing test compound with the reference estrogen.

Evaluation of Vasomotor Function in Isolated Rat Aortic Rings

Sprague-Dawley rats (240–260 grams) are divided into 4 groups:
1. Normal non-ovariectomized (intact)
2. Ovariectomized (ovex) vehicle treated
3. Ovariectomized-17β-estradiol treated (1 kg/day)
4. Ovariectomized animals treated with test compound (Various doses)

Animals are ovariectomized approximately 3 weeks prior to treatment. Each animal receives either 17-β estradiol sulfate (1 mg/kg/day) or test compound suspended in distilled, deionized water with 1% tween-80 by gastric gavage. Vehicle treated animals received an appropriate volume of the vehicle used in the drug treated groups.

Animals are euthanized by $CO_2$ inhalation and exsanguination. Thoracic aortae are rapidly removed and placed in 37° C. physiological solution with the following composition (mM): NaCl (54.7), KCl (5.0), $NaHCO_3$ (25.0), $MgCl_2$ $2H_2O$ (2.5), D-glucose (11.8) and $CaCl_2$ (0.2) gassed with $CO_2$—$O_2$, 95%/5% for a final pH of 7.4. The advantitia is removed from the outer surface and the vessel is cut into 2–3 mm wide rings. Rings are suspended in a 10 mL tissue bath with one end attached to the bottom of the bath and the other to a force transducer. A resting tension of 1 gram is placed on the rings. Rings are equilibrated for 1 hour, signals are acquired and analyzed.

After equilibration, the rings are exposed to increasing concentrations of phenylephrine ($10^{-8}$ to $10^{-4}$ M) and the tension recorded. Baths are then rinsed 3 times with fresh buffer. After washout, 200 mM L-NAME is added to the tissue bath and equilibrated for 30 minutes. The phenylephrine concentration response curve is then repeated.

Evaluation of Cardioprotective Activity

Apolipoprotein E-deficient. C57/B1J (apo E KO) mice are obtained from Taconic Farms. All animal procedures are performed under strict compliance to IACUC guidelines. Ovariectomized female apo E KO mice, 4–7 weeks of age, are housed in shoe-box cages and were allowed free access to food and water. The animals are randomized by weight into groups (n=12–15 mice per group). The animals are dosed with test compounds or estrogen (17β-estradiol sulfate at 1 mg/kg/day) in the diet using a Precise-dosing Protocol, where the amount of diet consumed is measured weekly, and the dose adjusted accordingly, based on animal weight. The diet used is a Western-style diet (57U5) that is prepared by Purina and contains 0.50% cholesterol, 20% lard and 25 IU/KG Vitamin E. The animals are dosed/fed using this paradigm for a period of 12 weeks. Control animals are fed the Western-style diet and receive no compound. At the end of the study period, the animals are as samples obtained. The hearts are perfused in situ, first with saline and then with neutral buffered 10% formalin solution.

For the determination of plasma lipids and lipoproteins, total cholesterol and triglycerides are determined using enzymatic methods with commercially available kits from Boehringer Mannheim and Wako Biochemicals, respectively and analyzed using the Boehringer Mannheim Hitachii 911 Analyzer. Separation and quantification of plasma lipoproteins were performed using FPLC size fractionation. Briefly, 50–100 mL of serum is filtered and injected into Superose 12 and Superose 6 columns connected in series and eluted at a constant flow rate with 1 mM sodium EDTA and 0.15M NaCl. Areas of each curve representing VLDL, LDL and HDL are integrated using Waters Millennium™ software, and each lipoprotein fraction is quantified by multiplying the Total Cholesterol value by the relative percent area of each respective chromatogram peak.

For the quantification of aortic atherosclerosis, the aortas are carefully isolated and placed in formalin fixative for 48–72 hours before handling. Atherosclerotic lesions are identified using Oil Red O staining. The vessels are briefly destained, and then imaged using a Nikon SMU800 microscope fitted with a Sony 3CCD video camera system in concert with IMAQ Configuration Utility (National Instrument) as the image capturing software. The lesions are quantified en face along the aortic arch using a custom threshold utility software package (Coleman Technologies). Automated lesion assessment is performed on the vessels using the threshold function of the program, specifically on the region contained within the aortic arch from the proximal edge of the brachio-cephalic trunk to the distal edge of the left subclavian artery. Aortic atherosclerosis data are expressed as percent lesion involvement strictly within this defined luminal area.

Evaluation of Cognition Enhancement

Ovariectomized rats (n=50) are habituated to an 8-arm radial arm maze for 10-min periods on each of 5 consecutive days. Animals are water-deprived prior to habituation and testing. A 100 µL aliquot of water placed at the ends of each arm serves as reinforcement. Acquisition of a win-shift task in the radial arm maze is accomplished by allowing the animal to have access to one baited arm. After drinking, the animal exits the arm and re-enters the central compartment, where it now has access to the previously visited arm or to a novel arm. A correct response is recorded when the animal chooses to enter a novel arm. Each animal is given 5 trials per day for 3 days. After the last acquisition trial, the animals are assigned to one of the following 4 groups:
 1. Negative controls: injected with 10% DMSO/sesame oil vehicle once daily for 6 days (1 mL/kg, SC)
 2. Positive controls: injected with 17β-estradiol benzoate for 2 days and tested 4 days after the second injection (17β-estradiol benzoate at 10 µg/0.1 mL per rat)
 3. Estradiol: 17β-estradiol will be injected daily for 6 days (20 µg/kg, SC)
 4. Test compound: injected daily for 6 days (doses vary).

All injections will begin after testing on the last day of acquisition. The last injection for groups 1, 3, and 4 will take place 2 hours before testing for working memory.

The test for working memory is a delayed non-matching-to-sample task (DNMS) utilizing delays of 15, 30, or 60 seconds. This task is a variation of the acquisition task in Which the rat is placed in the central arena and allowed to enter one arm as before. A second arm is opened once the rat traverses halfway down the first arm, and again the rat is required to choose this arm. When it has traveled halfway down this second arm, both doors are closed and the delay is instituted. Once the delay has expired, both of the original two doors, and a third novel door are opened simultaneously. A correct response is recorded when the animal travels halfway down the third, novel arm. An incorrect response is recorded when the animal travels halfway down either the first or second arms. Each animal will receive 5 trials at each of the three delay intervals for a total of 15 trials per subject.

Evaluation of Effect on Pleurisy

The ability to reduce the symptoms of experimentally-induced pleurisy in rats can be evaluated according to the procedure of Cuzzocrea [Endocrinology 141: 1455–63 (2000)].

Evaluation of Protection Against Glutamate-induced Cytotoxicity (Neuroprotection)

The neuroprotective activity of compounds of this invention can be evaluated in an in vitro standard pharmacological test procedure using glutamate challenge [Zaulyanov, et al., Cellular & Molecular Neurobiology 19; 705–18 (1999); Prokai, et al., Journal of Medicinal Chemistry 44: 110–4 (2001)].

Evaluation in the Mammary End Bud Test Procedure

Estrogens are required for full ductal elongation and branching of the mammary ducts, and the subsequent development of lobulo-alveolar end buds under the influence of progesterone. In this test procedure, the mammotrophic activity of selected compounds of the invention was evaluated according to the following standard pharmacological test procedure. Twenty-eight day old Sprague-Dawley rats (Taconic Farms, Germantown, N.Y.) were ovariectomized and rested for nine days. Animals were housed under a 12-hour light/dark cycle and fed a casein-based Purina Laboratory Rodent Diet 5K96 (Purina, Richmond, Tenn.) and allowed free access to water. Rats were then dosed subcutaneously for six days with vehicle (50% DMSO (J T Baker, Phillipsburg, N.J.)/50% 1× Dulbecco's Phosphate buffered saline (GibcoBRL, Grand Island, N.Y.), 17β-estradiol (0.1 mg/kg) or test compound (20 mg/kg). For the final three days, rats were also dosed subcutaneously with progesterone (30 mg/kg). On the seventh day, rats were euthanised and a mammary fat pad excised. This fat pad was analyzed for casein kinase II mRNA as a marker of end bud proliferation. Casine kinase II mRNA was analyzed by real-time RT-PCR. Briefly, RNA was isolated following Trizol (GibcoBRL, Grand Island, N.Y.) according to the manufacture's directions, Samples were treated with DNAse I using DNA-free kit (Ambion), and casein kinase II mRNA levels were measured by real-time RT-PCR using the Taqman Gold procedure (PE Applied Biosystems). A total of 50 ng of RNA was analyzed in triplicate using casein kinase II specific primer pair (5' primer, CACACGGATGGCGCATACT (SEQ. ID NO:1); 3' primer, CTCGGGATGCACCATGAAG (SEQ. ID NO:2)) and customized probe (TAMRA-CG-GCACTGGTTTCCCTCACATGCT-FAM) (SEQ. ID NO:3). Casein kinase II mRNA levels were normalized to 18s ribosomal RNA contained within each sample reaction using primers and probe supplied by PE Applied Biosystems.

Evaluation in the HLA Rat Standard Pharmacological Test Procedure for Inflammatory Bowel Disease Representative compounds of the invention can be evaluated in the HLA rat standard pharmacological test procedure which emulates inflammatory bowel disease in humans. The following briefly describes the procedure used and results obtained. Male HLA-B27 rats were obtained from Taconic and provided unrestricted access to food (PMI Lab diet-5001) and water. Stool quality was observed daily and graded according to the following scale: Diarrhea=3; soft stool=2; normal stool=1. At the end of the study, serum was collected and stored at −70° C. A section of colon was prepared for histological analysis and an additional segment was analyzed for myeloperoxidase activity.

Histological Analysis. Colonic tissue was immersed in 10% neutral buffered formalin. Each specimen of colon was separated into four samples for evaluation. The formalin-fixed tissues were processed in a Tissue Tek vacuum infiltration processor (Miles, Inc; West Haven, Conn.) for paraffin embedding. The samples were sectioned at 5 μm and then stained with hematoxylin and eosin (H&E) for blinded histologic evaluations using a scale modified after Boughton-Smith. After the scores were completed the samples were unblinded, and data were tabulated and analyzed by ANOVA linear modeling with multiple mean comparisons. Sections of colonic tissue were evaluated for several disease indicators and given relative scores.

Evaluation in Two Models of Arthritis

Lewis rat assay of adjuvant-induced arthritis. Sixty, female, 12 weeks old, Lewis rats are housed according to standard facility operating procedures. They receive a standard regimen of food and water ad libitum. Each animal is identified by a cage card indicating the project group and animal number. Each rat number is marked by indelible ink marker on the tail. At least 10–21 days before study they are anesthetized and ovariectomized by standard aseptic surgical techniques.

Freund's Adjuvant-Complete (Sigma Immuno Chemicals, St. Louis, Mo.) is used to induce arthritis, each mL containing 1 mg *Mycobacterium tuberculosis* heat killed and dried, 0.85 mL mineral oil and 0.15 mL mannide monooleate Lot No. 084H8800.

The following are examples of two test procedures. Inhibition test procedure: Thirty rats are injected intradermally with 0.1 mL of Freund's Adjuvant-Complete at the base of the tail. The animals are randomized to four groups, each group containing six rats. Each day, the groups receive vehicle (50% DMSO (J T Baker, Phillipsburg, N.J.)/1× Dulbecco's phosphate saline (GibcoBRL, Grand Island, N.Y.)) or test compound (administered subcutaneously). All rats began treatment on Day 1. Treatment test procedure: Thirty rats are injected intradermally with 0.1 mL of Freund's Adjuvant-Complete at the base of the tail. The animals are randomized to four groups, each group containing six rats; Each day, the groups receive vehicle (50% DMSO (J T Baker, Phillipsburg, N.J.)/1× Dulbecco's phosphate saline (GibcoBRL, Grand Island N.Y.)) or test compound (administered subcutaneously). All rats began treatment on Day 8 after adjuvant injection. Statistical analysis is performed using Abacus Concepts Super ANOVA. (Abacus Concepts, Inc., Berkeley, Calif.). All of the parameters of interest are subjected to Analysis of Variance with Duncan's new multiple range post hoc testing between groups. Data are expressed throughout as mean±standard deviation (SD), and differences were deemed significant if $p<0.05$.

The degree of arthritis severity is monitored daily in terms of the following disease indices: Hindpaw erythema, hindpaw swelling, tenderness of the joints, and movements and posture. An integer scale of 0 to 3 is used to quantify the level of erythema (0=normal paw, 1=mild erythema, 2=moderate erythema, 3=severe erythema) and swelling (0=normal paw, 1=mild swelling, 2=moderate swelling, 3=severe swelling of the hind paw). The maximal score per day is 12.

At the end of the study the rats are euthanized with $CO_2$, hindlimbs removed at necropsy and fixed in 10% buffered formalin, and the tarsal joints decalcified and embedded in paraffin. Histologic sections are stained with Hematoxylin and Eosin or Saffranin O—Fast Green stain.

Slides are coded so that the examiner is blinded to the treatment groups. Synovial tissue from tarsal joints is evaluated based on synovial hyperplasia, inflammatory cell infiltration, and pannus formation [Poole and Coombs, International Archives of Allergy & Applied Immunology 54: 97–113 (1977)] as outlined below.

| Category | Grade |
| --- | --- |
| 1. Synovial lining cells | |
| a. No change | 0 |
| b. Cells enlarged, slightly thickened | 1 |
| c. Cells enlarged, increase in numbers, moderately thickened. No villus present | 2 |
| d. Cells enlarged, thickened. Villus present | 3 |
| 2. Fibroplasia | |
| a. No change | 0 |
| b. Fibroplasia present under lining cells | 1 |
| c. Small areas of areolar tissue replaced by fibrous tissue | 2 |
| d. Replacement of areolar tissue by fibrous tissue | 3 |
| 3. Inflammatory cells | |
| a. Occasionally seen, scattered throughout selection | 0 |
| b. Cells present in small numbers in or just under lining cell layer and/or around blood vessels. | 1 |
| c. Small focal collection of cells may be present | 2 |
| d. Large numbers of cells present in capsule and in or under lining cell layers. Large foci often seen. | 3 |
| 4. Pannus | |
| a. Not detectable | 0 |
| b. Detectable | 1 |

In addition, articular cartilage and bone is evaluated using Mankin's histological grading system [Mankin, et al., Journal of Bone & Joint Surgery—American Volume 53: 523–37 (1971)] as shown below.

| Category | Grade |
| --- | --- |
| 1. Structure | |
| a. Normal | 0 |
| b. Surface irregularity | 1 |
| c. Pannus and surface irregularity | 2 |
| d. Clefts to transitional zone | 3 |
| e. Clefts to radial zone | 4 |
| f. Clefts to calcified zone | 5 |
| g. Complete disorganization | 6 |
| 2. Cells | |
| a. Normal | 0 |
| b. Diffuse hypercellularity | 1 |
| c. Cloning | 2 |
| d. Hypocellularity | 3 |
| 3. Safranin-O staining | |
| a. Normal | 0 |
| b. Slight reduction | 1 |
| c. Modest reduction | 2 |
| d. Severe reduction | 3 |
| e. No dye noted | 4 |
| 4. Tidemark integrity | |
| a. Intact | 0 |
| b. Crossed by blood vessels | 1 |

Evaluation in the HLA-B27 Rat model of arthritis. Representative compounds of the invention can also be evaluated in the HLA-B27 rat standard pharmacological test procedure which emulates arthritis in humans. The following briefly describes the procedure used and results obtained. Male HLA-B27 rats can be obtained from Taconic and provided unrestricted access to a food (PMI Lab diet 5001) and water. Joint scores and histology are evaluated as described above for the Lewis rat model of adjuvant-induced arthritis.

Evaluation in in vivo Models of Carcinogeneisis

The ability of compounds of this invention to treat and inhibit various malignancies or hyperprolific disorders can be evaluated in standard pharmacologica test procedures that are readily available in the literature, and include the following two procedures.

Breast cancer. Athymic nu/nu (nude) mice are obtained ovaectormized from Charles River Laboratories (Wilmington, Mass.). One day prior to tumor cell injection, animals are implanted. with time-release pellets containing 0.36–1.7 mg 17β-stradiol (60 or 90 day release, Innovative Research of America, Sarasota, Fla.) or a placebo. The pellet is introduced subcutaneously into the intrascapular region using a 10-gauge precision trochar. Subsequently, mice are injected subcutaneously into the breast tissue with either $1 \times 10^7$ MCF-7 cells or $1 \times 10^7$ BG-1 cells. The cells are mixed with an equal volume of matrigel, a basement membrane matrix-preparation to enhance tumor establishment. Test compounds can be evaluated either by. dosing one day after tumor cell implantation (inhibition regimen) or after tumors have reached a certain size (treatment regimen). Compounds are administered either intraperitoneally or orally in a vehicle of 1% tween-80 in saline each day. Tumor size is evaluated every three or seven days.

Colon cancer. The ability to treat or inhibit colon cancer can be evaluated in the test procedure of Smirnoff [Oncology Research 11: 255–64 (1999)].

Evaluation of Neuroprotection in Two in vivo Test Procedures

Transient global ischemia in the Mongolian gerbil. The effect of test compounds on preventing or treating brain injury in response to oxygen deprivation/reperfusion can be measured using the following test procedure.

Female Mongolian gerbils (60–80 g; Charles River Laboratories, Kingston, N.Y.) were housed in the Wyeth-Ayerst animal care facility (AAALAC certified) with a 12-hour light, 12-hour dark photoperiod and free access to tap water and a low-estrogen casein diet (Purina; Richmond, Ind.). After acclimation (3–5 days), gerbils were anesthetized with isoflurane (2–3% mixture with $O_2$), ovariectomized (Day 0). Beginning the following morning (Day 1), gerbils were treated subcutaneously each day with either vehicle (10% ETOH/corn oil), 17β-estradiol (1 mg/kg, sc) or an experimental compound. On Day 6, gerbils (n=4–5/group) were anesthetized with isoflurane, the common carotid arteries visualized via a mid-line neck incision and both arteries simultaneously occluded for 5 minutes with non-traumatic micro aneurysm clips. After occlusion, the dips were removed to allow cerebral reperfusion and the neck incision closed with wound clips. All animals were fasted overnight prior to the global ischemia surgery, a step that facilitates consistent ischemic injury. On Day 12, gerbils were exposed to a lethal dose of $CO_2$, and the brains frozen on dry ice and stored at $-80°$ C. The animal protocols used for these studies were reviewed and approved by the Radnor/Collegeville Animal Care and Use Committee (RACUC/CACUC) at Wyeth-Ayerst Research.

The degree of neuronal protection was evaluated by in situ hybridization analysis of neurogranin mRNA. Briefly, 20 μm coronal cryostat sections were collected on gelatin-coated slides, dried and stored at $-80°$ C. At the time of processing, the desiccated slide boxes were warmed to room temperature, the slides postfixed in 4% paraformaldehyde, treated with acetic anhydride and then delipidated and dehydrated with chloroform and ethanol. Processed section-mounted slides were then hybridized with 200 μl ($6 \times 10^6$ DPM/slide) of an antisense or sense (control) riboprobe for Neurogranin ($^{35}$S-UTP-labeled NG-241; bases 99–340) in a 50% formamide hybridization mix and incubated overnight at $55°$ C. in a humidified slide chamber without coverslipping. The following morning, the slides were collected in racks, immersed in 2×SSC (0.3 M NaCl, 0.03 M sodium citrate; pH 7.0)/10 mM DTT, treated with RNase A (20 μg/ml) and washed (2×30 min) at $67°$ C. in 0.1×SSC to remove nonspecific label. After dehydration, the slides were opposed to BioMax (BMR-1; Kodak) X-ray film overnight.

The level of neurogranin hybridization signal was used to quantitatively assess the degree of neuronal loss in the CA1 region after injury and to evaluate the efficacy of 17β-estradiol and experimental compounds. Neurogranin mRNA was selected for these studies because it is highly expressed in the hippocampal neurons including CA1, but absent in glia and other cell types present in this brain region. Therefore, measurement of the amount of neurogranin mRNA present represents surviving neurons. Relative optical density measurements of neurogranin hybridization signal were obtained from film autoradiograms with a computer based image analysis system (C-Imaging Inc., Pittsburgh, Pa.). The results from 6 sections (40 μm apart) per animal were averaged and statistically evaluated. Numerical values are reported as the mean±SEM. One-way analysis of variance was used to test for differences in the level of neurogranin mRNA and all statements of non-difference in the results section imply that P>0.05. Middle cerebral artery occlusion in mice. Neuroprotection can be evaluated according to the test procedures described by Dubal [see, Dubal, et al., Proceedings. of the National Academy of Sciences of the United States of America 98: 1952–1957 (2001), Dubal, et al., Journal of Neuroscience 19: 6385–6393 (1999)].

Ovulation Inhibition Standard Pharmacological Test Procedure

The test procedure is used to determine whether test compounds can inhibit or change the timing of ovulation. It can also be used to determine the number of oocytes ovulated [Lundeen, et al., J Steroid Biochem Mol Biol 78: 137–143 (2001)].

Based on the results obtained in the standard pharmacological test procedures, the compounds of this invention are estrogen receptor modulators useful in the treatment or inhibition of conditions, disorders, or disease states that are at least partially mediated by an estrogen deficiency or excess, or which may be treated or inhibited through the use of an estrogenic agent. The compounds of this invention are particularly useful in treating a peri-menopausal, menopausal, or postmenopausal patient in which the levels of endogenous estrogens produced are greatly diminished. Menopause is generally defined as the last natural menstrual period and is characterized by the cessation of ovarian function, leading to the substantial diminution of circulating estrogen in the bloodstream. As used herein, menopause also includes conditions of decreased estrogen production that may be surgically, chemically, or be caused by a disease state which leads to premature diminution or cessation of ovarian function.

The compounds of this invention are also useful in inhibiting or treating other effects of estrogen deprivation including, hot flushes, vaginal or vulvar atrophy, atrophic vaginitis, vaginal dryness, pruritus, dyspareunia, dysuria, frequent urination, urinary incontinence, urinary tract infections. Other reproductive tract uses include the treatment or inhibition of dysfunctional uterine bleeding. The compounds are also useful in treating or inhibiting endometriosis.

The compounds of this invention are also active in the brain and are therefore useful for inhibiting or treating Alzheimer's disease, cognitive decline, decreased libido, senile dementia, neurodegenerative disorders, depression, anxiety, insomnia, schizophrenia, and infertility. The compounds of this invention are also useful in treating or inhibiting benign or malignant abnormal tissue growth including, glomerulosclerosis, prostatic hypertrophy, uterine leiomyomas, breast cancer, scleroderma, fibromatosis, endometrial cancer, polycystic ovary syndrome, endometrial polyps, benign breast disease, adenomyosis, ovarian cancer, melanoma, prostate cancer, cancers of the colon, CNS cancers, such as glioma or astioblastomia.

The compounds of this invention are cardioprotective and are antioxidants, and are useful in lowering cholesterol, triglycerides, Lp(a), and LDL levels; inhibiting or treating hypercholesteremia, hyperlipidemia, cardiovascular disease, atherosclerosis, peripheral vascular disease, restenosis, and vasospasm, and inhibiting vascular wall damage from cellular events leading toward immune mediated vascular damage.

The compounds of this invention are also useful in treating disorders associated with inflammation or autoimmune diseases, including inflammatory bowel disease (Crohn's disease, ulcerative colitis, indeterminate colitis), arthritis (rheumatoid arthritis, spondyloarthropathies, osteoarthritis), pleurisy, ischemia/reperfusion injury (e.g. stroke, transplant rejection, myocardial infarction, etc.), asthma, giant cell arteritis, prostatitis interstitial cystitis, uveitis, psoriasis, multiple sclerosis, systemic lupus erythematosus and sepsis.

The compounds of this invention are also useful in treating or inhibiting ocular disorders including cataracts, uveitis, and macular degeneration and in treating skin conditions such as aging, alopecia, and acne.

The compounds of this invention are also useful in treating or inhibiting metabolic disorders such as type-II diabetes, of lipid metabolism, appetite (e.g. anorexia nervosa and bulimia).

Compounds in this invention are also useful in treating or inhibiting bleeding disorders such as hereditary hemorrhagic telangiectasia, dysfunctional uterine bleeding, and combating hemorrhagic shock.

The compounds of this invention are useful in disease states where amenorrhea is advantageous, such as leukemia, endometrial ablations, chronic renal or hepatic disease or coagulation diseases or disorders.

The compounds of this invention can be used as a contraceptive agent, particularly when combined with a progestin.

When administered for the treatment or inhibition of a particular disease state or disorder, it is understood that the effective dosage may vary depending upon the particular compound utilized, the mode of administration, the condition, and severity thereof, of the condition being treated, as well as the various physical factors related to the individual being treated. Effective administration of the compounds of this invention may be given at an oral dose of from about, 0.1 mg/day to about 1,000 mg/day. Preferably, administration will be from about 10 mg/day to about 600 mg/day more preferably from about 50 mg/day to about 600 mg/day in a single dose or in two or more divided doses. The projected daily dosages are expected to vary with route of administration.

Such doses may be administered in any manner useful in directing the active compounds herein to the recipients bloodstream, including orally, via implants, parentally (including intravenous, intraperitoneal, intraarticularly and subcutaneous injections), rectally, intranasally, topically, ocularly (via eye drops), vaginally, and transdermally.

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidol silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or a fruit juice, containing appropriate solubilizers or emulsifiers as needed.

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to inhibit the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

The preparation of representative examples of this invention is described below. Nomenclature for compounds of this invention were obtained by inputting the structure into ChemDraw5® or ChemDraw Ultra® and naming with the "convert structure to name" tool.

Synthesis of Compounds from Scheme 1

2-Hydroxy-3-iodo-5-methoxy-benzaldehyde 1

To a solution of 2-hydroxy-5-methoxy-benzaldehyde (15.97 g, 104.9 mmole) in 375 mL dichloromethane at −15° C. was added tetraethylammonium diacetoxyiodate (48.06 g, 128.1 mmole) over 15 minutes. After stirring overnight, an additional amount of tetraethylammonium diacetoxyiodate (46.93 g, 125.1 mmole) was added over 15 minutes. The reaction was stirred for an additional 12 hours, concentrated, and added to 2N HCl. The mixture was extracted into ethyl acetate and the combined organic phases were washed with saturated sodium bicarbonate, water, brine, and dried with magnesium sulfate. The organic phases were concentrated in vacuo and the residue was loaded on to silica gel and chromatographed with silica gel (hexanes:ethyl acetate, 9:1) to afford 3.47 g (11.9%) of iodide as a yellow solid: Mp=103–105° C.; $^1$H NMR (DMSO-$d_6$) δ 11.3 (s, 1H), 9.73 (s, 1H), 7.60 (d, 1 H, J=3.0 Hz,), 7.07 (d, 1 H, J=3.1 Hz), 3.83 (s, 3H).

5-Methoxy-2-(4-methoxy-phenyl)-benzofluran-7-carbaldehyde 2

A solution of iodo benzaldehyde 1 (2.11 g, 7.59 mmole), 4-ethynyl-1-methoxy-benzene (1.20 g, 9.11 mmole), dichlorobis(triphenylphosphine)palladium(II) (0.501 g, 0.714 mmole), copper iodide (0.261 g, 1.37 mmole) in 40 mL dimethylformamide, and 40 mL piperidine was stirred at 60° C. for 5 hours. The brown reaction mixture was poured into 2N HCl, and extracted with diethyl ether. The combined organic phases were washed with saturated sodium bicarbonate, water, brine, and dried with magnesium sulfate. The organic phases were concentrated and the residue was loaded on to silica gel and chromatographed with silica gel (hexanes:ethyl acetate, 95:5) to afford 1.31 g (61%) of aldehyde 2 as a yellow solid: Mp=218–220° C.; $^1$H NMR (DMSO-$d_6$) δ 10.4 (s, 1 H), 7.93 (d, 2 H, J=8.7 Hz), 7.55 (d, 1 H, J=2.8 Hz), 7.34 (s, 1 H), 7.33 (s, 1 H), 7.09 (d, 2 H J=8.7 Hz), 3.87 (s, 3 H), 3.84 (s, 3 H); MS 283 (M+H)$^+$.

[5-Methoxy-2-(4-methoxy-phenyl)-benzofuran-7-yl]-methanol 3

Sodium borohydride (0.106 g, 2.73 mmole) was added to a solution of aldehyde 2 (0.700, 2.48 mmole) in ethanol (24 mL) and tetrahydrofuran (12 mL). After 1.5 hours stirring at room temperature under nitrogen, the reaction was concentrated. To the residue was added 2N HCl producing a white precipitate which was extracted into ethyl acetate. The combined organic phases were washed with saturated sodium bicarbonate, water, brine, and dried with magnesium sulfate. The organic phases were concentrated and the residue was loaded on to silica gel and chromatographed with silica gel (hexanes:ethyl acetate, 9:1) to afford 0.810 g (98%) of benzyl alcohol as a white solid: Mp=128–130° C.; $^1$H NMR (DMSO-$d_6$) δ 7.85 (d, 2 H, J=8.7 Hz), 7.19 (s, 1H), 7.06 (d, 2 H, J=8.7 Hz), 7.00 (d, 1 H, J=2.5 Hz), 6.88 (d, 1 H, J=2.1 Hz), 3.82 (s, 3 Hz), 3.79 (s, 3 H); MS, 285 (M+H)$^+$.

7-Bromomethyl-2-(4-hydroxy-phenyl)-benzofuran-5-ol 4

Benzyl Alcohol 3 (0.500 g, 1.759 mmole) was dissolved in dichloromethane (50 mL) and cooled to −78° C. in dry ice/acetone bath. To this solution, boron tribromide (1.0 M in dichloromethane), (7.04 mL, 7.05 mmole) was added drop wise over 15 minutes. After 30 minutes, the dark orange solution was allowed to come to room temperature and reacted for an additional 4 hours. The solution was concentrated and added to saturated sodium bicarbonate and extracted with ethyl acetate. Organic layers were combined and washed with water, brine, and dried over magnesium sulfate. The organic phases were concentrated and the residue was loaded on to silica gel and chromatographed with silica gel (hexanes:ethyl acetate, 7:3) to afford 0.495 g (88%) of benzyl bromide 4 as a white solid: Mp=337–339° C.; $^1$H NMR (DMSO-$d_6$) δ 7.90 (s, 2 H),), 7.74 (d, 2 H, J=8.8 Hz), 7.06 (s, 1 H), 6.89 (d, 2 H, J=8.7 Hz), 6.86 (d, 1 H, J=2.5 Hz), 6.77 (d, 1 H, J=2.2 Hz); MS 317/319 (M+H)$^+$.

[5-Hydroxy-2-(4-hydroxy-phenyl)-benzofuran-7-yl]-acetonitrile 5

To a solution of benzyl bromide 4 (0.0758 g, 0.238 mmole) in 5 mL dimethylformamide was added pulverized potassium cyanide (0.0232 g, 0.3563 mmole) and 18-crown-6 ether (0.100 g, 0.378 mmole). After stirring at 80° C. for 2 hours, the reaction mixture was cooled and poured into water and extracted with ethyl acetate. The combined organic phases were washed with saturated sodium bicarbonate, water, brine, and dried with magnesium sulfate. The organic phases were concentrated and the residue was loaded on to silica gel and chromatographed with silica gel (hexanes:ethyl acetate, 9:1) to afford 0.046 g (82%) of benzylnitrile 5 as a yellow solid: Mp=128–130° C.; $^1$H NMR (DMSO-$d_6$) δ 7.85 (d, 2 H, 8.7 Hz), 7.19 (s, 1 H), 7.06 (d, 2 H, J=8.7 Hz), 7.00 (d, 1 H, J=2.5 Hz), 6.88 (d, 1 H, J=2.1 Hz), 3.82 (s, 3 Hz), 3.79 (s, 3 H); MS, 285 (M+H)$^+$

2-(4-Hydroxy-phenyl)-7-methoxymethyl-benzofuran-5-ol 6

Cmpd 6 was prepared under the same conditions as 7, infra, but replacing ethanol with methanol, yielding methyl ether 6 as a white solid: Mp 186–188° C.; $^1$H NMR (DMSO-$d_6$) δ 9.82 (br s, 1 H), 9.12 (br s, 1 H), 7.69 (d, 2 H, J=8.5 Hz), 7.03 (s, 1 H), 6.87 (d, 2 H, J=8.4 Hz), 6.82 (d, 1 H, J=2.2 Hz), 6.68 (d, 1 H, J=2.0 Hz), 4.67 (s, 2 H), 3.36 (s, 3 H); MS 269 (M–H)$^-$

7-Ethoxymethyl-2-(4-hydroxy-phenyl)-benzofuran-5-ol 7

To a solution of benzyl bromide 4 (0.05 g, 0.159 mmole) in 5 mL ethanol was added potassium hydroxide (0.350 g, 0.627 mmole). After stirring at R.T. for 1 hour, the solvent was evaporated and the residue was poured into water and extracted with ethyl acetate. The combined organic phases were washed with saturated sodium bicarbonate, water, brine, and dried with magnesium sulfate. The organic phases were concentrated and the residue was loaded on to silica gel and chromatographed on silica gel (hexanes:ethyl acetate, 9:1) to afford 0.039 g (51%) of ethyl ether 7 as a tan solid: Mp=166–168° C.; $^1$H NMR (DMSO-$d_6$) δ 9.82 (br s, 1 H), 9.12 (bs, 1 H), 7.70 (d, 2 H, J=8.6 Hz), 7.02 (s, 1 H), 6.86 (d, 2 H, J=8.6 Hz), 6.81 (d, 1 H, J=2.1 Hz), 6.69 (d, 1 H, J=2.2 Hz), 4.71 (s, 2 H), 3.56 (q, 2 H, J=7.2 Hz), 1.18 (t, 3 H, J=7.2 Hz); MS 283 (M–H)$^-$

2-(4-Hydroxy-phenyl)-7-isopropoxymethyl benzofuran-5-ol 8

Cmpd 8 was prepared under the same conditions as cpd 7 replacing EtOH with iPrOH isopropanol, yielding isopropyl ether 8 as a white solid: Mp=195–197° C.; $^1$H NMR (DMSO-$d_6$) δ 9.82 (br s, 1 H), 9.11 (br s, 1 H), 7.69 (d, 2 H, J=8.5 Hz), 7.02 (s, 1 H), 6.86 (d, 2 H, J=8.5 Hz), 6.79 (d, 1 H, J=2.2 Hz), 6.70 (d, 1 H, J=2.0 Hz), 4.71 (s, 2 H), 3.73 (m, 1 H), 1.19 (d, 6 H, J=6.1 Hz); MS 297 (M–H)$^-$

2-(4-Hydroxy-phenyl)-7-methyl-benzofuran-5-ol 9

To a solution of benzyl bromide 4 (0.036 g, 0.113 mmole) in 2 mL methanol was added 5% Palladium on Carbon (0.100 g). After stirring at R.T. for 20 minutes, the mixture was filtered through glass wool and loaded on to silicagel and chromatographed with silica gel (hexanes:ethyl acetate, 9:1) to afford 0.019 g (70%) of methyl compound 9 as white solid: Mp=218–220° C.; $^1$H NMR (DMSO-$d_6$) δ 9.81 (br s, 1 H), 9.01 (br s, 1 H), 7.69 (d, 2 H, J=8.5 Hz), 6.99 (s, 1 H), 6.86 (d, 2 H, J=8.5 Hz), 6.70 (d, 1 H, J=2.3 Hz), 6.51 (d, 1 H, J=2.2 Hz), 2.41 (s, 3 H); MS 230 (M–H)$^-$

2-(4-Hydroxy-phenyl)-7-methylsulfanylmethyl-benzofuran-5-ol 10

To a solution of benzyl bromide 4 (0.052 g, 0.161 mmole) in 5 mL methanol was added sodium thiomethoxide (0.013 g, 0.177 mmole). After stirring at R.T. for 1 hour, the solvent was evaporated and the residue was poured into water and extracted with ethyl acetate. The combined organic phases were washed with saturated sodium bicarbonate, water, brine, and dried with magnesium sulfate. The organic phases were concentrated and the residue was loaded on to silica gel and chromatographed with silica gel (hexanes:ethyl acetate, 4:1) to afford 0.025 g (54%) of thioether 10 as a white solid: Mp=188–190° C.; $^1$H NMR (DMSO-$d_6$) δ 9.82 (s, 1 H), 9.14 (s, 1 H), 7.69 (d, 2 H, J=8.5 Hz), 7.01 (s, 1 H), 6.86 (d, 2 H, J=8.5 Hz), 6.77 (d, 1H, J=2.1 Hz), 6.63 (d, 1 H, J=2.1 Hz), 3.91 (s, 2 H), 2.05 (s, 3 H); MS 285 (M–H)$^-$

7-Ethylsulfanylmethyl-2-(4-hydroxy-phenyl)-benzofuran-5-ol 11

Compound 11 was prepared under the same conditions as 10, except that sodium thiomethoxide was replaced with sodium thioethoxide, yielding 0.041 g (92%) of thioether 11 as a light white solid: Mp=181–183° C.; $^1$H NMR (DMSO-$d_6$) δ 9.83 (s, 1 H), 9.14 (s, 1 H), 7.70 (d, 2 H, J=8.4 Hz), 7.02 (s, 1 H), 6.87 (d, 2 H, J=8.5 Hz), 6.76 (d, 1H, J=2.0 Hz), 6.65 (d, 1 H, J=2.1 Hz), 3.95 (s, 2 H), 2.49 (q, 2 H, J=7.3 Hz), 1.19 (t, 3 H, J=7.3 Hz); MS 299 (M–H)$^-$

2-(4-Hydroxy-phenyl)-7-phenylsulfanylmethyl-benzofuran-5-ol 12

Compound 12 was prepared under the same conditions as 10, except that sodium thiophenoxide was used as the nucleophile, yielding 0.069 g (76%) of thioether 12 as a light white solid: Mp=175–177° C.; $^1$H NMR (DMSO-$d_6$) δ 9.84 (s, 1 H), 9.13 (s, 1 H), 7.67 (d, 2 H, J=8.5 Hz), 7.39 (d, 2 H, J=7.6 Hz), 7.29 (t, 2 H, J=7.4 Hz), 7.17 (t, 1 H, J=7.4 Hz), 7.00 (s, 1 H), 6.85 (d, 2 H, J=8.5 Hz), 6.76 (d, 1H, J=2.2 Hz), 6.67 (d, 1 H, J=2.2 Hz), 4.45 (s, 2 H); MS 347 (M–H)$^-$

2-(4-Hydroxy-phenyl)-7-methanesulfinylmethyl-benzofuran-5-ol 13 and 2-(4-Hydroxy-phenyl)-7-methanesulfonylmethyl-benzofuran-5-ol 14

To a solution of 10 (0.070 g, 0.245 mmole) in 5 mL THF was added mCPBA (0.058 g, 0.257 mmole). After stirring at rt for 2 hour, the solvent was evaporated and the residue was poured into 10% sodium sulfite and extracted into ethyl acetate. The combined organic phases were washed with saturated sodium bicarbonate, water, brine, and dried with magnesium sulfate. The organic phases were concentrated and the residue was loaded on to silica gel and chromatographed on silica gel (hexanes:ethyl acetate, 1:1) to afford 0.050 g (68%) of sulfoxide 13 as a tan solid and 0.012 g (16%) of sulfone 14 as a light white solid.

13: Mp=234–236° C.; $^1$H NMR (DMSO-$d_6$) δ 9.85 (s, 1 H), 9.25 (s, 1 H), 7.73 (d, 2 H, J=8.5 Hz), 7.05 (s, 1 H), 6.87 (m, 3 H), 6.67 (d, 1 H, J=2.1 Hz), 4.34 (d, 1 H, J=12.0 Hz), 4.20 (d, 1 H, J=12.9 Hz), 2.57 (s, 3 H); MS 301 (M–H)$^-$

14: Mp=245–247° C.; $^1$H NMR (DMSO-$d_6$) δ 9.86 (s, 1 H), 9.31 (s, 1 H), 7.75(d, 2 H, J=8.5 Hz), 7.06 (s, 1 H), 6.90 (d, 1 H, J=2.2 Hz), 6.87 (d, 2 H, J=8.5 Hz), 6.78 (d, 1 H, J=2.2 Hz), 4.71 (s, 2 H), 3.5 (s, 3 H); MS 317 (M–H)$^-$

Synthesis of Compounds from Scheme 2

2-(4-Hydroxy-phenyl)-7-thiocyanatomethyl-benzofuran-5-ol 15

Compound 15 was prepared under the same conditions as 10 except that sodium thiocyanate was used as the nucleophile, yielding 0.021 g (78%) of thioether 15 as a light white solid: Mp=190–192° C.; $^1$H NMR (DMSO-$d_6$) δ 9.86 (s, 1 H), 9.32 (s, 1 H), 7.75 (d, 2 H, J=8.6 Hz), 7.07 (s, 1 H), 6.88 (m, 3 H), 6.74 (d, 1 H, J=2.3 Hz), 4.60) s, 2 H), MS 296 (M–H)$^-$

2-(4-Hydroxy-phenyl)-7-imidazol-1-ylmethyl-benzofuran-5-ol 16

To a solution of benzyl bromide 4 (0.070 g, 0.215 mmole) in 10 mL DMF was added imidazole (0.030 g, 0.437 mmole). After stirring at 60° C. for 3 hours, the reaction mixture was poured into water and extracted with ethyl acetate. The combined organic phases were washed with saturated sodium bicarbonate, water, brine, and dried with magnesium sulfate. The organic phases were concentrated and the residue was loaded on to silica gel and chromatographed with silica gel (hexanes:ethyl acetate, 9:1) to afford 0.059 g (88%) of imidazole 16 as a light tan solid: Mp=269–271° C.; $^1$H NMR (DMSO-$d_6$) δ 9.88 (s, 1 H), 9.24 (s, 1 H), 7.88 (s, 1 H), 7.72 (d, 2 H, J=8.6 Hz), 7.26 (s, 1 H), 7.04 (s, 1 H), 6.93 (s, 1 H), 6.88 (d, 2 H, J=8.7 Hz), 6.83 (d, 1 H, J=2.3 Hz), 6.50 (d, 1 H, J=2.3 Hz), 5.46 (s, 2 H); MS 305 (M−H)$^-$

7-Bromomethyl-5-methoxy-2-(4-methoxy-phenyl)-benzofuran 17

Benzyl Alcohol 3 (1.02 g, 3.59 mmole) was dissolved in dichloromethane (70 mL) and cooled to −78° C. in an dry ice/acetone bath. Boron tribromide (1.0 M in dichloromethane), (3.95 mL, 3.95 mmole) was added drop wise over 15 minutes. After 30 minutes, the light orange solution was allowed to come to room temperature and reacted for an additional four hours. The solution was concentrated and added to saturated sodium bicarbonate, and extracted with ethyl acetate. Organic layers were combined and washed with water and brine, dried over magnesium sulfate. The organic phases were concentrated and the residue was loaded on to silica gel and chromatographed with silica gel (hexanes:ethyl acetate, 9:1) to afford 2.91 g (81%) of benzyl bromide17 as a white solid: Mp=158–160° C.; $^1$H NMR (DMSO-$d_6$) δ 7.88(d, 2 H, J=8.8 Hz), 7.23 (s, 1 H), 7.11 (d, 2 H, J=2.5 Hz), 7.09 (d, 2 H, J=8.9 Hz), 6.99 (d, 1 H, J=2.5 Hz), 4.96 (s, 2 H), 3.82 (s, 3 H), 3.80 (s, 3 H).

[5-Methoxy-2-(4-methoxy-phenyl)-benzofuran-7-yl]-acetonitrile 18

To a solution of benzyl bromide 17 (0.640 g, 1.843 mmole) in 100 mL dimethylformamide was added pulverized potassium cyanide (0.186 g, 2.76 mmole) and 18-crown-6 ether (0.786 g, 2.965 mmole). After stirring at 80° C. for 2 hours, the reaction mixture was cooled and poured into water and extracted with ethyl acetate. The combined organic phases were washed with saturated sodium bicarbonate, water, brine, and dried with magnesium sulfate. The organic phases were concentrated and the residue was loaded on to silica gel and chromatographed with silica gel (hexanes:ethyl acetate, 9:1) to afford 0.529 g (98%) of acetonitrile 18 as a white solid: Mp=149–150° C.; $^1$H NMR (DMSO-$d_6$) δ 7.87 (d, 2 H, J=8.8 Hz), 7.26 (s, 1 H), 7.12 (d, 1 H, J=2,4 Hz), ), 7.10 (d, 2 H, J=8.7 Hz), 6.88 (d, 1 H, J=2.4 Hz), 4.42 (s, 2 H), 3.82 (s, 3 H), 3.81 (s, 3 H); MS 294 (M+H)$^+$

2-[5-Methoxy-2-(4-methoxy-phenyl)-benzofuran-7-yl]-propionitrile 19

To a solution of acetonitrile 18 (0.200 g, 0.682 mmole) in 10 mL dimethylformamide was added pulverized potassium hydroxide (0.046 g, 0.818 mmole) and methyl iodide (0.161 g, 0.818 mmole). After stirring at rt for 2 hours, the orange reaction mixture was poured into water and extracted with ethyl acetate. The combined organic phases were washed with saturated sodium bicarbonate, water, brine, and dried with magnesium sulfate. The organic phases were concentrated and the residue was loaded on to silica gel and chromatographed with silica gel (hexanes:ethyl acetate, 95:5) to afford 0.087 g (42%) of propionitrile 19 as a white solid. Used as is for conversion to 21, infra.

2-[5Methoxy-2-(4-methoxy-phenyl)-benzofuran-7-yl]-2-methyl-propionitrile 20

To a solution of acetonitrile 18 (0.054 g, 0.184 mmole) in 5 mL dimethylformamide was added pulverized potassium hydroxide (0.024 g, 0.390 mmole) and methyl iodide (0.0552 g, 0.0391 mmole). After stirring; at rt for 2 hours, the reaction mixture was poured into water and extracted with ethyl acetate. The combined organic phases were washed with saturated sodium bicarbonate, water, brine, and dried with magnesium sulfate. The organic phases were concentrated and the residue was loaded on to silica gel and chromatographed with silica gel (hexanes:ethyl acetate, 95:5) to afford 0.046 g (78%) of methyl-propionitrile 20 as a yellow solid: Mp=146–148° C., $^1$H NMR (DMSO-$d_6$) δ 7.87 (d, 2 H, J=8.8 Hz), 7.26 (s, 1 H), ), 7.15 (d, 1 H, J=2.4 Hz), 7.10 (d, 2 H, J= 8.9 Hz), 6.86 (d, 1 H, J=2.4 Hz), 3.82 (s, 3 H), 3.81 (s, 3 H), 1.89 (s, 6 H); MS 322 (M+H)$^+$

2-[5-Hydroxy-2-(4-hydroxy-phenyl)-benzofuran-7-yl]-propionitrile 21

Compound 21 was prepared by heating 19 with excess Pyr-HCl at 200° C. until reaction judged complete by TLC (<1 h). The reaction was allowed to cool and partitioned between 2 N HCl aq and EtOAc. The EtOAc was washed with saturated NaHCO$_3$ aq., brine and dried over MgSO$_4$. Chromatography on silica gel (EtOAc/hexanes) yielded the desired product as a yellow solid: Mp=183–185° C.; $^1$H NMR (DMSO-$d_6$) δ 9.88 (br s, 1 H), 9.37 (br s, 1 H), 7.73 (d, 2 H, J=8.6 Hz), 7.07 (s, 1 H), 6.89 (m, 3 H), 6.73 (d, 1 H, J=2.2 Hz), 4.63 (q, 1 H, J=7.2 Hz), 1.68 (d, 3 H, J=7.2 Hz); MS 278 (M−H)$^-$

2-[5-Hydroxy-2-(4-hydroxy-phenyl)-benzofuran-7-yl]-2-methyl-propionitrile 22

Compound 22 was prepared similarly to 21, yielding the product as a light yellow solid: Mp=284° C.; $^1$H NMR (DMSO-$d_6$) δ 9.89 (br s, 1 H), 9.38 (br s, 1 H), 7.72 (d, 2 H, J=8.6 Hz), 7.08 (s, 1H), 6.90 (d, 2 H, J=8.5 Hz), 6.89 (d, 1 H, J=2.4 Hz), 6.77 (d, 1 H, J=2.3 Hz), 1.87 (s, 6 H); MS, 294 (M+H)$^+$

5-Methoxy-2-(4-methoxy-phenyl)-benzofuran-7-carboxylic acid 23

To a solution of aldehyde 2 (0.200 g, 0.708 mmole) in 20 mL THF was added a solution of sodium chlorite (0.370 g, 3.08 mmole) and sodium dihydrogen phosphate (0.300 g, 3.32 mmole) in water and amylene (6 mL, 57 mmole). After stirring at room temperature for 2 hours, the THF evaporated and the was residue poured into water and extracted with ethyl acetate. The combined organic phases were washed with saturated sodium bicarbonate, water, brine, and dried with magnesium sulfate. The organic phases were concentrated and the residue was loaded on to silica gel and chromatographed with silica gel (hexanes ethyl acetate, 9:1)

to afford 0.081 g (42%) of acid 23 as a white solid: Mp=218–220° C.; ¹H NMR (DMSO-d₆) δ 7.85 (d, 2 H, J=8.7 Hz), 7.41 (d, 2 H, J=2.7 Hz), 7.31 (d, 2 H, J=2.7 Hz), 7.28 (s, 1 H), 7.10 (1 H, J=8.9 Hz), 3.84 (s, 3 H), 3.82 (s, 3 H); MS 299 (M+H)⁺. Product was contaminated with some 3-Cl compound.

5-Hydroxy-2-(4-hydroxy-phenyl)-benzofuran-7-carboxylic acid 24

To acid 23 (0.075 g, 0.250 mmole) was added pyridine-HCl (5.1 g, 43.3 mmole). After stirring at 200° C. for 30 minutes, the mixture was cooled to rt, poured into 2N HCl aq. and extracted with ethyl acetate. The combined organic phases were washed with saturated sodium bicarbonate, water, brine, and dried with magnesiumsulfate. The organic phases were concentrated and the residue was loaded on to silica gel and chromatographed with silica gel (hexanes: ethyl acetate, 1:1) to afford 0.052 g (77%) of acid 24 as a white solid: Mp=260–262° C.; ¹H NMR (DMSO-d₆) δ 13.3 (br s, 1 H), 9.79 (br s, 1 H), 9.46 (br s, 1 H), 7.91 (d, 2 H, J=8.7 Hz), 7.30 (d, 1 H, J=2.4 Hz), 7.11 (s, 1 H), 7.08 (d, 1 H, J=2.4 Hz), 6.98 (d, 2 H, J=8.9 Hz); MS 269 (M–H)⁻ Product was still contaminated with some 3-Cl compound.

7-Hydroxymethyl-2-(4-hydroxy-phenyl)-benzofuran-5-ol 25

Acid 24 (0.030 g, 0.112 mmole) in 5 mL THF was added a solution of Borane-THF complex (2.0 mL, 2.0 mmole) in THF. After stirring at 65° C. for 6 hours, the THF was evaporated and the residue was poured into 2N HCl and extracted with ethyl acetate. The combined organic phases were washed with saturated sodium bicarbonate, water, brine, and dried with magnesium sulfate. The organic phases were concentrated and the residue was separated by HPLC (70:30, H₂O/AcCN) to afford 0.011 g (36%) of benzyl alcohol 25 as a white solid: Mp=258–260° C.; ¹H NMR (DMSO-d₆) δ 9.81 (s, 1H), 9.45 (s, 1H), 7.70 (d, 2 H, J=8.9 Hz), 7.00 (s, 1 H), 6.86 (d, 2 H, J=8.7 Hz), 6.76 (s, 2 H), 5.27 (m, 1 H), 4.75 (d, 2 H, J=5.6 Hz); MS 255 (M–H) ⁻

5-Methoxy-2-(4-methoxy-phenyl)-benzofuran-7-carbaldehyde oxime 26

To a solution of hydroxylamine hydrochloride (0.119 g, 1.59 mmole) and pyridine (0.134 mL, 1.59 mmole) in 14 mL ethanol was added aldehyde 2 (0.300 g, 1.06 mmole). After stirring at 80° C. for 1.5 hours, the solvent was evaporated and the residue was poured into water and extracted with ethyl acetate. The combined organic phases were washed with saturated sodium bicarbonate, water, brine, and dried with magnesium sulfate. The organic phases were concentrated and the residue was loaded on to silica gel and chromatographed with silica gel (hexanes:ethyl acetate, 1:1) to afford 0.213 g (67%) of oxime 26 as a white solid: Mp=185–187° C.; ¹H NMR (DMSO-d₆) δ 11.6 (s, 1 H), 8.49 (s, 1 H), 7.88 (d, 2 H, J=8.9 Hz), 7.24 (s, 1 H), 7.17 (d, 1 H, J=2.8 Hz), 7.10–7.09 (m, 3 H, J=9.2 Hz), 3.83 (s, 3 H), 3.81 (s, 3 H); MS 298 (M+H)⁺

[5-Hydroxy-2-(4-hydroxy-phenyl)-benzofuran-7-yl]-carbonitrile 27

To oxime 26 (0.090 g, 0.303 mmole) was added Pyr-HCl (8.0 g, 69.3 mmole). After stirring at 200° C. for 30 minutes, the mixture was cooled to R.T., added to 2N HCl and extracted with ethyl acetate. The combined organic phases were washed with saturated sodium bicarbonate, water, brine, and dried with magnesium sulfate. The organic phases were concentrated and the residue was loaded on to silica gel and chromatographed with silica gel (hexanes:ethyl acetate, 1:1) to afford 0.039 g (51%) of acetonitrile 27 as a tan solid: Mp>300° C.; ¹H NMR (DMSO-d₆) δ 9.99 (br s, 1 H), 9.88 (br s, 1 H), 7.74 (d, 2 H, J=8.6 Hz), 7.27 (d, 1 H, J=2.3 Hz), 7.21 (s, 1 H), 7.07 (d, 1 H, J=2.1 Hz), 6.91 (d, 2 H, J=8.6 Hz); MS 250 (M–H)⁻

Synthesis of Compounds from Scheme 3

5-Methoxy-2-(4-methoxy-phenyl)-7-vinyl-benzofuran 28

Methyl triphenylphosphonium bromide (0.122 g, 0.334 mmole) was dissolved in 5 mL THF and placed in an acetone/dry ice bath at –78° C.; n-Butyl lithium (0.131 mL, 0.328 mmole) was added and the mixture was allowed to stir for 30 minutes. To this solution was added aldehyde 3 (0.078 g, 0.278 mmole) in 3 mL THF. After stirring at room temperature for 4 hours, the reaction mixture was placed in an oil bath and allowed to stir overnight. at 65° C. The solvent was evaporated and the residue was poured into water and extracted with ethyl acetate. The combined organic phases were washed with saturated sodium bicarbonate, water, brine, and dried with magnesium sulfate. The organic phases were concentrated and the residue was loaded on to silica gel and chromatographed with silica gel (hexanes:ethyl acetate, 95:5) to afford 0.055 g (71%) of 28 as a white solid: Mp=182–184° C.; ¹H NMR (DMSO-d₆) δ 7.87 (d, 2 H, J=8.4 Hz), 7.22 (s, 1 H), 7.08 (m, 3 H), 6.98 (m, 1 H), 6.96 (d, 1 H, J=2.3 Hz), 6.30 (d, 1 H, J=17.8 Hz), 5.59 (d, 1 H, J=11.4 Hz), 3.82 (s, 3 H), 3.80 (s, 3 H); MS 281 (M+H)⁺

7-Ethyl-5-methoxy-2-(4-methoxy-phenyl)-benzofuran 29

Compound 29 was prepared by dissolving 28 in MeOH, treating with catalytic 5% Pd/C and stirring under an atmosphere of H₂. After stirring at rt under an atmosphere of H₂ for 20 minutes, the mixture was filtered through glass wool and loaded on to silica gel and chromatographed with silica gel (hexanes:ethyl acetate) to afford 29 as a white solid: Mp=187–189° C.; ¹H NMR (DMSO-d₆) δ 7.83 (d, 2 H, J=8.7 Hz), 7.17 (s, 1 H), 7.06 (d, 2 H, J=8.8 Hz), ), 6.94 (d, 1 H, J=2.5 Hz), 6.70 (d, 1 H, J=2.4 Hz), 3.81 (s, 3 H), 3.77 (s, 3 H), 2.88 (q, 2 H, J=7.8 Hz), 1.31 (t, 3 H, J=7.8 Hz); MS 283 (M+H)⁺

7-Ethyl-2-(4-hydroxy-phenyl)-benzofuran-5-ol 30

Compound 30 was prepared by demethylation of 29 using Pyr-HCl (method described previously for preparation of 21): Mp=218–220° C.; ¹H NMR (DMSO-d₆) δ 9.81 (s, 1 H), 9.02 (s, 1 H), 7.69 (d, 2 H, J=8.5 Hz), 6.99 (s, 1H), 6.86 (d, 2 H, J=8.5 Hz), 6.70 (d, 1 H, J=2.2 Hz), 6.55 (d, 1 H, J=2.0 Hz), 2.81 (q, 2 H, J=7.5 Hz), 1.29 (t, 3 H, J=7.5 Hz); MS 255 (M+H)⁺

7-(2,2-Dichloro-vinyl)-5-methoxy-2-(4-methoxy-phenyl)-benzofuran 31

To a solution of aldehyde 2 (0.065 g, 0.230 mmole) in 5 mL dichloromethane was added triphenylphosphine (0.244 g, 0.929 mmole) and carbontetrachloride (0.05 mL g, 0.484 mmole). After stirring at rt for 4 hours, the solvent was evaporated and the residue was poured into water and extracted with ethyl acetate. The combined organic phases were washed with saturated sodium bicarbonate, water, brine, and dried with magnesium sulfate. The organic phases were concentrated and the residue was loaded on to silica gel and chromatographed with silica gel (hexanes:ethyl acetate, 9:1) to afford 0.071 g (88%) of 31 as a white solid: Mp=129–131° C.; $^1$H NMR (DMSO-d$_6$) δ 7.90 (d, 2 H, J=8.4 Hz), 7.54 (s, 1 H), 7.25 (s, 1 H), 7.19 (s, 2 H), 7.07 (d, 2 H, J=8.6 Hz), 3.82 (s, 3 H), 3.81 (s, 3 H); MS 349 (M+H)$^+$

7-(2,2-Dichloro-vinyl)-5-hydroxy-2-(4-hydroxy-phenyl)benzofuran-5-ol 32

Compound 32 was demethylated with Pyr-HCl as described previously for 21: Mp=217–219° C.; $^1$H NMR (DMSO-d$_6$) δ 9.87 (s, 1 H), 9.37 (s, 1 H), 7.75 (d, 2 H, J=8.6 Hz), 7.48 (s, 1 H), 7.10 (d, 1 H, J=2.3 Hz), 7.08 (s, 1 H), 6.93 (d, 1 H, J=2.2 Hz), 6.87 (d, 2 H, J=8.6 Hz); MS, 319 (M–H)$^-$

5-Methoxy-2-(4-methoxy-phenyl)-7-propenyl-benzofuran 33

Ethyl triphenylphosphonium bromide (0.319 g, 0.850 mmole) was dissolved in 15 mL THF and placed in an acetone/dry ice bath at −78° C. n-Butyl lithium (0.334 mL, 0.836 mmole) was added and the mixture was allowed to stir for 30 minutes. To this solution was added aldehyde 2 (0.078 g, 0.278 mmole) in 3 mL THF. After stirring at room temperature for 4 hours, the reaction mixture was placed in an oil bath and allowed to stir overnight at 65° C. The solvent was evaporated and the residue was poured into water and extracted with ethyl acetate. The combined organic phases were washed with saturated sodium bicarbonate, water, brine, and dried with magnesium sulfate. The organic phases were concentrated and the residue was loaded on to silica gel and chromatographed with silica gel (hexanes:ethyl acetate, 9:1) to afford 0.187 g (90%) of 33 as a white solid: Mp=116–118° C.; $^1$H NMR (DMSO-d$_6$) δ 7.87 (d, 2 H, J=8.6 Hz), 7.20 (s, 1 H), 7.08 (d, 2 H, J=8.6 Hz), 6.98 (d, 1 H, J=2.4 Hz), 6.85 (d, 1 H, J=2.5 Hz), 6.78 (d, 1 H, J=6.4 Hz), 3.82 (s, 3 H), 3.80 (s, 3 H), 1.99(s, 3 H); MS 295 (M+H)$^+$

5-Methoxy-2-(4-methoxy-phenyl)-7-propyl-benzofuran 34

Compound 34 was prepared by hydrogenation of 33 (Pd/C, H$_2$) yielding 34 as a white solid: Mp=109–111° C.; $^1$H NMR (DMSO-d$_6$) δ 7.83 (d, 2 H; J=8.6 Hz), 7.17 (s, 1 H), 7.07 (d, 2 H, J=8.5 Hz), 6.94 (d, 1 H, J=2.4 Hz), 6.70 (d, 1 H, J=2.5 Hz), 3.81 (s, 3 H), 3.76 (s, 3 H), 2.84 (t, 2 H, J=7.8 Hz), 1.75 (q, 2 H, J=7.4 Hz), 0.96 (t, 3 H, J=7.4 Hz); MS 297 (M+H)$^+$

2-(4-Hydroxy-phenyl)-7-propyl-benzofuran-5-ol 35

Compound 35 was prepared via demethylation of 34 with Pyr-HCl: Mp=178–180° C.; $^1$H NMR (DMSO-d$_6$) δ 9.81 (br s, 1 H), 9.02 (br s, 1 H), 7.67 (d, 2 H, J=8.5 Hz), 6.98 (s, 1 H), 6.87 (d, 2 H, J=8.5 Hz), 6.71 (d, 1 H, J=2.1 Hz), 6.51 (d, 1 H, J=2.1 Hz), 2.84 (t, 2 H, J=7.8 Hz), 1.75 (q, 2 H, J=7.4 Hz), 0.96 (t, 3 H, J=7.4 Hz); MS 269 (M+H)$^+$

5-Hydroxy-2(4hydroxy-phenyl)-benzofuran-7-carboxylic acid Isopropyl ester 36

1 M HCl in diethyl ether (1.20 mL, 1.20 mmole) was added to a solution of carboxylic acid 24 (0.046, 0.172 mmole) in isopropanol 5 mL. After refluxing overnight, the reaction mixture was concentrated and partitioned between water and ethyl acetate. The combined organic phases were washed with saturated sodium bicarbonate, water, brine, and dried with magnesium sulfate. The organic phases were concentrated and the residue was loaded on to silica gel and chromatographed with silica gel (hexanes:ethyl acetate, 4:1) to afford 0.390 g (74%) of ester 36 as a light tan solid: Mp>250° C.; Calculated mass for C$_{18}$H$_{16}$O$_5$ is 312.32, found by ESI MS, 311 (M–H)$^-$; $^1$H NMR (DMSO-d$_6$)δ 9.93 (br s, 1 H), 9.55 (br s, 1 H), 7.73(d, 2 H, J=8.6 Hz), 7.22 (d, J=2.6 Hz), 7.17 (d, 1 H, J=2.5 Hz), 7.13 (s, 1 H), 6.90 (d, 2 H, J=8.7 Hz), 5.21 (m, 1 H), 1.42 (d, 6 H, J=6.2 Hz).

5-Hydroxy-2-(4-hydroxy-phenyl)-benzofuran-7-carboxylic acid propyl ester 37

Compound 37 was prepared under the same conditions as described for 36 except that isopropanol was replaced by propanol, yielding ester compound 37 as a white solid: Mp=220–222° C.; $^1$H NMR (DMSO-d$_6$) δ 9.92 (br s, 1 H), 9.54 (br s, 1 H), 7.73 (d, 2 H, J=8.6 Hz), 7.23 (d, 1 H, J=2.5 Hz), 7.17 (d, 1 H, J=2.5 Hz), 7.13 (s, 1 H), 6.88 (d, 2 H, J=8.7 Hz),1.07 (t, 3 H, J=7.3 Hz),), 1.81 (q, 2 H, J=7.2 Hz, J=6.7 Hz), 4.32 (t, 2 H, J=6.4 Hz); MS 311 (M–H)$^-$

5-Hydroxy-2-(4-hydroxy-phenyl)-benzofuran-7-carboxylic acid methyl ester 38

A solution of carboxylic acid 24 (0.35 g , 1.3 mmol) in HCl/MeOH(10 ml) was refluxed for 2 hr. The reaction was then cooled, concentrated and the product was dissolved in EtOAc, washed with sat NaHCO$_3$, separated dried, and concentrated to give a solid. The solid was triturated with CH$_2$Cl$_2$, filtered to give a solid (0.15 g, 47%): Mp=236–238° C.; $^1$NMR (DMSO-d$_6$) δ 9.90 (s, 1 H), 9.57 (s, 1 H), 7.73 (d, 2 H, J=8.5Hz), 7.23 (d, 1 H, J=2.1 Hz), 7.17 (d. 1 H, J=2.1 Hz),7.12 (s, 1 H), 6.88 (d, 2 H, J=8.5 Hz), 3.94 (s, 3 H); MS 283 (M–H)$^-$

5-Hydroxy-2-(4-hydroxy-phenyl)-benzofuran-7-carboxylic acid ethyl ester 39

A solution of carboxylic acid 24 (3.5 g, 13 mmol) in HCl/EtOH(100 ml) was refluxed for 2 hr. The reaction was then cooled, concentrated and the product was dissolved in EtOAc, washed with sat NaHCO$_3$, dried over MgSO$_4$, and concentrated to give a solid. The solid was triturated with CH$_2$Cl$_2$ filtered to give the desired product (3.5 g, 92%); Mp=221–223° C.; $^1$NMR (DMSO-d$_6$) δ 9.90 (s, 1 H), 9.55(s, 1 H), 7.73 (d, 2 H, J=8.5 Hz), 7.23 (d, 1 H, J=2.1 Hz), 7.17 (d. 1 H, J=2.5 Hz), 7.12 (s, 1 H), 6.88 (d, 2 H, J=8.5 Hz), 4.43–4.35 (m, 2 H), 1.41 (t, 3 H, J=7.0 Hz); MS 297 (M–H)$^-$.

Synthesis of Compounds from Scheme 4

(3-Fluoro-4-methoxy-phenylethynyl)-trimethyl-silane (not numbered in scheme)

A solution of 2-fluoro-4-bromoanisole (2.14 g, 10.4 mmole), dichlorobis(triphenylphosphine) palladium (II)

(0.501 g, 0.304 mmole), copper iodide (0.036 g, 0.189 mmole), and 20 mL diisopropylamine was stirred at 70° C. over night in a sealed pressure tube. The black reaction mixture was poured into 2N HCl and extracted with ethyl acetate. The combined organic phases were washed with saturated sodium bicarbonate, water, brine, and dried with magnesium sulfate. The organic phases were concentrated and the residue was loaded on to silica gel and chromatographed with silica gel (hexanes:ethyl acetate, 95:5) to afford 2.13 g (92%) of acetylene as a light brown low melting solid: Mp=28–29° C.; $^1$H NMR (DMSO-d$_6$) δ 7.30 (m, 2 H), 7.15 (t, 1 H, J=8.7 Hz), 3.86 (s, 3 H), 0.217 (s, 9 H).

4-Ethynl-2-fluoro-1-methoxy-benzene (not numbered in scheme)

Pulverized potassium hydroxide (1.22 g, 18.2 mmole) was added to a solution of TMS-acetylene compound prepared immediately, supra, (2.31, g, 10.3 mmole) in 100 mL of methanol. The light brown solution was allowed to stir at rt for one hour, after which, the solvent was evaporated and partitioned between water and ethyl acetate. The combined organic phases were washed with saturated sodium bicarbonate, water, brine, and dried with magnesium sulfate. The organic phases were concentrated and the residue was loaded on to silica gel and chromatographed with silica gel (hexanes:ethyl acetate, 4:1) to afford 1.51 g (97%) of acetylene as a light brown brown solid: Mp=36–38° C. $^1$H NMR (DMSO-d$_6$) δ 7.35 (dd, 1 H, J=12.1 Hz, J=1.9 Hz), 7.29 (dd, 1 H, J=1.0 Hz, J=8.5 Hz),), 7.17 (t, 1 H, J=8.7 Hz), 4.15 (s, 1 H), 3.85 (s, 3 H).

2-(3-Fluoro-4-methoxy-phenyl)-5-methoxy-benzofuran-7-carboxylic acid methyl ester 40

A solution of ester 1 (2.79 g, 9.05 mmole), 4-ethynyl-2-fluoro-1-methoxy-benzene, immediately supra, (1.63 g, 10.86 mmole), dichlorobis(triphenylphosphine) palladium (II) (0.636 g, 0.906 mmole), copper iodide (0.345 g, 1.81 mmole), 40 mL dimethylformamide, and 40 mL piperidine was stirred at 60° C. for 5 hours. The brown reaction mixture was cooled, poured into 2N HCl, and extracted with diethyl ether. The combined organic phases were washed with saturated sodium bicarbonate, water, brine, and dried with magnesium sulfate. The organic phases were concentrated and the residue was triturated with methanol, loaded on to silica gel and chromatographed with silica gel (hexanes: ethyl acetate, 95:5) to afford 2.21 g (74%) of ester 40 as a tan solid: Mp=121–123° C.; $^1$H NMR (DMSO-d$_6$) δ 7.81–7.73 (m, 2 H), 7.46 (d, 1 H, J=2.6 Hz), 7.37 (s, 1 H), 7.37–7.31 (m, 2 H), 6.88 (d, 1 H, J=2.4 Hz), 4.42 (s, 2 H), 3.97 (s, 3 H), 3.91 (s, 3 H), 3.84 (s, 3 H); MS 331 (M+H)$^+$

[2-(3-Fluoro-4-methoxy-phenyl)-5-methoxy-benzofuran-7-yl]-methanol 41

Fluoro ester 40 (1.00 g, 3.63 mmole), was dissolved in 40 mL THF and stirred under nitrogen. To this solution was added lithium aluminumhydride (1M in THF, 3.81 mL, 3.81 mmole) dropwise over fifteen minutes. After stirring at rt for one half hour, the solvent was removed and the mixture was poured into 2N HCl and extracted with ethyl acetate. The combined organic phases were washed with saturated sodium bicarbonate, water, brine, and dried with magnesium sulfate. The organic phases were concentrated and the residue was loaded on to silica gel and chromatographed with silica gel (hexanes:ethyl acetate, 4:1) to afford 0.800 g (73%) of benzyl alcohol 41 as a tan solid: Mp=128–130° C.; $^1$H NMR (DMSO-d$_6$) δ 7.78 (dd, 1 H, J=12.5 Hz, 2.0 Hz), 7.69 (dd, 1 H, J=8.7 Hz, 1.1 Hz), 7.29 (t, 2 H, J=8.1 Hz), 7.01 (d, 1 H, J=2.5 Hz), 6.90 (d, 1 H J=2.5 Hz), 5.37 (br s, 1 H), 4.81 (d, 2 H, J=3.1 Hz), 3.90 (s, 3 H), 3.81 (s, 3 H); MS 303 (M+H)$^+$ 7-Bromomethyl-2-(3-fluoro-4-hydroxy-phenyl)-benzofuran-5-ol 42

Compound 42 was prepared analogously to compound 4 yielding 0.200 g (36%) of 42 as a tan solid: Mp=269–271° C.; $^1$H NMR (DMSO-d$_6$) δ 10.3 (br s, 1 H), 9.34 (br s, 1 H), 7.72 (dd, 1H, J=12.2 Hz, 2.0 Hz), 7.68 (dd, 1 H, J=8.4 Hz, 1.5 Hz), 7.17 (t, 2 H, J=8.7 Hz), 6.88 (d, 1 H, J=2.5 Hz), 6.80 (d, 1 H, J=2.9 Hz), 4.92 (s, 2 H); MS 335/337 (M–H)$^-$

[2-(3-Fluoro-4-hydroxy-phenyl)-5-hydroxy-benzofuran-7-yl]-acetonitrile 43

Compound 43 was prepared under the same conditions as 5, yielding 0.782 g (71%) of 43 as a cream colored solid: Mp=242–244° C.; $^1$H NMR (DMSO-d$_6$) δ 10.3 (br s, 1 H), 9.38 (br s, 1 H), 7.69 (dd, 1H, J=12.3 Hz, 2.0 Hz), 7.55 (dd, 1 H, J=8.4 Hz, J=1.4 Hz), 7.18 (s, 1 H), 7.07 (t, 1 H, J=8.6 Hz), 6.88 (d, 1 H, J=2.3 Hz), 6.75 (d, 1 H, J=2.2 Hz), 4.28 (s, 2 H); MS 282 (M–H)$^-$

[4-Chloro-5-hydroxy-2-(4-hydroxy-phenyl)-benzofuran-7-yl]-acetonitrile 43a

[5-Hydroxy-2-(4-hydroxy-phenyl)-benzofuran-7-yl]-acetonitrile 43 (0.0650 g, 0.2390 mmole) was dissolved in acetonitile (5 mL) and cooled in an ice bath. To this solution, was added pulverized potassium carbonate (0.073 g, 0.527 mmole). After stirring for one hour, N-chlorosuccinimide (0.031 g, 0.227 mmole), which was dissolved in 0.5 mL acetonitrile, was added over one hour in three portions and stirred overnight. The solution was poured into 0.1 N HCl solution and the aqueous layer was extracted with ethyl acetate. Organic layers were combined and washed with saturated sodium bicarbonate, water, brine, and dried over magnesium sulfate. The organic phases were concentrated and the residue was chromatographed by HPLC with (water: acetonitrile, 1:1) to afford 0.031 g (43%) of chloro 59 as a tan solid: mp 242–244° C.; Calculated mass for $C_{16}H_{10}NO_3Cl$ is 299.71, found by Fl MS, 298/300 (M+H)$^-$; $^1$H NMR (DMSO-d$_6$) δ 10.07 (s, 1 H), 9.96 (s, 1 H) 7.80 (d, 2 H, 8.6 Hz)., 7.19 (s, 1 H), 6.91 (t, 3 H, J=8.1 Hz), 6.31 (s, 2 H).

2-(3-Fluoro-4-methoxy-phenyl)-5-methoxy-benzofuran-7-carboxylic acid 44

2N NaOH (20 mL, 40 mmole) was added to a solution of ester 40 (0.766, 2.301 mmole) in 60 mL 50:50 methanol/THF and refluxed at 70° C. for one half hour. The reaction mixture was cooled and poured into 2N HCl (25 mL, 50 mmole). The white precipitate was extracted into ethyl acetate and the combined organic phases were washed with saturated sodium bicarbonate, water, brine, and dried with magnesium sulfate. The organic phases were concentrated and the residue was loaded on to silica gel and chromatographed with silica gel (hexanes:ethyl acetate, 1:1) to afford 0.7109 g (98%) of acid 44 as a tan solid: Mp=254–256° C.; $^1$H NMR (DMSO-d$_6$) δ 13.3 (br s, 1 H), 7.75 (dd, 1 H, J=2.0

Hz, J=1.9 Hz), 7.70 (d, 1 H, J=9.3 Hz), 7.42 (d, 1 H, J=2.6 Hz), 7.38 (s, 1 H), 7.34 (m, 2 H), 3.91 (s, 3 H), 3.84 (s, 3 H); MS 315 (M−H)⁻

2-(3-Fluoro-4-methoxy-phenyl)-5-methoxy-benzofuran-7-carboxylic acid methoxy-methyl-amide 45

A solution of 44 (0.400 g, 1.27 mmole), N,O dimethylhydroxylamine hydrochloride (0.247 g, 2.53 mmole), DMAP (0.309 g, 2.53 mmole), and EDCI (0.364 g, 1.90 mmole), in 40 mL dimethylformamide was stirred at rt for 2 hours. The reaction mixture was poured into water and extracted with ethyl acetate. The combined organic phases were washed with saturated sodium bicarbonate, water, brine, and dried with magnesium sulfate. The organic phases were concentrated and the residue was loaded on to silica gel and chromatographed with silica gel (hexanes:ethyl acetate, 7:3) to afford 0.290 g (63%) of amide 45 as a tan solid: Mp=100–102° C.; $^1$H NMR (DMSO-d$_6$) δ 7.74 (dd, 1H, J=2.0 Hz), 7.66 (d, 1 H, J=8.6 Hz), 7.37 (s, 1 H), 7.31 (t, 1 H, J=8.7 Hz), 7.24 (d, 1 H, J=2.6 Hz), 6.93 (d, 1 H, J=2.6 Hz), 3.90 (s, 3 H), 3.82 (s, 3 H), 3.59 (br s, 3 H), 3.30 (s, 3 H); MS 360 (M+H)⁺

2-(3-Fluoro-4-methoxy-phenyl)-5methoxy-benzofuran-7-carbaldehyde 46

Compound 46 was prepared by LiAlH$_4$ reduction of the amide under similar conditions as described previously for the preparation of 41 yielding 0.208 g (94%) of 46 as a yellow solid: Mp=161–163° C.; $^1$H NMR (DMSO-d$_6$) δ 10.4 (br s, 1 H), 7.87 (dd, 1 H, J=12.5 Hz, 2.0 Hz), 7.78 (d, 1 H, J=7.4 Hz, 1.0 Hz), 7.53 (d, 1 H, J=2.4 Hz), 7.43 (s, 1 H), 7.35 (d, 1 H, J=2.9 Hz), 7.34 (t, 1 H, J=8.9 Hz), 3.92 (s, 3 H), 3.87 (s, 3 H); MS 301 (M+H)⁺

2-(3-Fluoro-4-methoxy-phenyl)-5-methoxy-benzofuran-7-carbaldehyde oxime 47

Compound 47 was prepared under the same conditions as described for 26, yielding 0.163 g (85%) of 47 as a light yellow solid: Mp=208–210° C.; $^1$H NMR (DMSO-d$_6$) δ 11.6 (br s, 1 H), 8.52 (br s, 1 H), 7.83 (dd, 1 H, J=12.5 Hz, 2.0 Hz), 7.74 (d, 1 H, J=8.6 Hz), 7.34 (s, 1 H), 7.30 (t, 1 H, J=8.9 Hz), 7.18 (d, 1 H, J=2.5 Hz), 7.12 (d, 1 H, J=2.5 Hz), 3.91 (s, 3 H), 3.81 (s, 3 H); MS, 316 (M+H)⁺

2-(3-Fluoro-4-hydroxy-phenyl)5-hydroxy-benzofuran-7-carbonitrile 48

Compound 48 was prepared under the same conditions as 27 yielding 0.062 g (57%) of 48 as a yellow solid: Mp>300° C.; $^1$H NMR (DMSO-d$_6$) δ 10.5 (br s, 1 H), 9.92 (br s, 1 H), 7.69 (dd, 1 H, J=12.1 Hz, 2.0 Hz), 7.56 (dd, 1 H, J=8.4 Hz, J=1.5 Hz), 7.31 (s, 1 H), 7.28 (d, 1 H, J=2.4 Hz), 7.11 (d, 1 H, J=2.4 Hz), 7.09 (t, 1 H, J=8.8 Hz); MS 268 (M−H)⁻

2-(3-Fluoro-4-hydroxy-phenyl)-7-methyl-benzofuran-5-ol 49

Compound 49 was prepared under the same conditions as 9, yielding 0.018 g (54%) of 49 as a white solid: Mp=196–198° C.; $^1$H NMR (DMSO-d$_6$) δ 10.3 (br s, 1 H), 9.1 (br s, 1 H), 7.64 (dd, 1 H, J=12.5 Hz, 2.0 Hz), 7.52 (d, 1 H, J=8.4 Hz, J=1.5 Hz), 7.31 (s, 1 H), 7.05 (t, 1 H, J=8.7 Hz), 6.71 (d, 1 H, J=2.3 Hz), 6.54 (d, 1 H, J=1.6 Hz); MS 257 (M−H)⁻

Synthesis of Compounds in Scheme 5

3-Bromo-2-hydroxy-5-methoxy-benzaldehyde 50

To a cooled 0° C. solution of Methyl 4-methoxysalicylate (30 g, 200 mmol) in chloroform (500 ml) was added bromine (32 g, 20 mmol) and the reaction was stirred at rt for 5 hr. The reaction was then washed with 10% sodium sulfite, dried, concentrated to give a solid. The solid was triturated with hexane, filtered to give a yellow solid (14 g, 35%): Mp=107–110° C.

3-Bromo-2,5-dimethoxy-benzaldehyde 51

A solution of 50 (10 g, 43 mmol), Methyl Iodide (7.3 g, 52 mmol), and K$_2$CO$_3$ (12 g, 86 mmol) in acetone (200 ml) was heated to reflux. After 4 hr, the reaction was cooled, poured into water and extracted with ether. The ether layer was dried concentrated and the product was purified by silica gel column chromatography (10% EtOAc/Hex) to give 51 as a solid (7.0 g, 67%): Mp=62–64° C.; $^1$H NMR (CDCl$_3$) δ 10.32 (s, 1 H), 7.38 (d, 1 H, J=2.8 Hz), 7.28 (d, 1 H, J=3.2 Hz), 3.93 (s, 3 H), 3.82 (s, 3 H); MS 245/247 (M+H)⁺

(3-Bromo-2,5-dimethoxy-phenyl)-methanol 52

To a cooled (0° C.) solution of 51 (8.0 g, 33 mmol) in THF (100 ml) was added LiAlH$_4$ (15 ml of 1.0M in THF) dropwise. After 15 min, the reaction was quenched with 2N HCl and the aqueous layer was extracted with EtOAc. The EtOAc layer was dried concentrated to give a solid (7.5 g, 93%): Mp=65–67° C.; $^1$H NMR (DMSO-d$_6$) δ 7.05 (d, 1 H, J=3.0 Hz), 6.98 (d, 1 H, J=2.5 Hz), 5.28 (t, 1 H, J=4.9 Hz), 4.47 (d, 2 H, J=5.7 Hz), 3.73 (s, 3 H), 3.67 (s, 3 H); MS 245 (M−H)⁻

1-Bromo-3-chloromethyl-2,5-dimethoxy-benzene 53

To a solution of 52 (7.5 g, 30 mmol) and ZnCl$_2$ (1 g) in THF (100 ml) was added SOCl$_2$ (5.31 g, 45 mmol) dropwise. After 1 hr at rt, the reaction was poured into water and extracted with ether. The ether was dried, concentrated and the product was purified by column chromatography on silica gel (10% EtOAc/hex) to give 53 as an oil (5.5 g, 75%): $^1$H NMR(DMSO-d$_6$) δ 7.21 (d, 1 H, J=3.0 Hz), 7.08 (d, 1 H, J=3.0 Hz), 4.73 (s, 2 H), 3.78 (s, 3 H), 3.75 (s, 3 H)

(3-Bromo-2,5-dimethoxy-phenyl)-acetonitrile 54

A solution of 1-Bromo-3-chloromethyl-2,5-dimethoxybenzene 53 (7.0 g, 26.4 mmol) and KCN (1.7 g, 26.4 mmol) in DMSO (50 ml) was heated to 75° C. After 2 hr, the reaction was cooled and poured into water. The aqueous layer was extracted with EtOAc and the organic layer was dried and concentrated. The product was purified by column chromatography on silica gel (20% EtOac/Hex) to give 54 as an oil (5.2 g, 77%): $^1$H NMR (DMSO-d$_6$) δ 7.20 (d, 1 H, J=3.0 Hz), 6.99 (d, 1 H, J=3.0 Hz), 4.00 (s, 2 H), 3.75 (s, 6 H)

(3-Bromo-2,5-dimethoxy-phenyl)-acetic acid 55

A solution of (3-Bromo-2,5-dimethoxy-phenyl)-acetonitrile 54 (5.2 g, 20.4 mmol) in water (10 ml), conc H$_2$SO$_4$ (10 ml), and AcOH (30 ml) was heated to 100° C. After 3 hr the reaction was cooled; and poured into water. The aqueous layer was extracted with EtOAc which was then dried over MgSO$_4$, filtered and concentrated. The product was purified by column chromatography on silica gel (50% EtOAc/Hex) to give a solid (2.8 g, 55%): Mp=62–65° C.; $^1$H NMR (DMSO-d$_6$) δ 12.45 (br s, 1 H), 7.09 (d, 1 H, J=2.9 Hz), 6.87 (d, 1 H, J=3.0 Hz), 3.72 (s, 3 H), 3.66 (s, 3 H), 3.59 (s, 2 H); MS 273/27 (M−H)$^−$.

2-(3-Bromo-2,5-dimethoxy-phenyl)-1-(4-methoxy-phenyl)-ethanone 56

To a cooled (0° C.) solution of 55 (2.8 g, 10 mmol) in CH$_2$Cl$_2$ (50 ml) was added SOCl$_2$ (1.8 g, 15 mmol) and DMF (2 ml) and the reaction was stirred for 3 hr. The solution was concentrated and the resulting oil was taken up into dichloroethane (50 ml). The solution was cooled and anisole (2.0 g, 1 8.4 mmol) was added followed by AlCl$_3$ (1.8 g, 13.8 mmol). The reaction was stirred for 1 hr and was then quenched with 2N HCl aq. The organic layer was dried over MgSO$_4$, concentrated to give an oil which was taken up into MeOH and a solid crystallized. The solid was collected by filtration to give a white solid (2.3 g, 63%); Mp=91–93° C.; $^1$H NMR (DMSO-d$_6$) δ 8.01 (d, 2 H, J=8.4 Hz), 7.10–7.05 (m, 3 H), 6.85 (d, 1 H, J=5.7 Hz), 4.35 (s, 2 H), 3.85 (s, 3 H), 3.72 (s, 3H), 3.59 (s, 3 H); MS 363/365 (M−H)$^−$

7-Chloro-2-(4-hydroxy-phenyl)-benzofuran-5-ol 57 and 7-Bromo-2-(4-hydroxy-phenyl)-benzofuran-5-ol 58

A mixture of 57 (0.5 g, 1.35 mmol) and Pyridine HCl (5 g) was heated to 200° C. After 1 Hr, the reaction was cooled and then diluted with water. The aqeous phase was extracted With EtOAc. The EtOAc was dried, concentrated to give a solid which was purified by reverse phase HPLC to give 57 (5 mg, 1.5%) and 58 (60 mg, 15%).

57: Mp=235–237° C.; $^1$H NMR (DMSO-d$_6$) δ 9.94 (br s, 1 H), 9.62 (br s, 1 H), 7.72 (d, 2 H, J=8.5 Hz), 7.12 (s, 1 H), 6.91–6.87 (m, 3 H), 6.74 (d, 1 H, J=5.2 Hz); MS 259/261 (M−H)$^−$.

58: Mp=242–244° C.; $^1$H NMR (DMSO-d$_6$) δ 9.92 (br s, 1 H), 9.68 (br s, 1 H), 7.69 (d 2 H, J=8.6 Hz), 7.14 (s, 1 H), 6.90–6.87 (m, 4 H); MS 303/305 (M−H)$^−$.

3-[5-Hydroxy-2-(4-hydroxy-phenyl)benzofuran-7-yl]-acrylic acid methyl ester 59

To a solution of 7-bromo-2-(4-hydroxy-phenyl)-benzofuran-5-ol 58 (1.0 g, 3.3 mmol) in triethylamine (10 mL) and acetonitrile (10 mL) was added methyl acrylate (0.44 mL, 4.9 mmol) and tri-(o-toly) phosphine (0.2 g, 0.66 mmol). This mixture was purged with nitrogen for 10 minutes. Then palladium (II) acetate (0.037 g, 0.17 mmol) was added and the reaction was heated at reflux for 4 hours; To the cooled reaction was added 2N HCl and the product was extracted into ethyl acetate. The organic layer was washed with brine, dried over MgSO$_4$ and the solvent removed in vacuo. The residue was purified via flash. chromatography on silica gel, eluting with 22–50% ethyl acetate in hexane to give 0.16 g of 59: Mp=231–234° C.; $^1$HMR (DMSO-d$_6$) δ 9.93 (s, 1 H), 9.44 (s, 1 H), 7.80 (d, 1 H, J=16.1 Hz), 7.72 (d, 2 H, J=8.6 Hz), 7.13 (s, 1 H), 7.02 (d, 1 H, J=2.3 Hz), 6.98 (d, 1 H, J=2.3 Hz), 6.93 (d, 1 H, J=16.2 Hz), 6.92 (d, 2 H, J=8.6 Hz) 3.79 (s, 3 H); MS 311 (M+H)$^+$

3-[5-Hydroxy-2-(4-hydroxy-phenyl)-benzofuran-7-yl]-propionic acid methyl ester 60

To a solution of 3-[5-hydroxy-2-(4-hydroxy-phenyl)benzofuran-7-yl]-acrylic acid methyl ester 59 (0.1 g, 0.32 mmol) in methanol (5 mL) and purged with nitrogen was added catalytic 10% palladium on carbon. The reaction vessel was evacuated and a balloon of hydrogen was added. After 7 hours, the reaction was filtered and the solvent removed in vacuo. The product was purified via flash chromatography on silica gel, eluting with 7% methanol in dichloromethane to give 0.015 g of 3-[5-hydroxy-2-(4-hydroxy-phenyl)-benzofuran-7-yl]-propionic acid methyl ester 60: Mp=167–170° C.; $^1$H NMR (DMSO-d$_6$) δ 9.83 (s, 1 H), 9.08 (s, 1 H), 7.70 (d, 2 H, J=8.6 Hz), 7.00 (s, 1 H), 6.87 (d, 2 H, J=8.6 Hz), 6.73 (d, 1 H, J=2.3 Hz), 6.53 (d, 1 H, J=2.2 Hz), 3.59 (s, 3 H), 3.07 (t, 2 H, J=7.5 Hz), 2.77 (t, 2 H, J=7.6 Hz); MS 313 (M+H)$^+$.

3-[5-Hydroxy-2-(4-hydroxyphenyl)-benzofuran-7-yl]-acrylamide 61

To a solution of 7-bromo-2-(4-hydroxy-phenyl)-benzofuran-5-ol 58 (0.3 g, 0.98 mmol) in triethylamine (5 mL) and acetonitrile (5 mL) was added acrylamide (0.077 g, 1.08 mmol) and tri-(o-tolyl) phosphine (0.060 g, 0.2 mmol). This mixture was purged with nitrogen for 10 minutes. Then palladium (II) acetate (0.022 g, 0.098 mmol) was added and the reaction was heated at reflux for 3.5 hours. To the cooled reaction was added 2N HCl and the product was extracted into ethyl acetate. The organic layer was washed with brine, dried over MgSO$_4$ and the solvent removed in vacuo. The residue was purified via flash-chromatography on silica gel, eluting with 10% methanol in dichloromethane to give 0.15 g of 3-[5-hydroxy-2-(4-hydroxyphenyl)-benzofuran-7-yl]-acrylamide 61: Mp=275° C. (dec); $^1$H NMR (DMSO-d$_6$) δ 9.89 (s, 1 H), 9.35 (s, 1 H), 7.86 (br s, 1 H), 7.83 (d, 2 H, J=8.6 Hz), 7.53 (d, 1 H, J=15.9 Hz), 7.23 (br s, 1 H), 7.11 (s, 1 H), 7.04 (d, 1 H, J=15.9 Hz), 6.94 (d, 1 H, J=2.4 Hz), 6.90 (d, 2 H, 8.7 Hz); 6.83 (d, 1 H, J=2.3 Hz); MS 296 (M+H)$^+$

2-(4-Hydroxy-phenyl)-7-methoxy-benzofuran-5-ol 62

A solution consisting of 58 (1.5 g, 4.9 mmol) in DMF (25 mL) was treated with CuIBr (1.0 g, 6.5 mmol) and NaOMe (6 mL, 4.4 N in MeOH, 27 mmol) and heated to 160° C. for approximately 1 hour. The reaction mixture was allowed to cool and then worked up by adding 2 N HCl and EtOAc. The EtOAc layer was washed with NaHCO$_3$ aq, brine and dried over MgSO$_4$. The solution was concentrated and chromatographed on silica gel (1:4 EtOAc/hexanes to 3:7 EtOAc/hexanes) to yield 0.47 g of pdt: Mp=167–168° C., $^1$H NMR (DMSO-d$_6$) δ 9.84 (br s, 1 H), 9.18 (br s, 1 H), 7.67 (d, 2 H, J=8.6 Hz), 6.99 (s, 1 H), 6.86 (d, 2 H, J=8.7 Hz), 6.46 (d, 1 H, J=2.1 Hz), 6.34 (d, 1 H, J=2.1 Hz), 3,89 (s, 3 H); MS 257 (M+H)$^+$.

4,7-Dibromo-2-(4-hydroxy-phenyl)-benzofuran-5-ol 63

Compound 59 (0.6 g, 2.1 mmol) in CH$_3$CN was treated with K$_2$CO$_3$ (0.58 g, 4.1 mmol) followed by NBS (0.37 g, 2.1 mmol) and the reaction was stirred at rt for 30 mins and then treated with a 10% Na$_2$SO$_3$ aq solution followed by NaHCO$_3$ aq. EtOAc was added and the organic layer was washed with brine and dried over MgSO4. The material was purified by reverse phase HPLC using a gradient (Water/CH3CN 80:20 to Water/CH3CN 20:80) to render 40 mg of the desired pdt as a grey powder: Mp=215–217° C.; $^1$H NMR (DMSO-d$_6$) δ 10.3 (br s, 1H), 10.1 (br s, 1H), 7.79 (d, 2 H, J=8.7 Hz), 7.18 (s, 1 H), 7.06 (s, 1 H), 6.90 (d, 2 H, J=8.7 Hz), MS 381/383/385 (M–H)$^-$.

3-[5-Hydroxy-2-(4-hydroxy-phenyl)-benzofuran-7-yl]-acrylonitrile 64

A solution of 3-[5-hydroxy-2-(4-hydroxyphenyl)-benzofuran-7-yl]-acrylamide 61 (0.07 g, 0.24 mmol) in DMF (5 mL) and phosphorous oxychloride (0.11 mL) was heated at 65° C. for 2 hours. Then ice was added to the reaction mixture and the product extracted into ethyl acetate. The organic layer was dried over MgSO$_4$ and the solvent removed in vacuo. The crude product was submitted for reverse phase prep HPLC. The product was isolated to give 0.007 g of 3-[5-hydroxy-2-(4-hydroxy-phenyl)-benzofuran-7-yl]-acrylonitrile 64: $^1$H NMR (DMSO-d$_6$) δ 9.90 (s, 1 H), 9.48 (s, 1 H), 7.82 (d, 2 H, J=8.6 Hz), 7.79 (d, 1 H, J=16.7 Hz), 7.13 (s, 1 H), 7.03 (d, 1 H, J=2.3 Hz), 6.92 (d, 1 H, J=2.4 Hz), 6.88 (d, 2 H, J=8.7 Hz), 6.71 (d, 1 H, J=16.8 Hz); MS 276 (M–H)$^-$.

3-[5-Hydroxy-2-(4-hydroxy-phenyl)benzofuran-7-yl]-propionitrile 65

A solution of 3-[5hydroxy-2-(4-hydroxy-phenyl)-benzofuran-7-yl]-acrylonitrile-64 (0.028 g, 0.1 mmol) in methanol (1 mL) was purged with nitrogen and 10% palladium on carbon added. The reaction vessel was evacuated and a hydrogen balloon added. After an hour, the reaction was filtered and the solvent removed in vacuo. The product was purified via flash chromatography, eluting with 3% methanol in dichloromethane to give 0.007 g of 3-[5-hydroxy-2-(4-hydroxy-phenyl)-benzofuran-7-yl]-propionitrile 65: $^1$H NMR (DMSO-d$_6$) δ 9.84 (s, 1 H), 9.17 (s, 1 H), 7.73 (d, 2 H, J=8.6 Hz), 7.02 (s, 1 H), 6.87 (d, 2 H, J=8.6 Hz), 6.79 (d, 1 H, J=2.3 Hz), 6.62 (d, 1 H, J=2.2 Hz), 3.12 (t, 2 H, J=7.1 Hz), 2.96 (t, 2 H, J=7.4 Hz); MS 280 (M+H)$^+$.

Synthesis of Compounds from Scheme 6

7-Bromo-5-(tert-butyl-dimethyl-silanyloxy)-2-[4-(tert-butyl-dimethyl-silanyloxy)-phenyl]-benzofuran 66

To a solution of 7-bromo-2-(4-hydroxy-phenyl)-benzofuran-5-ol 58 (0.5 g, 1.6 mmol) in THF was added imidazole (0.33 g, 4.8 mmol) and tert-butyldimethyl silylchloride (0.69 g, 4.6 mmol). This mixture was stirred at room temperature overnight. The reaction mixture was diluted with ethyl ether and washed with water, then dried over MgSO$_4$ and the solvent removed in vacuo. The crude was purified via flash chromatography, eluting with hexane, giving 0.62 g of 5-(tert-butyl-dimethyl-silanyloxy)-2-[4-tert-butyl-dimethyl-silanyloxy)-phenyl]-7-bromo-benzofuran 66: $^1$H NMR (DMSO-d$_6$) δ 7.81 (d, 2 H, J=8.6 Hz), 7.29 (s, 1 H), 7.08 (d, 1 H, J=2.2 Hz), 7.02 (d, 2 H, J=8.7 Hz), 7.00 (d, 1 H, J=2.2 Hz), 0.97 (s, 18 H), 0.24 (s, 6 H), 0.23 (s, 6 H).

2-(4-Hydroxy-phenyl)-7-vinyl-benzofuran-5-ol 67

To a solution of 66 (0.48 g, 0.9 mmol) in xylene was added tributyl vinyl tin (0.28 g, 0.9 mmol) and tri-(o-tolyl) phosphine (0.055 g, 0.18 mmol). This mixture was purged with nitrogen for 15 minutes. Then palladium (II) chloride was added and there action was heated at 130° C. for 2 hours. The reaction was filtered and the solvent removed in vacuo. The residue was used in the next step without further purification. To a solution of 5-(tert-butyl-dimethyl-silanyloxy)-2-[4-tert-butyl-dimethyl-silanyloxy)-phenyl]-7-vinyl-benzofuran (0.4 g, 0.9 mmol) in THF (10 mL) was added 1.0M tetrabutyl ammonium fluoride (1.8 mL, 1.8 mmol) and the reaction mixture was stirred at room temperature 20 minutes. The reaction was diluted with ethyl ether and washed twice with water. The organic layer was dried over MgSO$_4$ and the solvent removed in vacuo. The product was purified via flash chromatography, eluting with 50% ethyl acetate in hexane, to give 0.19 g of 2-(4-hydroxy-phenyl)-7-vinyl-benzofuran-5-ol 67: Mp=182–184° C.; $^1$H NMR (DMSO-d$_6$) δ 9.86 (s, 1 H), 9.20 (s, 1 H), 7.73 (d, 2 H, J=8.6 HZ), 7.06 (s, 1 H), 6.89 (d, 2 H, J=8.8 Hz), 6.92 (dd, 1 H, J=16.7 Hz, 11.3 Hz), 6.84 (d, 1 H, J=2.3 Hz), 6.76 (d, 1 H, J=2.3 Hz), 6.21 (dd, 1 H, J=17.8 Hz, 1.2 Hz), 5.54 (dd, 1 H, J=11.3 Hz, 1.2 Hz); MS 253 (M+H)$^+$.

2,2,2-Trifluoro-1-[5-hydroxy-2-(4-hydroxy-phenyl)-benzofuran-7-yl]-ethanone 68

Compound 66 (0.6 g, 1.1 mmol) in 10 mL of THF was cooled to −78° C. and treated by dropwise addition of n-BuLi (0.6 mL, 2.5 M in hexanes, 1.5 mmol). After stirring for 5 minutes, a solution containing (N-methoxy, N'-methyl)-acetamide in 1 mL THF was added and the rxn was allowed to rt and stirred overnight. The crude reaction mixture was treated with a few mLs of 2 N HCl aq and the THF evaporated off. The aqueous layer was extracted with EtOAc, washed with NaHCO$_3$ aq, brine, and dried over MgSO$_4$. After filtration, the EtOAc was concentrated and chromatographed on silica gel (0:100 EtOAc/hexanes to 1:4 EtOAc/hexanes). The concentrated fractions containing the silylated phenols were concentrated and redissolved in 5 mLs of THF and treated with tetrabutyl ammonium fluoride (TBAF) (2 mL, 1 M in THF). After stirring for 30 minutes, the reaction mixture was acidified with 2 N HCl aq, the THF was evaporated off and the aqueous layer extracted with EtOAc. The EtOAc layer was washed with saturated NaHCO$_3$ aq, brine and dried over MgSO$_4$. After filtration, the EtOAc was concentrated and chromatographed on silica gel (5:95 EtOAc/hexanes to 4:6 EtOAc/hexanes) to yield 80 mg of the desired pdt as an orange solid: Mp=215–216° C.; $^1$H NMR (DMSO-d$_6$) δ 9.84 (br s, 1 H), 9.22 (br s, 1 H), 7.68 (d, 2 H, J=8.5 Hz), 7.00 (s, 1 H), 6.98 (d, 1 H, J=2.5 Hz), 6.92 (d, 1 H, J=2.5 Hz), 6.88 (d, 2 H, J=8.6 Hz); MS 321 (M–H)$^-$.

4-Chloro-2-(4-hydroxy-phenyl)-7-methoxy-benzofuran-5-ol 69

Compound 62 (0.1 g, 0.39 mmol) in CH$_3$CN (10 mL) was treated with portionwise addition of NCS (0.033 g, 0.24 mmol). After addition, 10% Na$_2$SO$_3$ aq was added followed by NaHCO$_3$ and brine. The EtOAc layer was dried over MgSO4, filtered, concentrated and chromatographed on silica gel (3:7 EtOAc/hexanes) to yield 0.016 g of the product: Mp=176–177° C.; $^1$H NMR (DMSO-d$_6$) δ 9.89 (br s, 2 H), 7.74 (d, 2 H, J=8.6 Hz), 7.10 (s, 1 H), 6.87 (d, 2 H, J=8.7 Hz), 6.55 (s, 1 H), 3.91 (s, 3 H); MS 291 (M+H)$^+$.

4-Bromo-2-(4-hydroxy-phenyl)-7-methoxy-benzofuran-5-ol 70

Compound was prepared analogously to chloro-analogue 69 except that NBS was used as the halogenating agent: Mp=170° C.; $^1$H NMR (DMSO-d$_6$) δ 9.91 (br s, 2 H), 7.74 (d, 2 H, J=8.6 Hz), 7.01 (s, 1 H), 6.86 (d, 2 H, J=8.7 Hz), 6.56 (s, 1 H), 3.91 (s, 3 H); MS 333 (M–H)$^-$.

5-Hydroxy-2-(4-hydroxy-phenyl)-7-methoxy-benzofuran-4-carbaldehyde 71

A solution of 62 (0.25 g, 1.0 mmol) in DMF (20 mL) was treated with POCl$_3$ (1 mL, 11 mmol) and heated at 80° C.–100° C. for 15 minutes. The reaction mixture was worked up by allowing to cool and then poured into crushed ice. 2N NaOH aq was added and the solution stirred for several minutes and then the mixture was acidified with 2N HCl aq and then neutralized with NaHCO$_3$ aq. The mixture was then extracted with EtOAc and washed with brine, dried over MgSO$_4$, filtered, concentrated and chromatographed on silica gel (2:8 to 4:6 EtoAc/hexanes) to yield a solid which still contained some starting material, but that was purified by trituration with EtOAc to yield 47 mg the desired pdt as a white solid: Mp=254–255° C.; $^1$H NMR (DMSO-d$_6$) δ 10.29 (s, 1 H), 10.0 (br s, 1 H), 7.73 (d, 2 H, J=8.7 Hz), 7.59 (s, 1 H), 6.88 (d, 2 H, J=8.7 Hz), 6.46 (s, 1 H), 4.00 (s, 3 H); MS 281 (M–H)$^-$.

5-Hydroxy-2-(4-hydroxy-phenyl)-7-methoxy-benzofuran-4-carbaldehyde oxime 72

Compound 71 (0.029 g, 0.1 mmol) in EtOH/Pyr (1 mL/0.5 mL) was treated with NH$_2$OH HCl (0.040 g, 0.58 mmol) and the mixture heated briefly to reflux (approximately 5 minutes) and allowed to cool and then the solution was partitioned between EtOAc and 2 N HCl aq and the organic layer was then washed with NaHCO$_3$ aq, brine, dried over MgSO$_4$, filtered, concentrated and triturated with CH$_2$Cl$_2$ to render 29 mg of the desired oxime: Mp=205° C. (dec.); $^1$H NMR (DMSO-d$_6$) δ 11.1 (s, 1 H), 10.0 (s, 1 H), 9,90 (s, 1 H), 8.53 (s, 1 H), 7.65 (d, 2 H, J=8.6 Hz), 7.39 (s, 1 H), 6.88 (d, 2 H, J=8.7 Hz), 6.47 (s, 1 H), 3.94 (s, 3 H); MS 300 (M+H)$^+$.

5-Hydroxy-2-(4-hydroxy-phenyl)-7-methoxy-benzofuran-4-carbonitrile 73

Compound 62 (0.49 g, 1.9 mmol) in 20 mL of DMF was treated with 1 mL of POCl$_3$ and heated at 80° C.–100° C. for 1 hour, cooled and treated with a few mLs of 2 N NaOHaq. After stirring for a few minutes, the reaction mixture was then acidified with excess 2N HCl aq and the entire reaction mixture was then extracted with EtOAc, washed with NaHCO$_3$, brine and dried over MgSO$_4$. Filtration and concentration yielded the crude 4-formyl derivative (0.25 g) that was used as is for the next step.

Compound 71 (0.25 g, 0.88 mmol), in a solution consisting of 5 mL pyr/5 mL EtOH and treated with NH$_2$OH—HCl (0.2 g, 2.9 mmol) and the reaction mixture was heated briefly to boiling and then allowed to cool. The solution was concentrated and the residue was dissolved in EtOAc and washed with 2N HCl aq and then NaHCO$_3$ aq followed by brine. The solution was then dried over MgSO$_4$, filtered and concentrated to render the crude oxime.

The crude 7 oxime 72 was heated in neat Ac$_2$O at 100° C. for 30 minutes. The Ac$_2$O was removed and the crude product was dissolved in EtOAc, washed with brine and dried over MgSO$_4$. The solution was concentrated down and the crude triacetate was dissolved in DMF (10 mL) and treated with NaH (0.1 g, 60% dispersion in mineral oil, 2.5 mmol) and the reaction mixture was heated to 100° C. for 15 min. After cooling to rt, the solution was treated with a 20% NaOH aq solution and enough MeOH to get everything in one phase. This solution was then heated briefly (long enough to hydrolyze the acetates as determined by TLC analysis) and allowed to cool back to rt. The solution was acidified with 2N HCl aq and the solution was extracted with EtOAc. The EtOAc extract was washed with NaHCO$_3$ and brine and dried over MgSO$_4$. The solution was filtered, concentrated and chromatographed on silica gel (2:8 to 4:6 EtOAc/hexanes) to yield 80 mg of the pdt nitrile 73 as a white solid: Mp=286–288° C.; $^1$H NMR (DMSO-d$_6$) δ 10.9 (br s, 1 H), 9.98 (br s, 1 H), 7.77 (d, 2 H, J=8.7 Hz), 7.20 (s, 1 H), 6.87 (d, 2 H, J=8.7 Hz), 6.48 (s, 1 H), 3.97 (s, 3 H).

2-(3-Fluoro-4-hydroxy-phenyl)-5-hydroxy 7-methoxy-benzofuran-4-carbonitrile 73a Compound 73a was prepared analogously to compound 73: Mp=265–267° C.; $^1$H NMR (DMSO-d$_6$) δ 11.0–10.3 (br s, 2 H), 7.75 (d, 1 H, J=12.2 Hz, 2.0 Hz), 7.59 (dd, 1 H, J=8.4 Hz, 1.4 Hz), 7.34 (s, 1 H), 7.06 (t, 1 H, J=8.78 Hz), 6.51 (s, 1 H), 3.98 (s, 3 H); MS 300 (M+H)$^+$ Synthesis of Compounds from Scheme 7

2-(2,5-Dimethoxy-phenyl)-1-(4-methoxy-phenyl)ethanone 74

To a cooled solution (0° C.) of anisole (1.3 g, 12.4 mmol) and (2,5-Dimethoxyphenyl)acetyl chloride (2.2 g, 10.3 mmol) in dichloroethane (30 ml) was added AlCl$_3$ (1.6 g, 12.4 mmol) and the reaction was stirred for thirty minutes. The reaction was then quenched with 2N HCl and the organic layer was then separated, dried, and concentrated. The resulting oil was taken up into MeOH and a solid crystallized which was collected by filtration to give a white solid (1.7 g, 58%): Mp=108–111° C.; $^1$H NMR (CDCl$_3$) δ 8.01 (d, 2 H, J=9.0 Hz), 6.92 (d, 2 H, J=8.8 Hz), 6.80–6.70 (m, 3 H), 4.20 (s, 2 H), 3.86 (s, 3 H), 3.75 (s, 3 H), 3.74 (s, 3 H); MS 287 (M+H)$^+$

2-(4-Hydroxy-phenyl)-benzofuran-5-ol 75

A mixture of 74 (1.5 g, 5.2 mmol) and Pyridine HCl (10 g) was heated to 200° C. After 1.5 hr, the reaction was cooled and diluted with water. The aqueous layer was extracted with EtOAc and the organic layer was dried, concentrated to give a solid which was triturated with CH$_2$Cl$_2$ to give a solid (0.6 g, 51%): Mp=275–278° C.; $^1$H NMR (DMSO-d$_6$) δ 9.81 (br s, 1 H), 9.12 (br s, 1 H), 7.66 (d, 2 H, J=2.5 Hz), 7.32 (d, 1 H, J=8.5 Hz), 7.00 (s, 1 H), 6.90–6.83 (m, 3 H), 6.65 (dd, 1 H, J=8.6 Hz, 2.6 Hz); MS 225 (M–H)$^-$.

2-(2,5-Dimethoxy-phenyl)-1-(2-fluoro-4-methoxyphenyl)-ethanone 76 and 2-(2-Fluoro-4-hydroxyphenyl)-benzofuran-5-ol 77

A solution of 3-Fluoro anisole (2 g, 16 mmol) and 2,5-dimethoxyphenacetyl chloride in dichloroethane (50 mL) was treated with AlCl$_3$ (2.3 g, 18 mmol) and stirred at rt until TLC analysis indicated reaction was complete. The reaction was worked up by adding a 2 N HCl aq solution to the reaction (slowly) and washing with saturated NaHCO$_3$ aq, brine and drying over MgSO$_4$. After filtering, the EtOAc was concentrated and chromatographed on silica gel (EtOAc/hexanes 1:4) to yield 1 gram of the acylated intermediate 76 as well as an isomer as an oily solid that was used as is for the next reaction step. All of 76 from the previous step (1 g, 3.3 mmol) was heated with pyr-HCl at 180° C.–200° C. until TLC indicated reaction completion. The reaction was worked up by partitioning between 2 N HCl aq and EtOAc and washing the EtOAc with saturated NaHCO$_3$, brine, and drying over MgSO$_4$. The solution was filtered, concentrated and chromatographed on silica gel to yield 0.48 g of impure pdt 77. The product thus obtained was recrystallized from EtOAc/hexanes to yield desired product plus a small amt of unidentified impurity: Mp=218–222° C.; $^1$H NMR (DMSO-d$_6$) δ 10.39 (s, 1 H), 9.20 (s, 1 H), 7.74 (t, 1 H, J=8.7 Hz), 7.37 (d, 1 H, J=8.8 Hz), 6.96–6.94 (m, 2 H), 6.79–6.70 (m, 3 H); MS 243 (M–H)$^-$.

5-OMe-Benzofuran 2-boronic acid 78

A solution of 5-OMe benzofuran (10 g, 67.6 mmol) in THF (150 mL) was cooled to −78° C. and treated by dropwise addition of n-BuLi (30 mL, 75 mmol, 2.5 M in hexanes) and stirred at −789° C. for 5–10 minutes. Trimethyl borate (60 mL, 0.54 mol) was added quickly and the reaction was allowed to come to rt. The solution was then treated with 2 N HCl aq and the THF was evaporated off. The product precipitated out and was collected by filtration to render 11 g of the desired material as a solid that was used as is for the subsequent reaction.

4-(5-Methoxy-benzofuran-2-yl)-3-methyl-phenol 79

A solution of 78 (1 g, 5.4 mmol) and 3-methyl-4-bromo phenol (0.8 g, 7.0 mmol) in EtOH/toluene/2M Na$_2$CO$_3$ aq (1/5/5 ratio) was treated with Pd(PPh$_3$)$_4$ (0.3 g, 0.27 mmol) and heated at reflux and monitored by TLC for reaction completion. The reaction was worked up by partitioning between EtOAc/2 N HCl aq, washing the EtOAc layer with saturated NaHCO$_3$ aq, brine and drying over MgSO$_4$. After filtering, the solution was concentrated and chromatographed on silica gel (EtOAc/hexanes 1:9) to yield 0.32 g of the desired product: Mp=149–154° C.; $^1$H NMR (DMSO-d$_6$) δ 9.76 (br s, 1 H), 7.62 (d, 1 H, J=9.2 Hz), 7.61 (d, 1 H, J=1.7 Hz), 7.14 (d, 1 H, J=2.6 Hz), 6.90 (s, 1 H), 6.86 (dd, 1 H, J=8.9 Hz, 2.6 Hz), 6.75–6.72 (m, 2H (protons overlapping)), 3.79 (s, 3 H), 2.45 (s, 3 H); MS 253 (M–H)$^-$.

2-(4-Hydroxy-2-methyl-phenyl)-benzofuran-5-ol 80

A mixture of the monomethyl ether 79 (0.27 g, 1.1 mmol) and Pyr-HCl was heated at 180° C. for 30–45 minutes. The reaction mixture was allowed to cool and partitioned between EtOAc and 2 N HCl aq and the EtOAc was washed with brine and dried over MgSO$_4$. The solution was filtered, concentrated and chromatographed on silica gel (EtOAc/hexanes 1:3): Mp=167–169° C.; $^1$H NMR (DMSO-d$_6$) δ 8.61 (s, 1 H), 8.11 (s, 1 H), 7.67 (d, 1 H, J=8.9 Hz), 7.33 (d, 1 H, J=8.7 Hz), 7.02 (d, 1 H, J=2.4 Hz), 6.82–6.78 (m, 4H (overlapping protons)), 2.50 (s, 3 H); MS 239 (M–H)$^-$.

5-Bromo-2-(4-methoxy-phenyl)-benzofuran 81

A solution of 4-Bromo-2-iodophenol [207115-22-8] (0.9 g, 3.0 mmol), 4-Methoxyphenylacetylene (0.43 g, 3.3 mmol), PdCl$_2$P(PH$_3$)$_2$ (70 mg), and CuI (50 mg) in DMF/Diethylamine (10 ml) was heated to 60° C. After 1 hr, the reaction was cooled and poured into water which was extracted with EtOAc. The organic layer was dried over MgSO$_4$ and concentrated to give a solid which was triturated with MeOH, filtered to give a solid (0.4 g, 45%): Mp=192–194° C.; $^1$H NMR (CDCl$_3$) δ 7.77 (d, 2 H, J=9.1 Hz), 7.66 (s, 1 H), 7.37–7.32 (m, 2 H), 6.98 (d, 2 H, J=9.1 Hz), 6.82 (d, 1 H, J=0.8 Hz), 3.87 (s, 3 H).

5-Chloro-2-(4-methoxy-phenyl)-benzofuran 82

A solution of 4-Chloro-2-Iodophenol [71643-66-8] (1.0 g, 3.9 mmol), 4-Methoxyphenylacetylene (0.53 g, 4.0 mmol), PdCl$_2$P(PH$_3$)$_2$ (70 mg), and CuI (50 mg) in DMF/Diethylamine (10 ml) was heated to 60° C. After 1 hr, the reaction was cooled and poured into water which was extracted with EtOAc. The organic layer was dried, concentrated to give a solid which was triturated with MeOH, filtered to give a solid (0.5 g, 50%): Mp=183–185° C.; $^1$H NMR (CDCl$_3$) δ 7.76 (d, 2 H, J=8.0 Hz), 7.50 (d, 1 H, J=1.6 Hz), 7.39 (d, 1 H, J=8.3 Hz), 7.20–7.18 (m, 1 H), 6.97 (d, 2 H, J=8.3 Hz), 6.82 (s, 1 H), 3.86 (s, 3 H).

5-Fluoro-2-(4-methoxy-phenyl)-benzofuran 83

A solution of 4-Fluoro-2-Idophenol [2713-29-3] (0.9 g, 3.8 mmol), 4-Methoxyphenylacetylene (0.53 g, 4.0 mmol), PdCl$_2$P(PH$_3$)$_2$ (70 mg), and CuI (50 mg) in DMF/Diethylamine (10 ml) was heated to 60° C. After 1 hr, the reaction was cooled and poured into water which was extracted with EtOAc. The organic layer was dried over MgSO$_4$, filtered and concentrated to give a solid which was triturated with MeOH, and filtered to give 83 as a solid;

5-tert-Butyl-2-(4-methoxy-phenyl)-benzofuran 84

A solution of 4-t-butyl-2-iodophenol [38941-98-9] (1.09 g, 3.6 mmol), 4-Methoxyphenylacetylene (0.53 g, 4.0 mmol), PdCl$_2$P(PH$_3$)$_2$ (70 mg), and CuI (50 mg) in DMF/Diethylamine (10 ml) was heated to 60° C. After 1 hr, the reaction was cooled and poured into water which was extracted with EtOAc. The organic layer was dried, concentrated to give a solid which was triturated with MeOH, filtered to give 84 as a solid.

5,7-Dichloro-2-(4-methoxy-phenyl)-benzofuran 85

A solution of 2,4-Dichloro-6-iodo-phenol [2040-83-7] (2.0 g, 6.9 mmol), 4-Methoxyphenylacetylene (0.91 g, 6.9 mmol), PdCl$_2$P(PH$_3$)$_2$ (0.15 g), and CuI (50 mg) in DMF/Diethylamine (26 ml) was heated to 60° C. After 1 hr, the reaction was cooled and poured into water which was extracted with EtOAc. The organic layer was dried over MgSO$_4$, filtered and concentrated to give a solid which was triturated with MeOH, filtered to give 85 as a solid (0.80 g, 42%): Mp=1.72–174° C.; $^1$H NMR (CDCl$_3$) δ 7.82 (d, 2 H, J=8.1 Hz), 7.41 (d, 1 H, J=1.8 Hz), 7.24 (d, 1 H, J=1.9 Hz), 7.00 (d, 2 H, J=8.8 Hz), 6.84 (s, 3 H), 3.87 (s, 3 H); MS 293/295 [M+H]$^+$ 5,7-Difluoro-2-(4-methoxy-phenyl)-benzofuran 86

A solution of 2,4-Difluoro-6-iodo-phenol (1.0 g, 3.9 mmol), 4-Methoxyphenylacetylene(0.53 g, 4.0 mmol), PdCl$_2$P(PH$_3$)$_2$ (70 mg), and CuI (50 mg) in DMF/Diethylamine (10 ml) was heated to 60° C. After 1 hr, the reaction was cooled and poured into water which was extracted with EtOAc. The organic layer was dried over MgSO$_4$, filtered and concentrated to give a solid which was triturated with MeOH and filtered to give 86 as a solid.

5,7-Dibromo-2-(4-methoxy-phenyl)-benzofuran 87

A solution of 2,4-Dibromo-6-iodo-phenol [53872-06-3] (0.7 g, 1.8 mmol), 4-Methoxyphenylacetylene (0.53 g, 4.0 mmol), PdCl$_2$P(PH$_3$)$_2$ (70 mg), and CuI (50 mg) in DMF/Diethylamine (10 ml) was heated to 60° C. After 1 hr, the reaction was cooled and poured into water which was extracted with EtOAc. The organic bayer was dried over MgSO$_4$, filtered and concentrated to give a solid which was triturated with MeOH and filtered to give 87 as a solid.

2-(4-Methoxy-phenyl)5-trifluoromethyl-benzofuran 88

A solution of 4-Trifluoro-2iodo-phenol (0.5 g, 1.7 mmol), 4-Methoxyphenylacetylene (0.26 g, 2.0 mmol), PdCl$_2$P(PH$_3$)$_2$ (70 mg), and CuI (50 mg) in DMF/Diethylamine (10 ml) was heated to 60° C. After 1 hr, the reaction was cooled and poured into water which was extracted with EtOAc. The organic layer was dried, concentrated to give a solid which was triturated with MeOH and filtered to give 88 as a solid.

4-(5-Bromo-benzofuran-2-yl)-phenol 89

A mixture of 81 (0.3 g, 1 mmol) and Pyridine HCl (5 g) was heated to 200° C. After 1 hr, the reaction was cooled and then diluted with water. The aqueous layer was extracted with EtOAc, dried over MgSO$_4$ and concentrated to give a solid. The solid was triturated with CH$_2$Cl$_2$ and filtered to give a solid (0.11 g, 39%); Mp=228–229° C.; $^1$H NMR (DMSO-d$_6$) δ 9.95 (br s, 1 H), 7.79 (d, 1 H, J=2.0 Hz), 7.74 (d, 2 H, J=8.8 Hz), 7.55 (d, 1 H, J=8.8 Hz), 7.39 (dd, 1 H, J=8.8 Hz, 2.4 Hz), 7.16 (s, 1 H), 6.88 (d, 2 H, J=8.8 Hz); MS 287/289[M−H]$^−$

4-(5-Chloro-benzofuran-2-yl)-phenol 90

A mixture of 82 (0.5 g, 1.9 mmol) and Pyridine HCl (10 g) was heated to 200° C. After 1 hr, the reaction was cooled and then diluted with water. The aqueous layer was extracted with EtOAc, dried over MgSO$_4$ and concentrated to give a solid. The solid was triturated with CH$_2$Cl$_2$ and filtered to give a solid (0.20 g, 47%); Mp=216–218° C.; $^1$H NMR (DMSO-d$_6$) δ 9.95 (br s, 1 H), 7.74 (d, 2 H, J=8.8 Hz),7.66 (d, 1 H, J=1.9 Hz), 7.59 (d, 1 H, J=8.8 Hz), 7.27 (dd, 1 H, J=8.8 Hz, 2.4 Hz), 7.17 (s, 1 H), 6.88 (d, 2 H, J=8.7 Hz); MS 243/245 [M−H]$^−$

4-(5-Fluoro-benzofuran-2-yl)-phenol 91

Compound 83 was treated with Pyridine HCl (5 g) and heated to 200° C. After 1 hr, the reaction was cooled and diluted with water. The aqueous layer was extracted with EtOAc, dried over MgSO4, filtered and concentrated to give a solid (0.11 g, 13%); Mp=202–204° C.; $^1$NMR (DMSO-d$_6$) δ 9.92 (br s, 1 H), 7.73 (d, 2 H, J=8.7 Hz), 7.58 (dd, 1 H, J=8.7 Hz, 4.4 Hz), 7.39 (dd, 1H J=8.8 Hz, 2.5 Hz), 7.17 (d, 1 H, J=1.0 Hz), 7.10–7.06 (m, 1 H), 6.88 (d, 2 H, J=8.8 Hz); MS 227 [M−H]$^−$

4-(5-tert-Butyl-benzofuran-2-yl)-phenol 92

Compound 84 was treated with Pyridine HCl (5 g) and heated to 200° C. After 1 hr, the reaction was cooled and diluted with water. The aqueous layer was extracted with EtOAc, dried over MgSO$_4$, filtered and the crude product was purified by column chromatography (eluant 25% EtOAc/hexanes) to give a solid (0.18 g, 17%); Mp=172–174° C.; $^1$H NMR (DMSO-d$_6$) δ 9.83 (s, 1 H), 7.70 (d, 2 H, J=8.9 Hz), 7.56 (d, 1 H, J=1.7 Hz), 7.45 (d, 1 H, J=9.0 Hz), 7.32 (dd, 1 H, J=9.0 Hz, 2.1 Hz), 7.11 (s, 1 H), 6.87 (d, 2 H, J=8.5 Hz); MS 265 [M−H]$^−$

4-(5,7-Dichloro-benzofuran-2-yl)-phenyl 93

A mixture of 85 (0.7 g, 2.4 mmol) and Pyridine HCl (10 g) was heated to 200° C. After 1 Hr, the reaction was cooled and diluted with water. The aqueous layer was extracted with EtOAc, dried and concentrated to give a solid which was triturated with MeOH, filtered to give a solid (0.5 g, 75%): Mp=184–186° C.; $^1$H NMR (DMSO-d$_6$) δ10.04 (s, 1 H), 7.77 (d, 2 H, J=8.3 Hz), 7.67 (t, 1 H, J=0.8 Hz), 7.48–7.46 (m, 1 H), 7.26 (s, 1 H), 6.90 (d, 2 H, J=8.2 Hz); MS 277/279 [M−H]$^−$

4-(5,7-Difluoro-benzofuran-2-yl)-phenol 94

Compound 86 was treated with Pyridine HCl (5 g) and heated to 200° C. After 1 hr, the reaction was cooled and diluted with water. The aqueous layer was extracted with EtOAc, dried, and the product was purified by column chromatography (eluent 25% EtOAc/hex) to give a solid (0.12 g, 13%): Mp=152–154° C.; $^1$H NMR (DMSO-d$_6$) δ 10.01 (br s, 1 H), 7.77 (d, 2 H, J=8.9 Hz), 7.32–7.25 (m, 3 H), 6.91 (d, 2 H, J=8.9 Hz); MS 245 [M−H]$^−$

4-(5,7-Dibromo-benzofuran-2-yl)-phenol 95

Compound 87 was treated with Pyridine HCl (5 g) and heated to 200° C. After 1 hr, the reaction was cooled and diluted with water. The aqueous layer was extracted with EtOAc, dried over. MgSO$_4$, and the product was purified by column chromatography (eluant 25% EtOAc/hexanes) to give a solid (0.12 g, 18%); Mp=203–205° C.; $^1$H NMR (DMSO-d$_6$) δ 10.04 (br s, 1 H), 7.83 (d, 1 H, J=1.5 Hz), 7.75 (d, 2 H, J=8.3 Hz), 7.68 (d, 1 H, J=2.0 Hz), 7.28 (s, 1H), 6.91 (d, 2 H, J=8.3 Hz); MS 365/367/369 [M−H]$^−$

4-(5-Trifluoromethyl-benzofuran-2-yl)-phenol 96

Compound 88 was treated with Pyridine HCl (5 g) and heated to 200° C. After 1 hr, the reaction was cooled and diluted with water. The aqueous layer was extracted with EtOAc, dried over MgSO4, and the product was purified by column chromatography (eluant 25% EtOAc/hexanes) to give the product as a solid: (0.025 g, 4.8%); MS 277 [M−H]$^−$ Synthesis of Compounds from Scheme 8

2-Iodo-4-methoxy-6-nitro-phenol 97

A solution of 4-Methoxy-2-nitrophenol (5 g, 29.6 mmol) in MeOH (100 mL) was cooled to 0° C. and treated with KOH (1.8 g, 32.6 mmol) followed by portionwise addition of I$_2$ (8.2 g, 32.6 mmol). The reaction was worked-up by quenching the excess I$_2$ by adding a 10% Na$_2$SO$_3$ aq solution. The MeOH was stripped off and 2 N HCl aq. was added and the aqueous extracted with EtOAc. The EtOAc was washed with saturated NaHCO₃, brine and dried over MgSO₄. The solution was concentrated and triturated twice with MeOH to yield 5 g of material that consisted of a 2:1 mixture of product to starting material that was used as is for the next step.

5-Methoxy-2-(4-methoxy-phenyl)-7-nitro-benzofuran 98

The 2-Iodo-4-methoxy-6-nitro-phenol 97 (1 g, 2.25 mmol based on 0.67 molar purity) in DMF/pyrrolidine (3 mL/3 mL) was treated with 4-methoxystyryne (0.45 g, 3.4 mmol), catalytic PdCl₂(PPh₃)₂ and catalytic CuI was heated at 60° C. until reaction was adjudged complete by TLC analysis (<1 h to completion). The reaction was worked up by partitioning between EtOAc and 2 N HCl aq. The EtOAc was washed with saturated NaHCO₃ aq, brine and dried over MgSO4. After filtering and concentrating, the product was purified by trituration with MeOH to give 0.57 g: Mp=141° C.

2-(4-Hydroxy-phenyl)-7-nitro-benzofuran-5-ol 99

A mixture of 98 (0.56 g) and Pyr-HCl and heated at 200° C. for 1 h (while occasionally adding more Pyr-HCl). The reaction was allowed to cool and then partitioned between 2 N HCl aq and EtOAc. A small amount of MeOH was added to facilitate the dissolution process. The organic layer was washed with saturated NaHCO₃ aq, brine, and dried over MgSO₄. Filtration, concentration and trituration of the pdt with CH₂Cl₂ yielded 0.44 g of the desired pdt which contained some inorganic impurities. The material was then chromatographeid on silica gel (MeOH/CH₂Cl₂ 1:19 to MeOH/CH₂Cl₂ 1:9) to yield 0.24 g of 99: Mp=236–2372° C.; ¹H NMR (DMSO-d₆) δ 10.06 (br s, 1 H), 7.73 (d, 2 H, J=8.3 Hz), 7.46 (dd, 1 H, J=2.4 Hz, 0.7 Hz), 7.38 (dd, 1 H, J=2.3 Hz, 0.7 Hz), 7.28 (s, 1 H), 6.93 (d, 2 H, J=8.3 Hz); MS 270 (M–H)⁻.

7-Amino-2-(4-hydroxy-phenyl)-benzofuran-5-ol 100

A solution of 99 (0.070 g, 0.29 mmol) in AcOH/MeOH was stirred under an atmosphere of H₂ in the presence of 10% Pd/C. After TLC analysis indicated reaction was over, the reaction was filtered through Celite, concentrated and chromatographed on silica gel (MeOH/CH₂Cl₂ 1:9) to yield 25 mg of the desired product: Mp=251–254° C.; ¹H NMR (DMSO-d₆) δ 9.76 (br s, 1 H), 8.65 (br s, 1 H), 7.71 (d, 2 H, J=8.5 Hz), 6.86 (s, 1 H), 6.84 (d, 2 H, J=8.7 Hz), 6.09 (d, 1 H, J=1.9 Hz), 6.02 (d, 1 H, J=1.9 Hz), 5.21 (s, 2 H); MS 242 (M+H)⁺.

1-(2-Bromo-4-methoxy-phenyl)-2-(2,5-dimethoxy-phenyl)-ethanone 101

3-Br Anisole (5 g, 27 mmol) and 2,5-dimethoxy phen-acetyl chloride (6.8 g, 32.4 mmol) in dichloroethane (0.2 L) was cooled to 0° C. and treated with AlCl₃ (4.3 g, 32 mmol). The reaction was allowed to warm to rt and then worked up by carefully adding 2 N HCl aq and partitioning the reaction mixture. The organic layer was washed with NaHCO₃ aq, brine and dried over MgSO₄. After filtering and concentrating, the residue was chromatographed on silica gel (1:19 EtOAc/hexanes) to yield the desired pdt (1.45 g) as the second reaction product to elute from the column: Mp=76–79° C.

2-(2-Bromo-4-hydroxy-phenyl)-benzofuran-5-ol 102

Compound 101 (1.25 g, 3.4 mmol) was heated at 200° C. with a large excess of Pyr-HCl and followed by TLC for reaction completion (approx 30 min to 1 h). The reaction mixture was allowed to cool to rt and then partitioned between 2 N HCl aq and EtOAc. The organic layer was washed with saturated NaHCO₃ aq, brine, and then dried over MgSO₄. After filtering, the reaction mixture was concentrated and chromatographed on silica gel (1:1 EtOAc/hexanes) to yield 0.96 g of the desired pdt: Mp=195° C.; ¹H NMR (DMSO-d₆) δ 10.33 (br s, 1 H), 9.23 (br s, 1 H), 7.70 (d, 1 H, J=8.6 Hz); 7.37 (d, 1 H, J=8.8 Hz), 7.21 (s, 1 H), 7.16 (d, 1 H, J=2.4 Hz), 6.97 (d, 1 H, J=2.4 Hz), 6.92 (dd, 1 H, J=8.7 Hz, 2.4 Hz), 6.75 (dd, 1 H, J=8.8 Hz, 2.4 Hz); MS 303 (M–H)⁻.

2-(5-Hydroxy-biphenyl-2-yl)-benzofuran-5-ol 103

Compound 102 (0.2 g, 0.69 mmol) in a solution consisting of Tol/EtOH/2M Na₂CO₃ aq (5/1/5) was treated with phenylboronic acid (0.12 g, 1.0 mmol) and cat Pd(PPh₃)₄ and heated to reflux until TLC analysis indicated complete reaction. The reaction was worked up by acidifying with 2 N HCl aq and extracting with EtOAc. The organic layer was washed with saturated NaHCO₃ aq, brine, and dried over MgSO₄. After filtering and concentrating, the crude material was chromatographed on silica gel (1:9 EtOAc/hexanes to 4:6 EtOAc/hexanes) and then triturated with hexanes to yield 0.10 g of the desired material: Mp.=167–709° C.; ¹H NMR (DMSO-d₆) δ 9.98 (br s, 1 H), 9.07 (br s, 1 H), 7.68 (d, 1 H, J=8.5 Hz), 7.4–7.38 (m, 3 H), 7.26–7.22 (m, 2 H), 7.18 (d, 1 H, J=8.7 Hz), 6.90 (dd, 1 H, J=8.5 Hz, 2.5 Hz), 6.72 (d, 1 H, J=2.5 Hz), 6.67 (d, 1 H, J=2.3 Hz), 6.62 (dd, 1 H, J=8.7 Hz, 2.4 Hz), 5.81 (s, 1 H).

2-(4-Benzyloxy-5-hydroxy-biphenyl-2-yl)-benzofuran-5-ol 104

Compound 102 (0.23 g, 7.9 mmol) in a solution consisting of Tol/EtOH/2M Na₂CO₃ aq (15 mL/2 mL/15 mL) was treated with 4-benzloxy phenylboronic acid (0.12 g, 1.0 mmol) and cat Pd(PPh₃)₄ and heated to reflux until TLC analysis indicated complete reaction. The reaction mixture was treated with 2 N HCl aq and extracted with EtOAc. The EtOAc layer was washed with saturated NaHCO₃ aq, brine and dried over MgSO₄. After filtration, the residue was chromatographed on silica gel (1:4 EtOAc/hexanes) to yield the desired product as an orange solid. The orange solid thus obtained was triturated with CH₂Cl₂ to yield the pdt (2.4 g) as a white solid: Mp=186–187° C.; ¹H NMR (DMSO-d₆) δ 9.90 (br s, 1 H), 9.05 (br s, 1 H), 7.65 (d, 1 H, J=8.5 Hz), 7.51–7.31 (m, 5 H), 7.19 (d, 1 H, J=8.5 Hz), 7.17 (d, 2 H, J=8.6 Hz), 7.02 (d, 2 H, J=8.7 Hz), 6.86 (dd; 1 H, J=8.5 Hz, 2.4 Hz), 6.70 (d, 2 H, J=1.8 Hz), 6.63 (dd, 1 H, J=8.7 Hz, 2.4 Hz), 5.86 (s, 1 H), 5.14 (s, 2 H); MS 407 (M–H)⁻.

6-(5-Hydroxy-benzofuran-2-yl)-biphenyl-3,4'-diol 105

A solution of 104 (0.13 g, 0.32 mmol) in MeOH (10 mL) was treated with. 0.2 g 10% Pd/C and. cyclohexadiene (1 mL) and stirred at rt for 24 h. The reaction was filtered through a bed of Celite, concentrated and chromatographed on silica gel (1:1 EtOAc/hexanes) and the product was obtained as an oil which crystallized upon addition of CH₂Cl₂ to yield 48 mg of yellowish needles: Mp=238–239°

C.; ¹H NMR (DMSO-d$_6$) δ 9.87 (br s, 1 H), 9.54 (br s, 1 H), 9.08 (br s, 1 H), 7.64 (d, 1 H, J=8.5 Hz), 7.21 (d, 1 H, J=8.7 Hz), 7.05 (d, 2 H, J=8.4 Hz), 6.84 (dd, 1 H, J=8.5 Hz, 2.5 Hz), 6.76 (d, 2 H, J=8.5 Hz), 6.69 (dd, 2 H, J=6.6 Hz, 2.4 Hz), 6.63 (dd, 1 H, J=8.7 Hz, 2.4 Hz), 5.84 (s, 1 H); MS 317 (M–H)⁻.

Synthesis of Compounds from Scheme 9

2-[5-Hydroxy-4'-(2-pyrrolidin-1-yl-ethoxy)-biphenyl-2-yl]-benzofuran-5-ol 108

Compound 104 (2.6 g, 6.4 mmol) in DMF (30 mL) was treated with TBS-Cl (2.4 g, 16 mmol) and imidazole (2.2 g, 32 mmol) and stirred overnight at rt. The reaction was worked up by diluting with water and washing with brine and drying over MgSO$_4$. After filtering, the reaction was concentrated to yield 106 as an oil and used as is for the next step. This material was dissolved in THF/EtOH and treated with 10% Pd/C and hydrogenated under an atmosphere of H$_2$ for 48 h. The reaction mixture was filtered through Celite and concentrated to yield 2.9 g of a viscous foam 107 that was used as is for the next step. A solution consisting of 107 (1.25 g, 2.3 mmol) in DMF (25 mL) was treated with K$_2$CO$_3$ (0.64 g, 4.6 mmol) and 2-chloroethyl pyrrolidine HCl (0.49 g, 8 mmol) and heated at 50° C. for 1 h. Excess TBAF (1M in THF) was added and the reaction was allowed to stir for 15 minutes at rt. The reaction mixture was treated with a saturated NH$_4$Cl aq solution followed by saturated NaHCO$_3$ aq. The reaction was extracted with EtOAc and the EtOAc layer washed with brine and dried over MgSO$_4$. After filtration and concentration, the oily residue was chromatographed on silica gel (MeOH/CH$_2$Cl$_2$ 0:100 to MeOH/CH$_2$Cl$_2$ 5:95). A few clean fractions were taken from the column and concentrated down to yield an oil, which was taken up in MeOH and treated with a 1 N HCl in ether solution and the product precipitated out and was collected by filtration to give 0.065 g of 108 as the hydrochloride salt: Mp=266–269° C.; ¹H NMR (DMSO-d$_6$) δ 10.18 (br s, 1 H), 9.60 (s, 1 H) 9.13 (s, 1 H), 7.79 (d, 1 H, J=8.7 Hz), 7.24 (d, 1 H, J=8.7 Hz), 7.13–7.08 (m, 3 H), 6.93 (d, 1 H, J=2.6 Hz), 6.79 (d, 2 H, J=8.5 Hz), 6.74 (d, 1 H, J=2.4 Hz), 6.66 (dd, 1 H, J=8.8 Hz, 2.5 Hz), 5.94 (s, 1 H), 4.41 (t, 2 H, J=4.4 Hz), 3.59 (m, 4 H), 3.14 (m, 2 H), 2.1–1.9 (m, 4 H); MS 414 (M–H)⁻.

2,2-Dimethyl-propionic acid 2-[4-(2,2-dimethyl-propionyloxy)-phenyl]-benzofuran-5-yl ester 109

A solution of 75 (8.2 g, 36.3 mmol) in CH$_2$Cl$_2$/Pyr was treated with pivaloyl chloride (9.63 g, 79.9 mmol) and stirred at rt until TLC indicated that the reaction was complete. The reaction was worked up by diluting with additional CH$_2$Cl$_2$ and washing with 2 N HCl aq. The CH$_2$Cl$_2$ layer was washed with satd NaHCO$_3$ aq, brine and dried over MgSO$_4$. Filtration and concentration yielded 9.3 g of the crude solid that was used as is for the next reaction.

1-[5-Hydroxy-2-(4-hydroxy-phenyl)-benzofuran-3-yl]-ethanone 110

A solution of the bis-pivaloylate 109 (1 g, 2.54 mmol) in CH$_2$Cl$_2$ was treated with acetyl chloride (0.22 g, 2.8 mmol) was treated with AlCl$_3$ (0.36 g, 2.8 mmol) and stirred at rt overnight. The reaction was worked up by adding EtOAc, washing with 2 N HCl aq, saturated NaHCO$_3$ aq and drying over MgSO$_4$. After filtering and concentrating, the residue was chromatographed on silica gel (EtOAc/hexanes 1:4 to EtOAc/hexanes 1:1) to yield the product which was promptly dissolved in MeOH/THF/2 N NaOH aq and warmed until TLC analysis indicated that the hydrolysis of the pivalate esters was completed. The reaction was concentrated to remove the organic solvents and the residue aqueous was acidified with 2 N HCl aq and extracted with EtOAc. The EtOAc extract was washed with saturated NaHCO$_3$ solution, brine and dried over MgSO$_4$. After filtration and concentration, the residue was chromatographed on silica gel (EtOAc/hexanes 1:4 to EtOAc/hexanes 1:1) to yield 90 mg of the desired pdt: Mp=243–251° C.; ¹H NMR (DMSO-d$_6$) δ 10.08 (br s, 1 H), 9.40 (br s, 1 H), 7.63 (d, 2 H, J=8.8 Hz), 7.43 (d, 1 H, d=9.3 Hz), 7.41 (d, 1 H, J=2.4 Hz), 6.92 (d, 2 H, J=8.8 Hz), 6.80 (dd, 1 H, J=8.8 Hz, 2.4 Hz), 2.26 (s, 3 H).

1-[5-Hydroxy-2-(4-hydroxy-phenyl)-benzofuran-3-yl]-ethanone oxime 111

Ketone 110 (1.9 g, 7.1 mmol) was dissolved in a solution of EtOH/Pyr (50 mL/10 mL) and treated with NH$_2$OH—HCl (0.5 g, 7.2 mmol) and heated at reflux until all of the starting material was consumed by TLC analysis. The reaction was worked up by concentrating down and partitioning the residue between EtOAc and 2 N HCl aq, washing the EtOAc layer with saturated NaHCO$_3$ aq, brine and drying over MgSO$_4$. The solution was then filtered, concentrated and chromatographed on silica gel (1:4 EtOAc/hexanes) and the product obtained triturated with CH$_2$Cl$_2$ to yield 0.131 g of the pure oxime. Stereochemistry of the oxime was tentatively defined as cis since no NOE effect between the oxime hydroxyl proton and the adjacent methyl group could be observed: Mp=217° C.; ¹H NMR (DMSO-d$_6$) δ 11.27 (s, 1 H), 9.94 (br s, 1 H), 9.23 (br s, 1 H), 7.51 (d, 2 H, J=8.8 Hz), 7.36 (d, 1 H, J=8.3 Hz), 7.03 (d, 1 H, J=2.4 Hz), 6.88 (d, 2 H, J=8.8 Hz), 6.74 (dd, 1 H, J=8.8 Hz, 2.4 Hz), 1.99 (s, 3 H).

3-(1-Hydroxy-ethyl)-2-(4-hydroxy-phenyl)-benzofuran-5-ol 113

The bis-acetyl ester 112 (prepared by acetylation of 110, in pyridine and acetic anhydride) (0.15 g, 0.43 mmol) in EtOH/THF (10 mL5 mL) was treated. with NaBH$_4$ (0.1 g, 2.6 mmol) and stirred at rt overnight. The reaction was then treated with 2 N NaOH and stirred fore an additional time until TLC showed that the acetate hydrolysis had gone to completion. The reaction mixture was neutralized with saturated NH$_4$Cl aq and the solution concentrated. The aqueous residue was extracted with EtOAc and the EtOAc layer washed with brine, dried over MgSO$_4$, filtered, concentrated and chromatographed on silica gel (EtOAc/hexanes 1:4 to EtOAc/hexanes 1:1) to yield 0.040 g of the pdt: Mp=177–182° C.; ¹H NMR (DMSO-d$_6$) δ 9.84 (br s, 1 H), 9.09 (s, 1 H), 7.49 (d, 2 H, J=8.8 Hz), 7.30 (d, 1 H, J=8.8 Hz), 7.20 (d, 1 H, J=2.4 Hz), 6.90 (d, 2 H, J=8.8 Hz), 6.69 (dd, 1 H, J=8.8 Hz, 2.4 Hz), 5.22 (d, 1 H, J=3.4 Hz), 5.10–5.06 (m, 1 H), 1.53 (d, 3 H, J=6.3 Hz); MS 269 (M–H)⁻.

Synthesis of Compounds from Scheme 10

2-[5-Methoxy-2-(4-methoxy-phenyl)-benzofuran-7-yl]-propan-2-ol 115

Ester 114 (1.0 g, 3.2 mmol)was treated with Methyl Lithium (10 ml of 1.0 M) in THF (25 ml) at –78° C. After warming to rt over 2 hr, the reaction was quenched with 2NHCl and extracted with EtOAc. The EtOAc was dried concentrated and the product was purified by column chromatography on silica gel (20% EtOAc/Hexane) to give 115 as an oil (0.43 g, 43%).

7-Isopropenyl-5-methoxy-2-(4-methoxy-phenyl) benzofuran 116

2-[5-Methoxy-2-(4-methoxy-phenyl)-benzofuran-7-yl]-propan-2-ol 115 (0.4 g, 1.3 mmol) and Burges Reagent (0.4 g, 1.7 mmol) in THF (10 ml) were heated to reflux. After 30 min, the reaction was cooled, concentrated and the product was purified by column chromatography on silica gel (10% Et OAc/Hexane) to give 116 as a solid (0.29 g, 77%).

7-Isopropyl-5-methoxy-2-(4-methoxy-phenyl)-benzofuran 117

7-Isopropenyl-5-methoxy-2-(4-methoxy-phenyl)-benzofuran 116 (0.28, 0.9 mmol) was hydrogenated over an atmosphere of hydrogen with 10% Pd/C (0.05 g) in EtOH/THF (10 ml). After 2 hr, the reaction was filtered through celite and concentrated to give 117 as a solid (0.27 g, 95%).

2-(4-Hydroxy-phenyl)-7-isopropyl-benzofuran-5-ol 118

7-Isopropyl-5-methoxy-2-(4-methoxy-phenyl)-benzofuran 117 (0.26 g, 0.88 mmol) and Pyridine HCl (5 g) were heated to 200° C. After 1 hr, the reaction was cooled, diluted with water and extracted with EtOAc. The organic layer was dried over MgSO$_4$, concentrated and the product was purified by column chromatography on silica gel (25% EtOAc/hexane) to give 118 as a solid (0.80 g, 34%): Mp=192–194° C.; $^1$H NMR (DMSO-d$_6$) δ 9.81 (br s, 1 H), 9.03 (br s, 1 H), 7.68 (d, 2 H, J=8.2 Hz), 6.98 (s, 1 H), 6.86 (d, 2 H, J=8.1 Hz), 6.69 (d, 1 H, J=1.4 Hz), 6.54 (d, 1 H, J=1.9 Hz), 3.31 (m, 1 H), 1.32 (d, 6 H, J=6.9 Hz); MS 269 (M+H)$^+$

5-Hydroxy-2-(4-hydroxy-phenyl)-benzofuran-7-carboxylic acid methoxy-methyl-amide 119

To a solution of acid 24 (0.35 g, 1.3 mmol), DMAP (0.5 g, 4.1 mmol), N,O Dimethylhydroxyl amine HCl (0.5 g, 5.1 mmol) in DMF (15 ml) was added EDCI (0.5 g, 2.6 mmol) and the reaction was stirred at rt for 1 hr. The reaction was then poured into 2N HCl and extracted with EtOAc, The EtOAc was dried, concentrated, and the resulting solid was triturated with CH$_2$Cl$_2$ and collected by filtration to give 119 as a white solid (0.22 g, 55%): Mp=125–127° C.; $^1$NMR (DMSO-d$_6$) δ 9.88 (br s, 1 H), 9.44 (s, 1 H), 7.65(d, 2 H, 8.6 Hz), 7.08 (br s, 1 H), 6.97 (d, 1 H, J=2.3 Hz), 688 (d 2 H, J=8.6 Hz), 6.71 (d, 1 H, J=2.6 Hz), 3.59 (s, 3 H), 3.30 (s. 3 H): MS 312[M–H]$^-$

5-Hydroxy-2-(4hydroxy-phenyl)-benzofuran-7-carbaldehyde 120

To a cooled (0° C.) solution of 119 (0.18 g, 0.58 mmol) in THF (10 ml) was added LiAlH$_4$ (1.5 ml of 1.0 M in THF) dropwise. After stirring for 30 min, the reaction was quenched with 2N HCl and partitioned between 2N HCl and EtOAc. The EtOAc was separated, dried, and concentrated. The product was purified by column chromatography on silica gel (30% Et OAc/Hex) to give 120 as a yellow solid (0.075 g, 51%); Mp=261–263° C.; $^1$H NMR (DMSO-$_6$) δ 10.36 (s, 1 H), 9.79 (s, 1 H), 9.77 (s, 1 H), 7.76 (d, 2 H, J=8.5 Hz), 7.25 (d, 1 H, J=2.0 Hz), 7.17 (s, 1 H), 7.12 (d, 1 H, J=2.1 Hz), 6.88 (d, 2 H, J=8.5 Hz); MS 255 (M+H)$^+$

5-Methoxy-2-(4-methoxy-phenyl)-benzofuran-7-carboxylic acid methoxy-methyl-amide 121

A solution of 23 (1.7 g, 5.7 mmol), N,O Dimethylhydroxyamine HCl (1.7 g, 17.1 mmol), DMAP (2.1 g, 17.1 mmol), and EDCI (1.9 g, 10 mmol) in DMF (30 ml) was stirred at rt for 1 hr. The reaction was then poured into 2 NHCl and extracted with EtOAc which was dried over MgSO$_4$, concentrated, and the product was purified by column chromatography on silica gel (30% Et OAc/Hex) to give 121 as a solid (1.4 g, 74%); Mp=109–111° C.; $^1$H NMR (CDCl$_3$) δ 7.77 (d, 2 H, J=8.7 Hz), 7.09 (d, 1 H, J=2.4 Hz), 6.99–6.95 (m, 3 H), 6.84 (s, 1 H), 3.86 (s, 6 H), 3.69 (s, 3 H), 3.40 (s, 3 H); MS 342 (M+H)$^+$

1-[5-Methoxy-2-(4-methoxy-phenyl)-benzofuran-7-yl]-ethanone 122

To a cooled (–78° C.) solution of 121 (0.6 g, 1.7 mmol) in THF (10 ml) was added Methyl lithium (3.4 ml of 1.0 M in THF) and the reaction was stirred for 1 hr. The solution was then poured into 2 N HCl and extracted with EtOAc which was separated, dried over MgSO$_4$, and concentrated to give a solid which was triturated with MeOH and collected by filtration to give 122 as a white solid (0.35 g, 67%); $^1$H NMR (CDCl$_3$) δ 7.78(d, 2 H, J=8.7 Hz), 7.44 (d, 1 H, 2.6 Hz), 7.24 (s, 1 H), 6.99 (d, 2 H, J=8.7 Hz), 6.89 (s, 1 H), 3.89 (s, 3 H), 3.88 (s, 3 H), 2.96 (s, 3 H).

1-[5-Hydroxy-2-(4-hydroxy-phenyl)-benzofuran-7-yl]-ethanone 123

A mixture of 122 (0.37 g, 1.3 mmol) and Pyridine HCl (10 g).was heated. to 200° C. After 1 hr, the reaction was cooled, diluted with water and extracted with EtOAc. The EtOAc layer was dried over MgSO$_4$, concentrated and the product was purified by column chromatography (50% Et OActHex) to give 123 as a solid (0.25 g, 74%): Mp=274–276° C., $^1$H NMR (DMSO-$_6$) δ 9.96 (br s, 1 H), 9.52 (br s, 1 H), 7.74 (d, 2 H, J=8.4 Hz), 7.17–7.16 (m, 3 H), 6.89 (d, 2 H, J=8.4 Hz),2.64 (s, 3 H); MS 267 (M–H)$^-$ Synthesis of Compounds from Scheme 11

1-[5-Hydroxy-2-(4-hydroxy-phenyl)-benzofuran-7-yl]-propan-1-one 124

To a cooled (0° C.) solution of 121 (0.7 g, 2.0 mmol) in THF (15 ml) was added Ethyl Magnesium Bromide (6.0 ml of 1.0 M in ether) and the reaction was allowed to warm to rt over 2 hr. The reaction was then poured into 2N HCl and extracted with EtOAc. The EtOAc layer was dried concentrated and the product was purified by column chromatography (15% Et OAc/Hex) to give a solid (0.31 g). To the solid was added Pyridine HCl (7 g) and the mixture was heated to 200° C. After 1 Hr, the reaction was cooled, diluted with water and extracted with EtOAc. The EtOAc layer was dried, concentrated, and the product was purified by column chromatography on silica gel (50% EtOAc/Hex) to give 124 as a solid (0.15 g, 26%): Mp=257–260° C.; $^1$NMR (DMSO-d$_6$) δ 9.79(br s, 1 H), 9.70(br s, 1 H), 7.76 (d, 2 H, J=8.1 Hz), 7.19–7.15 (m, 3 H), 6.89 (d, 2 H, J=8.1 Hz), 3.32–3.27 (m, 2 H), 1.18 (t, 3 H, J=7.1 Hz); MS 281 [M–H]$^-$

2-(2,5-Dimethoxy-phenyl)-1-(3-fluoro-4-methoxy-phenyl)-ethanone 125

A solution of 3-F anisole (2 g, 16 mmol) and 2,5-dimethoxyphenacetyl chloride in dichloroethane (50 mL) was treated with $AlCl_3$ (2.3 g, 18 mmol) and stirred at rt until TLC analysis indicated reaction was complete. The reaction was worked up by adding a 2 N HCl aq solution to the reaction (slowly) and washing with saturated $NaHCO_3$ aq, brine chromatographed on silica gel (EtOAc/hexanes 1:4) to yield 1 gram of the acylated intermediate as well as an isomer as an oily solid that was used as is for the next reaction step.

2-(3-Fluoro-4-hydroxy-phenyl)-benzofuran-5-ol 126

The ketone 125 (1 g, 3.3 mmol) was heated with pyr-HCl at 180–200° C. until TLC indicated reaction completion. The reaction was worked up by partitioning between 2 N HCl aq and EtOAc and washing the EtOAc with saturated $NaHCO_3$, brine, and drying over $MgSO_4$. The solution was filtered, concentrated and chromatographed on silica gel to yield 0.48 g of impure pdt. The product thus obtained was recrystallized from EtOAc/hexanes to yield desired product plus a small amt of unidentified impurity: Mp=218–222° C.; $^1$H NMR (DMSO-$d_6$) δ 10.39 (s, 1 H), 9.20 (s, 1 H), 7.74 (t, 1 H, J=8.7 Hz), 7.37 (d, 1 H, J=8.8 Hz), 6.96–6.94 (m, 2 H), 6.79–6.70 (m, 3 H); MS 243 (M–H)$^-$

4-(5-Methoxy-benzofuran-2-yl)-benzoic acid methyl ester 127

A solution of 5-Methoxy-benzofuran-2-boronic acid (1.9 g, 10 mmol), Methyl 4-iodobenzoate (2.61 g, 10 mmol), Pd(Ph$_3$)$_4$ (0.25 g), and 2M NaCO$_3$ (10 ml) in toluene (40 ml) and EtOH (10 ml) was heated to reflux. After 2 hr, the reaction was cooled and the organic layer was separated dried, and concentrated to give a solid. The solid was triturated with MeOH, filtered to give 127 (0.90 g, 32%) which was used without further purification or characterization for the next step.

4-(5-Hydroxy-benzofuran-2-yl)-benzoic acid 128

A mixture of 4-(5-Methoxy-benzofuran-2-yl)-benzoic acid methyl ester (0.5 g, 1.8 mmol) and Pyridine HCl (5 g) was heated to 200° C. After 2 hr, the reaction was cooled and poured into water and extracted with EtOAc. The EtOAc layer was dried over $MgSO_4$, concentrated and the product was purified by column chromatography on silica gel (75% EtOAc/hex) to give a solid (0.21 g, 47%): $^1$H NMR (DMSO-$d_6$) δ 13.07 (br s, 1 H), 9.29 (br s, 1 H), 8.02 (d, 2 H, J=8.1 Hz), 7.97 (d, 2 H, J=8.7 Hz), 7.46 (m, 2 H), 6.97 (d, 1 H, J=2.9 Hz), 6.79 (dd, 1 H, J=9.3 Hz, 2.9 Hz); MS 253 (M–H)$^-$

2-(4-Hydroxymethyl-phenyl)-benzofuran-5-ol 129

To a solution of 128 (0.15 g, 0.6 mmol), in THF (20 ml) was added BH$_3$ (3 ml of 1.0 M in THF) and the reaction was heated to reflux for 3 hr. The reaction was then cooled and poured into 2N HCl and extracted with EtOAc. The EtOAc was dried over $MgSO_4$, filtered and concentrated and triturated with $CH_2Cl_2$ and filtered to give 129 as a solid (0.08 g, 57%); $^1$H NMR (DMSO-$d_6$) δ 9.21 (br s, 1 H), 7.82 (d, 2 H, J=8.1 Hz), 7.43–7.38 (m, 3 H), 7.24 (s, 1 H), 6.92 (d, 1 H, J=2.1 Hz), 6.73 (dd, 1 H, J=8.5 Hz, 2.6 Hz), 5.28 (t, 1 H, J=5.7 Hz), 4.54 (d, 2 H, J=5.5 Hz); MS 239 (M–H)$^-$.

Synthesis of Compounds from Scheme 12

4-Bromo-2-(4-hydroxy-phenyl)-benzofuran-5-ol 130

A solution of 75 2-(4-Hydroxy-phenyl)-benzofuran-5-ol (0.65 g, 2.9 mmol) in CH$_3$CN (40 mL) was treated with K$_2$CO$_3$ (1 g, 7.1 mmol) followed by portionwise addition of NBS (0.36 g, 2.0 mmol). After stirring for approximately 30 minutes, the reaction was worked up by addition of 2 N HCl followed by 10% Na$_2$SO$_3$aq. and then the CH$_3$CN was stripped off. The aqueous layer was extracted with EtOAc and washed with brine and dried over MgSO$_4$. The reaction mixture was concentrated and chromatographed on silica gel (EtOAc/hexanes; 1:4): Mp 196–198° C.; $^1$H NMR (DMSO-$d_6$) δ 9.93 (br s, 2 H), 7.76 (d, 2 H, J=8.5 Hz), 7.40 (d, 1 H, J=8.7 Hz), 7.04 (s, 1 H), 6.87 (dd, 2 H, J=9.0 Hz, 3.1 Hz); MS 305/307 (M+H)$^+$.

4-Chloro-2-(4-hydroxy-phenyl)-benzofuran-5-ol 131

Prepared analogously to 130 except that NCS was used instead of NBS: Mp=210–214° C.; $^1$H NMR (DMSO-$d_6$) 9.90 (br s, 1 H), 7.76 (d, 2 H, J=8.5 Hz), 7.13 (s, 1 H), 6.89 (d, 1 H, J=8.4 Hz), 6.87 (d, 2 H, J=8.5 Hz).

2-(4-Hydroxy-phenyl)-4-methoxy-benzofuran-5-ol 132

A solution of 4-bromo-2-(4-Hydroxyphenyl)-benzofuran-5-ol 130 (0.100 g, 0.32 mmol) and copper (I) bromide (0.047 g, 0.32 mmol) in DMF (4 mL) was treated with sodium methoxide (0.73 mL, 3.2 mmol, 25% by weight in MeOH) and heated at 150° C. for three hours under a nitrogen atmosphere; The reaction was quenched at room temperature with 1 N HCl and extracted with ethyl acetate (3×). The combined organic extracts were washed once with a saturated sodium bicarbonate solution, then dried over magnesium sulfate and filtered. Then the material was purified by column chromatography using 30% ethyl acetate in hexane as the eluent to yield 132 (0.030 g, 36.6%) as a brown solid: Mp. 165–1.68° C.; $^1$H NMR (DMSO-$d_6$) δ 7.72 (d, 2 H, J=8.6 Hz), 7.23 (s, 1 H), 7.1 (d, 1H J=8.7 Hz), 6.86 (d, 2 H, J=8.6 Hz, 6.76 (d, 1 H, J=8.6 Hz), 3.94 (s, 3 H); MS 257 (M+H)$^+$.

4-Bromo-5-methoxy-2-(4-methoxy-phenyl)-benzofuran 33

4-Bromo-2-(4-hydroxyphenyl)-benzofuran-5-ol 130 (0.601 g, 1.97 mmol) was taken into 25 mL DMF along with potassium carbonate (2.72 g, 19.7 mmol) and iodomethane (2.45 mL, 39.4 mmol). The mixture was heated overnight at 50° C. under a nitrogen atmosphere. The solution was filtered and the filtrate was diluted with ethyl acetate and washed with water (3×), dried over magnesium sulfate filtered and concentrated. The resulting material was purified by column chromatography on silica gel using 10% ethyl acetate in hexane as the eluent to yield the desired product (0.607 g, 92.5%) as a white solid: Mp. 115–117° C.; $^1$H NMR (DMSO-$d_6$) δ 7.92 (d, 2 H, J=8.8 Hz), 7.60 (d, 1 H, J=8.6 Hz), 7.22 (s, 1 H), 7.09 (d, 1 H, J=8.9 Hz), 7.07 (d, 2 H, J=8.8 Hz), 3.88 (s, 3 H), 3.83 (s, 3 H); MS 333/335 (M+H)$^+$.

5-Methoxy-2-(4-methoxy-phenyl)-benzofuran-4-carbonitrile 134

4-Bromo-5-methoxy-2-(4-methoxyphenyl)-benzofuran 133 (0.258 g, 0.77 mmol) was taken into 20 mL of DMF along with copper (I) cyanide (0.173 g. 1.94 mmol) and heated at reflux for three hours. Additional copper (I) cyanide was added several times to complete the reaction. The reaction was filtered through a cotton plug that was then washed several times with ethyl acetate. The filtrate was diluted with additional ethyl acetate and then washed with water (2×), brine (1×), dried over magnesium sulfate, filtered and concentrated. The resulting material was purified by column chromatography on silica gel using 10% ethyl acetate in hexanes as the eluent to yield the desired compound (0.133 g, 61.8%) as a white solid: Mp. 120–122° C.; $^1$H NMR (DMSO-d$_6$) δ 7.96 (d, 2 H, J=8.8 Hz), 7.92 (d, 1 H, J=9.1 Hz), 7.91 (s, 1 H), 7.14 (d, 1 H, J=9.1 Hz), 7.09 (d, 2 H, J=8.9 Hz), 3.95 (s, 3 H), 3.83 (s, 3 H); MS 280 (M+H)$^+$.

5-Hydroxy-2-(4-hydroxy-phenyl)-benzofuran-4-carbonitrile 135

5-Methoxy-2-(4-methoxyphenyl)-benzofuran-4-carbonitrile 134 (0.088 g, 0.31 mmol) was placed in a sealed tube along with pyridine hydrochloride (enough to fill the volume of the tube by one-half) and heated at 200° C. for 2.5 hours. The reaction was dissolved into a mixture of ethyl acetate and 1 N HCl. The layers were separated and the aqueous layer was extracted with ethyl acetate (2×). The combined organics was washed with 1N HCl (1×), water (1×) and then dried over magnesium sulfate, filtered and concentrated. The resulting material was purified by column chromatography, using 40% ethyl acetate in hexanes as the eluent to yield the desired product 135 (0.066 g, 84.7%) as a light brown solid: Mp>230° C.; $^1$H NMR (DMSO-d$_6$) δ 10.89 (s, 1 H), 10.03 (s, 1 H), 7.82 (d, 2 H, J=8.6 Hz), 7.72 (d, 1 H, J=8.9 Hz), 7.27 (s, 1 H), 6.90 (d, 2 H, J=8.6 Hz), 6.88 (d, 1 H, J=8.9 Hz).

5-Methoxy-2-(4-methoxy-phenyl)-4-methyl-benzofuran 136

4-Bromo-5-methoxy-2-(4-methoxyphenyl)-benzofuran 133 (0.282 g, 0.85 mmol) was taken into 20 mL of THF and cooled to 0° C. Then butyllithium (0.68 mL of a 2.5M solution in THF, 1.7 mmol) was added dropwise and allowed to stir for 20 minutes. Then TMEDA (0.256 mL, 1.7 mmol) was added followed by iodomethane (1.06 mL, 17 mmol). The reaction was allowed to stir overnight at room temperature. The reaction was poured into water and extracted with ethyl acetate. The combined organics was washed with water (2×), brine (1×), dried over magnesium sulfate filtered and concentrated. The resulting material was purified by column chromatography on silica gel, using a gradient of 1% to 3% ethyl acetate in hexane. The first fractions contained the product and another side product. This fraction was added to another synthesis of this compound (starting with 0.250 g 4-Bromo-5-methoxy-2-(4-methoxyphenyl)-benzofuran) for the final cleavage reaction.

2-(4-Hydroxy-phenyl)-4-methyl-benzofuran-5-ol 137

The crude 5-Methoxy-2-(4-methoxyphenyl)-4-methyl-benzofuran 136 (0.134 g) was taken into a sealed tube along with enough pyridine hydrochloride to fill the tube halfway and heated at 200° C. for 2.5 hours. The reaction was dissolved into a mixture of ethyl acetate and 1 N HCl. The layers were separated and the aqueous layer was extracted with ethyl acetate (2×). The combined organics was washed with 1 N HCl (1×), water (1×) and then dried over magnesium sulfate, filtered and concentrated. The resulting material was purified by column chromatography on silica gel, using 30% ethyl acetate in hexanes as the eluent to yield the desired product (0.090 g, 23.4% based on starting 4-Bromo-5-methoxy-2-(4-methoxyphenyl)-benzofuran from two runs) as a tan powder: Mp. 221–222° C.; $^1$H NMR (DMSO-d$_6$) δ 9.81 (s, 1 H), 8.94 (s, 1 H), ) 7.70 (d, 2 H, J=8.6 Hz), 7.16 (d, $_1$ H, J=8.9 Hz), 7.14 (s, 1 H), 6.86 (d, 2 H, J=8.6 Hz), 6.72 (d, 1 H, J=8.6 Hz), 2.27 (s, 3 H); MS 241 (M+H)$^+$.

2-(4-Hydroxy-phenyl)7-[1,3,4]oxadiazol-2-yl-benzofuran-5-ol 138

Compound 24 (0.6 g, 2.2 mmol) in DMF (3–5 mL) and hydrazine monohydrate (0.25 mL, 5 mmol) was treated with EDCI (1-(3-Dimethylaminopropyl)-3-ethylcarbodiimide hydrochloride) (0.64 g, 3.3 mmol) and the reaction allowed to stir at rt for several hours. The reaction was worked up by adding water and extracting twice with EtOAc; The combined EtOAc extracts were washed with brine and dried over MgSO$_4$. The EtOAc was concentrated to render 125 mg of the crude acyl hydrazide which was used as is for the next step. The crude acyl hydrazide from the previous step was treated with 3–5 mL of triethyl orthoformate and catalytic p-toluenesulfonic acid and heated to reflux for 30 minutes. The reaction mixture was allowed to cool to rt and was poured into 2 N HCl aq, extracted with EtOAc, washed with 2 N HCl aq, saturated NaHCO$_3$ aq, brine, and dried over MgSO$_4$. Filtration and concentration followed by chromatography on silica gel (1:19 MeOH/CH$_2$Cl$_2$) gave 15 mgs of 138: MP=260–266° C.; $^1$H NMR (DMSO-d$_6$) δ 9.94 (brs, 1 H), 9.75 (br s, 1 H), 9.45 (s, 1 H), 7.79 (d, 2 H, J=8.7 Hz), 7.33 (d, 1 H, J=2.4 Hz), 7.20 (s, 1 H), 7.18 (d, 1 H, J=2.4 Hz), 6.92 (d, 2 H, J=8.7 Hz); MS 295 (M+H)$^+$.

Synthesis of Compounds from Scheme 13

2,2,2-Trifluoro-1-[5-methoxy-2-(4-methoxy-phenyl)-benzofuran-7-yl]-ethanol 139

To a solution of 2 (1.2 g, 4.3 mmol) and Trimethylsilyltrifluoromethane (20 ml of 0.5M in THF, 10 mmol) in THF (20 ml) was added TBAF (10 ml of 1.0M in THF, 10 mmol) and the reaction was stirred at rt. After 30 min, the rextion was poured into 2N HCl and extracted with ether. The ether was dried, concentrated and the product was purified by column chromatography (eluent 10% Et OAc/Hex) to give 139 as a solid (1.2 g, 80%); Mp=120–122° C., $^1$H NMR (CDCl$_3$) δ 7.75 (d, 2 H, J=8.8 Hz), 7.15–6.95 (m, 4 H), 6.84 (s, 1 H), 5.59 (m, 1 H), 3.86 (s, 6 H); MS 353 (M+H)$^+$

5-Methoxy-2-(4-methoxy-phenyl)-7-(2,2,2-trifluoro-ethyl)-benzofuran 140

To a solution of 139 (1.2 g, 3.4 mmol) in diethyl ether (30 ml) was added NaH (0.41 g, 17 mmol) and the reaction was stirred for 15 min. P-Tosyl chloride (3.2 g, 17 mmol) was added and the reaction was stirred for 1 hr. The reaction was carefully poured into water and extracted with ether which was dried, concentrated to give an oil which was purified by column chromatography (eluent 10% EtOAc/hex) to give the tosylated intermediate as a white solid. Mp=113–115° C. A solution of the tosylated intermediate thus prepared (1.2 g, 2.3 mmol) and LiAlH$_4$ (20 ml of 1.0 M, 20 mmol) in THF (30 ml) was heated to reflux. After 5 hr, the reaction was cooled, quenched with 2N HCl and extracted with EtOAc. The organic layer was dried, concentrated and the product was purified by column chromatography (10% EtOAc/hex) to give a solid. The solid was triturated with MeOH and filtered to give 140 as a white solid (0.060 g, 8%).

2-(4-Hydroxy-phenyl)-7-(2,2,2-trifluoro-ethyl)-benzofuran-5-ol 141

A mixture of 140 (50 mg, 0.15 mmol) and Pyridine HCl (3 g) was heated to 200° C. After 1 hr, the reaction was cooled, diluted with water and extracted with EtOAc. The EtOAc was dried over MgSO$_4$, concentrated to give a solid which was triturated with CH$_2$Cl$_2$ and filtered to give 141 (30 mg, 65%): Mp=210–213° C.; $^1$H NMR (DMSO-d$_6$) δ 9.86 (s, 1 H), 9.28 (s, 1 H), 7.71 (d, 2 H, J=8.8 Hz), 7.05 (s, 1 H), 6.89–6.86 (m, 3 H), 6.69 (d, 1 H, 2.0 Hz), 3.91–3.84 (m, 2 H); MS 307 [M−H]$^-$ 2-(4-Methoxy-phenyl)-benzofuran-5-carboxylic acid methyl ester 142

A mixture of Methyl 3-Iodo-4-hydroxybenzoate (0.7 g, 2.5 mmol), 4-Methoxyphenylacetylene (0.33 g, 2.5 mmol), Pd(Cl)$_2$(PPh$_3$)$_2$ (0.05 g) and CuI (0.03 g) in DMF/Piperidine (20 ml) was heated at 6° C. After 2 hr, the reaction was cooled and poured into 2N HCl. The aqueous layer was extracted with EtOAc and then separated, dried, concentrated to give a solid. The solid was triturated with MeOH, filtered to give 142 (0.5 g, 71%): Mp=157–159° C.; $^1$H NMR (CDCl$_3$) δ 8.28 (d, 1 H, J=1.3 Hz), 7.97 (dd, 1 H, J=8.5 Hz, 1.7 Hz), 7.82–7.79 (m, 2 H), 7.51 (d, 1 H, 8.5 Hz), 6.99 (d, 2 H, J=8.3 Hz), 6.93 (d, 1 H, J=9 Hz), 3.94 (s, 3 H), 3.87 (s, 3 H); MS 283 (M+H)$^+$ 2-(4-Hydroxy-phenyl)-benzofuran-5-carboxylic acid 143

A mixture of 142 (0.45 g, 1.6 mmol) and Pyridine HCl (10 g) was heated to 200° C. After 1 hr, the reaction was cooled and diluted with water. The aqueous layer was extracted with EtOAc, dried, concentrated to give a solid which was triturated. with CH$_2$Cl$_2$ and filtered to give 143 (0.23 g, 58%): Mp>300° C.; $^1$H NMR (DMSO-d$_6$) δ 12.87 (br s, 1 H), 9.86 (br s, 1 H), 8.21 (d, 1 H, J=1.6 Hz), 7.86 (dd, 1 H, J=8.8 Hz, 1.5 Hz), 7.76 (d, 2 H, J=8.8 Hz), 7.67 (d, 1 H, J=8.8 Hz), 7.29 (s, 1 H), 6.89 (dd, 2 H, J=7.7 Hz, 2.0 Hz); MS 253 (M−H)$^-$ 4-(5-Hydroxymethyl-benzofuran-2-yl)-phenol 144

Compound 143 (0.21 g, 0.83 mmol) in THF (10 ml) was treated with BH$_3$·THF (4.0 ml of 1.0 M) and the reaction was heated to reflux. After 2 hr, the reaction was cooled and then poured into 2NHCl and extracted with EtOAc. The organic layer was dried, concentrated and the product was purified by cloumn chromatography (60% EtOAc/Hexane) to give 144 as a solid (0.07 g, 37%); Mp=248–250° C.; $^1$H NMR (DMSO-d$_6$) δ 9.86 (br s, 1 H), 7.72 (d, 2 H, J=8.3 Hz), 7.52–7.49 (m, 2 H), 7.19 (dd, 1 H, J=8.3 Hz, 1.6 Hz), 7.15 (s, 1 H), 6.87 (d, 2 H, J=8.8 Hz), 5.19 (t, 1 H, J=5.2 Hz), 4.56 (d, 2 H, J=4.1 Hz); MS 239 (M−H)$^-$.

What is claimed is:

1. A method of treating or inhibiting endometriosis in a mammal in need thereof, which comprises providing to said mammal an effective amount of a compound of formula I, having the structure

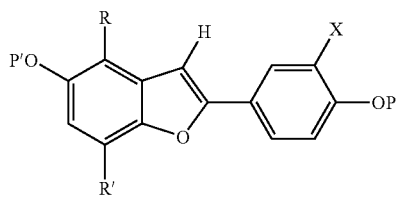

wherein

P and P' are each, independently, hydrogen, alkyl of 1–6 carbon atoms, or acyl of 2–7 carbon toms;

X is hydrogen or halogen;

R is hydrogen, alkyl of 1–6 carbon atoms, halogen, —CN, or —CHO;

R' is alkoxy of 1–6 carbon atoms, or cyanoalkyl having 1–6 carbon atoms in the alkyl moiety;

or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 7,022,733 B2 | Page 1 of 1 |
| APPLICATION NO. | : 10/828970 | |
| DATED | : April 4, 2006 | |
| INVENTOR(S) | : Christopher P. Miller et al. | |

It is certified that error appears in the above-identified patent and that said Letters Patent is hereby corrected as shown below:

On the patent title page (75), please delete inventors "Heather A. Harris, James C. Keith, Jr., and, Leo M. Albert".

On the patent title page (75), please insert additional inventor -- C. Richard Lyttle --.

Signed and Sealed this

Twenty-ninth Day of April, 2008

JON W. DUDAS
*Director of the United States Patent and Trademark Office*

SEQUENCE LISTING

```
<160> NUMBER OF SEQ ID NOS: 3

<210> SEQ ID NO 1
<211> LENGTH: 19
<212> TYPE: DNA
<213> ORGANISM: Rat

<400> SEQUENCE: 1
cacacggatg gcgcatact                                              19

<210> SEQ ID NO 2
<211> LENGTH: 19
<212> TYPE: DNA
<213> ORGANISM: Rat

<400> SEQUENCE: 2
ctcgggatgc accatgaag                                              19

<210> SEQ ID NO 3
<211> LENGTH: 24
<212> TYPE: DNA
<213> ORGANISM: Rat

<400> SEQUENCE: 3
cggcactggt ttccctcaca tgct                                        24
```